United States Patent
Pregibon et al.

(10) Patent No.: US 9,476,101 B2
(45) Date of Patent: Oct. 25, 2016

(54) SCANNING MULTIFUNCTIONAL PARTICLES

(75) Inventors: Daniel C. Pregibon, Cambridge, MA (US); Davide M. Marini, Wellesley, MA (US); Isaac Stoner, Cambridge, MA (US); Andreas Windemuth, Belmont, MA (US); Timothy Erps, Salem, MA (US)

(73) Assignee: Firefly Bioworks, Inc., Cambridge, MA (US)

( * ) Notice: Subject to any disclaimer, the term of this patent is extended or adjusted under 35 U.S.C. 154(b) by 0 days.

(21) Appl. No.: 13/702,860

(22) PCT Filed: Jun. 7, 2011

(86) PCT No.: PCT/US2011/039529
§ 371 (c)(1),
(2), (4) Date: Feb. 7, 2013

(87) PCT Pub. No.: WO2011/156432
PCT Pub. Date: Dec. 15, 2011

(65) Prior Publication Data
US 2013/0210653 A1  Aug. 15, 2013

Related U.S. Application Data

(60) Provisional application No. 61/352,018, filed on Jun. 7, 2010, provisional application No. 61/365,738, filed on Jul. 19, 2010, provisional application No. 61/387,958, filed on Sep. 29, 2010.

(51) Int. Cl.
*C12Q 1/68* (2006.01)
*G01N 15/14* (2006.01)
(Continued)

(52) U.S. Cl.
CPC ............ *C12Q 1/6888* (2013.01); *C12Q 1/689* (2013.01); *C12Q 1/6809* (2013.01);
(Continued)

(58) Field of Classification Search
CPC .............................. C12Q 1/6888; G01N 21/47
USPC ......................................... 435/6.1; 422/82.05
See application file for complete search history.

(56) References Cited

U.S. PATENT DOCUMENTS

| | | |
|---|---|---|
| 3,687,808 A | 8/1972 | Merigan et al. |
| 4,194,066 A | 3/1980 | Kaetsu et al. |

(Continued)

FOREIGN PATENT DOCUMENTS

| | | |
|---|---|---|
| GB | 2388652 B | 3/2005 |
| JP | 54074886 A | 6/1979 |

(Continued)

OTHER PUBLICATIONS

Chen et al. Microfluid Nanofluid (2009) 6:529-537.*

(Continued)

*Primary Examiner* — Betty Forman
(74) *Attorney, Agent, or Firm* — Proskauer Rose LLP; Fangli Chen

(57) ABSTRACT

The present invention provides, among other things, methods and systems for characterizing multifunctional objects using a flow-through device, such as, a flow cytometer. In some embodiments, an inventive method according to the present invention includes one more steps of (a) interrogating a plurality of objects (e.g., particles), wherein each individual object (e.g., particle) comprises one or more interrogation regions detectable as a sequence of events; (b) recording multiple events, wherein each individual event corresponds to each individual interrogation region detectable above a pre-determined triggering threshold; (c) grouping the recorded multiple events, and (d) characterizing the plurality of objects based on the grouped events.

18 Claims, 30 Drawing Sheets

(51) Int. Cl.
  *G01N 21/47* (2006.01)
  *G01N 21/64* (2006.01)
  *G01N 33/68* (2006.01)
  *C12Q 1/70* (2006.01)

(52) U.S. Cl.
  CPC ......... *C12Q 1/6813* (2013.01); *C12Q 1/6816* (2013.01); *C12Q 1/6834* (2013.01); *C12Q 1/6895* (2013.01); *C12Q 1/70* (2013.01); *G01N 15/14* (2013.01); *G01N 21/47* (2013.01); *G01N 21/6428* (2013.01); *G01N 33/6803* (2013.01)

(56) References Cited

U.S. PATENT DOCUMENTS

| | | |
|---|---|---|
| 4,683,194 A | 7/1987 | Saiki et al. |
| 4,743,545 A | 5/1988 | Torobin |
| 4,845,205 A | 7/1989 | Huynh Dinh et al. |
| 4,929,400 A | 5/1990 | Rembaum et al. |
| 4,981,957 A | 1/1991 | Lebleu et al. |
| 5,117,357 A | 5/1992 | Inoue |
| 5,118,800 A | 6/1992 | Smith et al. |
| 5,130,302 A | 7/1992 | Spielvogel et al. |
| 5,134,066 A | 7/1992 | Rogers et al. |
| 5,175,273 A | 12/1992 | Bischofberger et al. |
| 5,210,015 A | 5/1993 | Gelfand et al. |
| 5,319,080 A | 6/1994 | Leumann |
| 5,359,044 A | 10/1994 | Cook et al. |
| 5,367,066 A | 11/1994 | Urdea et al. |
| 5,393,878 A | 2/1995 | Leumann |
| 5,432,272 A | 7/1995 | Benner |
| 5,446,137 A | 8/1995 | Maag et al. |
| 5,457,187 A | 10/1995 | Gmeiner et al. |
| 5,459,255 A | 10/1995 | Cook et al. |
| 5,466,786 A | 11/1995 | Buhr et al. |
| 5,484,908 A | 1/1996 | Froehler et al. |
| 5,502,177 A | 3/1996 | Matteucci et al. |
| 5,514,785 A | 5/1996 | Van Ness et al. |
| 5,519,134 A | 5/1996 | Acevedo et al. |
| 5,525,711 A | 6/1996 | Hawkins et al. |
| 5,552,540 A | 9/1996 | Haralambidis |
| 5,567,811 A | 10/1996 | Misiura et al. |
| 5,576,427 A | 11/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,596,091 A | 1/1997 | Switzer |
| 5,597,909 A | 1/1997 | Urdea et al. |
| 5,610,300 A | 3/1997 | Altmann et al. |
| 5,614,617 A | 3/1997 | Cook et al. |
| 5,627,053 A | 5/1997 | Usman et al. |
| 5,639,873 A | 6/1997 | Barascut et al. |
| 5,645,985 A | 7/1997 | Froehler et al. |
| 5,646,265 A | 7/1997 | McGee |
| 5,658,873 A | 8/1997 | Bertsch-Frank et al. |
| 5,668,268 A | 9/1997 | Tang et al. |
| 5,670,633 A | 9/1997 | Cook et al. |
| 5,677,196 A | 10/1997 | Herron et al. |
| 5,681,941 A | 10/1997 | Cook et al. |
| 5,700,920 A | 12/1997 | Altmann et al. |
| 5,763,588 A | 6/1998 | Matteucci et al. |
| 5,792,747 A | 8/1998 | Schally et al. |
| 5,830,653 A | 11/1998 | Froehler et al. |
| 5,876,924 A | 3/1999 | Zhang et al. |
| 5,879,900 A | 3/1999 | Kim et al. |
| 5,916,539 A | 6/1999 | Pilgrimm |
| 5,945,526 A | 8/1999 | Lee et al. |
| 5,981,180 A | 11/1999 | Chandler et al. |
| 6,001,571 A | 12/1999 | Mandecki |
| 6,005,096 A | 12/1999 | Matteucci et al. |
| 6,150,102 A | 11/2000 | Mills, Jr. et al. |
| 6,159,739 A | 12/2000 | Weigl et al. |
| 6,251,303 B1 | 6/2001 | Bawendi et al. |
| 6,319,426 B1 | 11/2001 | Bawendi et al. |
| 6,322,901 B1 | 11/2001 | Bawendi et al. |
| 6,344,316 B1 | 2/2002 | Lockhart et al. |
| 6,376,742 B1 | 4/2002 | Zdrahala et al. |
| 6,423,551 B1 | 7/2002 | Weiss et al. |
| 6,426,513 B1 | 7/2002 | Bawendi et al. |
| 6,444,143 B2 | 9/2002 | Bawendi et al. |
| 6,488,872 B1 | 12/2002 | Beebe et al. |
| 6,532,061 B2 | 3/2003 | Ortyn et al. |
| 6,576,291 B2 | 6/2003 | Bawendi et al. |
| 6,592,821 B1 | 7/2003 | Wada et al. |
| 6,649,138 B2 | 11/2003 | Adams et al. |
| 6,709,813 B1 | 3/2004 | Bergmeyer et al. |
| 6,815,064 B2 | 11/2004 | Treadway et al. |
| 6,934,408 B2 | 8/2005 | Frost et al. |
| 7,255,994 B2 | 8/2007 | Lao |
| 7,319,003 B2 | 1/2008 | Cantor et al. |
| 7,438,792 B2 | 10/2008 | Mathies et al. |
| 7,709,544 B2 | 5/2010 | Doyle et al. |
| 7,947,487 B2 | 5/2011 | Doyle et al. |
| 8,034,629 B2 | 10/2011 | Chapin et al. |
| 8,232,049 B2 | 7/2012 | Nilsen et al. |
| 8,535,644 B2 | 9/2013 | Haghgooie et al. |
| 8,609,337 B2 | 12/2013 | Pregibon et al. |
| 8,647,742 B2 | 2/2014 | Dendukuri et al. |
| 2001/0023078 A1 | 9/2001 | Bawendi et al. |
| 2002/0001813 A1 | 1/2002 | Taylor et al. |
| 2002/0004573 A1 | 1/2002 | Domschke et al. |
| 2002/0056945 A1 | 5/2002 | Gelbart |
| 2002/0155490 A1 | 10/2002 | Skinner et al. |
| 2002/0165198 A1 | 11/2002 | Singh et al. |
| 2002/0197614 A1 | 12/2002 | Weir et al. |
| 2003/0032203 A1 | 2/2003 | Sabatini et al. |
| 2003/0045597 A1 | 3/2003 | Randolph et al. |
| 2003/0049629 A1 | 3/2003 | Edman et al. |
| 2003/0059764 A1 | 3/2003 | Ravkin et al. |
| 2003/0108900 A1 | 6/2003 | Oliphant et al. |
| 2003/0143604 A1 | 7/2003 | Storhoff et al. |
| 2004/0005352 A1 | 1/2004 | Lopez et al. |
| 2004/0038408 A1 | 2/2004 | Abbott et al. |
| 2004/0043506 A1 | 3/2004 | Haussecker et al. |
| 2004/0069857 A1 | 4/2004 | Leblans et al. |
| 2004/0110141 A1 | 6/2004 | Pusey et al. |
| 2004/0126820 A1 | 7/2004 | Chan et al. |
| 2004/0209376 A1 | 10/2004 | Natan et al. |
| 2004/0210289 A1 | 10/2004 | Wang et al. |
| 2004/0248163 A1 | 12/2004 | Kramer et al. |
| 2005/0043428 A1 | 2/2005 | Caneba et al. |
| 2005/0147973 A1 | 7/2005 | Knott |
| 2005/0172476 A1 | 8/2005 | Stone et al. |
| 2005/0196702 A1 | 9/2005 | Bryant et al. |
| 2005/0214737 A1 | 9/2005 | Dejneka et al. |
| 2005/0214825 A1 | 9/2005 | Stuelpnagel |
| 2005/0233318 A1 | 10/2005 | Chee et al. |
| 2006/0019258 A1 | 1/2006 | Yeakley |
| 2006/0094025 A1 | 5/2006 | Getts et al. |
| 2006/0121122 A1 | 6/2006 | Nakajima et al. |
| 2006/0147924 A1 | 7/2006 | Ramsing et al. |
| 2006/0201390 A1 | 9/2006 | Lahann et al. |
| 2006/0228386 A1 | 10/2006 | Stephens et al. |
| 2006/0228735 A1 | 10/2006 | Bobrow et al. |
| 2006/0228742 A1 | 10/2006 | Hashmi et al. |
| 2007/0003940 A1 | 1/2007 | Wang |
| 2007/0037195 A1 | 2/2007 | Ho |
| 2007/0054119 A1 | 3/2007 | Garstecki et al. |
| 2007/0065844 A1 | 3/2007 | Golub et al. |
| 2007/0105972 A1 | 5/2007 | Doyle et al. |
| 2008/0026394 A1 | 1/2008 | Labgold et al. |
| 2008/0176216 A1* | 7/2008 | Doyle et al. .................. 435/5 |
| 2008/0182239 A1 | 7/2008 | Mullinax et al. |
| 2008/0213912 A1 | 9/2008 | Randall et al. |
| 2008/0234144 A1 | 9/2008 | Ho et al. |
| 2008/0305481 A1 | 12/2008 | Whitman et al. |
| 2009/0036316 A1 | 2/2009 | Drmanac |
| 2009/0061424 A1 | 3/2009 | Chen |
| 2009/0063095 A1 | 3/2009 | Bagwell |
| 2009/0156425 A1 | 6/2009 | Walt et al. |
| 2009/0201504 A1 | 8/2009 | Ho et al. |

(56) References Cited

U.S. PATENT DOCUMENTS

| | | |
|---|---|---|
| 2010/0129855 A1 | 5/2010 | Kataoka et al. |
| 2011/0129941 A1 | 6/2011 | Kumacheva et al. |
| 2012/0100526 A1 | 4/2012 | Czajka et al. |

FOREIGN PATENT DOCUMENTS

| | | |
|---|---|---|
| JP | 11 118819 A | 4/1999 |
| WO | WO-98/39352 A1 | 9/1998 |
| WO | WO-99/14226 A2 | 3/1999 |
| WO | WO-00/49385 A2 | 8/2000 |
| WO | WO-00/74927 A1 | 12/2000 |
| WO | WO-01/16152 A2 | 3/2001 |
| WO | WO-2004/026457 A1 | 4/2004 |
| WO | WO-2005/103106 A1 | 11/2005 |
| WO | WO-2004/076056 A3 | 12/2006 |
| WO | WO-2007/050704 A2 | 5/2007 |
| WO | WO 2007/071062 A1 | 6/2007 |
| WO | WO-2007/050704 A3 | 8/2007 |
| WO | WO-2007/075894 A3 | 1/2008 |
| WO | WO-2008/063758 A2 | 5/2008 |
| WO | WO-2008/124423 A1 | 10/2008 |
| WO | WO 2009/002225 A2 | 12/2008 |
| WO | WO 2009/021923 A1 | 2/2009 |
| WO | WO-2009/029742 A1 | 3/2009 |
| WO | WO-2009/046149 A1 | 4/2009 |
| WO | WO-2011/156432 A2 | 12/2011 |
| WO | WO-2011/156434 A2 | 12/2011 |

OTHER PUBLICATIONS

Pregibon et al. Science 315.5817 (2007): 1393-1396.*
Doerr. Nature Methods 4.5 (2007): 381-381.*
Broude, N. et al., DNA microarrays with stem-loop DNA probes: preparation and applications, Nucleic Acids Research, 29(19):pp. 1-11 (2001).
Jang, E. and Koh, W., Multiplexed enzyme-based bioassay within microfluidic devices using shape-coded hydrogel microparticles, Sensors and Actuators B, 143(681-688 (2010).
Sakai-Kato, K. and Ishikura, K., Integration of Biomolecules into Analytical Systems by Means of Silica Sol-Gel Technology, Analytical Sciences, 25:969-978 (2009).
Tsagkogeorgas, F. et al., Encapsulation of biomolecules for bioanalytical purposes: Preparation of diclofenac antibody-doped nanometer-sized silica particles by reverse micelle and sol-gel processing, Analytica Chimica Acta, 573-574:133-137 (2006).
International Search Report for PCT/US2015/032319, 6 pages (Oct. 8, 2015).
Written Opinion for PCT/US2015/032319, 10 pages (Oct. 8, 2015).
International Search Report of PCT/US11/39539,dated Feb. 9, 2012, 3 pages.
Written Opinion of PCT/US11/39539,dated Feb. 9, 2012, 5 pages.
European Search Report, Application No. 11793062.8, Nov. 20, 2013, 10 pages.
He et al., Nanowire Sensors for Multiplexed Detection of Biomolecules Current Opinion in Chemical Biology, 12:522-528 (2008).
Meade et al., Multiplexed DNA Detection Using Spectrally Encoded Prous $SiO_2$ Photonic Crystal Particles, Analytical Chemistry, 81(7):2618-2625 (2009).
Albretsen et al., Applications of Magnetic Beads with Covalently Attached Oligonucleotides in Hybridization, Analytical Biochemistry, 189; 40-50 (1990).
Armstrong, B. et al., Suspension arrays for high throughput, multiplexed single nucleotide polymorphism genotyping, Cytometry, 40(2):102-108 (2000).
Australian Patent Examination Report No. 1 for AU2007324117, dated Aug. 15, 2012, 4 pages.
Battersby, B.J. et al., Toward Larger Chemical Libraries: Encoding with Fluorescent Colloids in Combinatorial Chemistry, J. Am. Chem. Soc. 122(9):2138-9 (2000).
Beebe, D.J. et al., Functional hydrogel structures for autonomous flow control inside microfluidic channels, Nature 404(6778):588-90 (2000).
Bong et al., Magnetic Barcoded Hydrogel Microparticles for Multiplexed Detection, Langmuir, 26(11); 8008-8014 (2010).
Bong, K. et al., Lock Release Lithography for 3D and Composite Microparticles, Lab on a Chip 9(70):863-86 (2009).
Braeckmans, K. et al., Encoding microcarriers by spatial selective photobleaching, Nature Materials 2(3):169-73 (2003).
Braeckmans, K. et al., Encoding Microcarriers: Present and Future Technologies, Nat Rev Drug Discovery, 1(6):447-456 (2002).
Bullard et al., Direct comparison of nick-joining activity of the nucleic acid ligases from bacteriophage T4, Biochem J, 398; 135-144 (2006).
Castoldi et al., A sensitive array for microRNA expression profiling (miChip) based on locked nucleic acids (LNA), RNA 12(5):913-20 (2006).
Chapin et al., High-throughput flow alignment of barcoded hydrogel microparticles, Lab Chip 9(21):3100-9 (2009).
Chapin et al., Ultrasensitive Multiplexed MicroRNA Quantification on Encoded Gel Microparticles Using Rolling Circle Amplification, Analytical Chemistry 83(18):7179-85 (2011).
Chen et al., Real-time quantification of microRNAs by stem-loop RT-PCR, J. Nucleic Acids Res. 33(20):e179 (2005).
Chung, S. et al., Plastic microchip flow cytometer based on 2- and 3- dimensional hydrodynamic flow focusing, Microsystem Technno. 9(8):535-533 (2003).
Chung, T. et al., Recent advances in miniaturized microfluidic flow cytometry for clinical use, Electrophersis, 28(24):4511-20 (2007).
Ciba Formulators Guide for Coatings—Photoinitiators for UV Curing. Ciba Specialty Chemicals. Available on the web Sep. 2003 at http://www.mufong.com.tw/Ciba/ciba_guid/photo_uv_2.pdf.
Collins et al., A DNA polymorphism discovery resource for research on human genetic variation. Genome Res. 8(12):1229-31 (1998).
Crooke et al., Antisense Research and Applications, 289-302 (1993).
Crosland-Taylor, P.J., A device for counting small particles suspended in a fluid through a tube, Nature, 171(4340):37-8 (1953).
Cruise, G. M. et al., Characterization of permeability and network structure of interfacially photopolymerized poly(ethylene glycol) diacrylate hydrogels, Biomaterials 19(14):1287-94 (1998).
Cunin, F. et al., Biomolecular screening with encoded porous-silicon photonic crystals, Nat. Mater. 1(1):39-41 (2002).
De Jager, W. et al., Solid-phase and bead-based cytokine immunoassay: a comparison, Methods 38(4):294-303 (2006).
Dendukuri et al., Continuous-flow lithography for high-throughput microparticle synthesis, Nature Materials 5(5):365-69 (2006).
Dendukuri et al., Controlled Synthesis of Nonspherical Microparticles Using Microfluids, Langmuir 21: 2113-2116 (2005).
Dendukuri et al., Stop-flow lithography in a microfluidic device, Lab on a Chip 7(7):818-28 (2007).
Dendukuri et al., Synthesis and self-assembly of amphiphilic polymeric microparticles, Langmuir 23(8):4669-74 (2007).
Dunbar, S. A. et al., Quantitative, multiplexed detection of bacterial pathogens: DNA and protein applications of the Luminex LabMAP system, J. Microbial. Methods 53(2):245-52 (2003).
Englisch et al., Chemically Modified Oligonucleotides as Probes and Inhibitors, Angewandte Chemie International Edition, 30(6):613-722 (1991).
Evans, M. et al., An encoded particle array tool for multiplex bioassays, Assay Drug Dev. Techno. 1(1):199-207 (2003).
Eyal and Quake, Velocity-independent microfluidic flow cytometry, Electrophoresis, 23(16):2653-7 (2002).
Faivre M. et al., Geometrical focusing of cells in a microfluidic device: an approach to separate blood plasma, Biorheology 43(3):147-59 (2006).
Fan, J.B. et al., Highly parallel genomic assays, Nat. Rev. Genet. 7(8):632-44 (2006).
Fenniri, S. et al., Preparation, physical properties, on-bead binding assay and spectroscopic reliability of 25 barcoded polystyrene-poly(ethylene glycol) graft copolymers, J. Am. Chem. Soc. 125(35):10546-60 (2003).

(56) References Cited

OTHER PUBLICATIONS

Ferguson, J. A. et al., High-density fiber-optic DNA random microsphere array, Anal Chem. 72(22):5618-24 (2000).
Fialkowski et al., Self-assembly of Polymerc Microspheres of Complex Internal Structures, Nature Materials 4(1):93-97 (2005).
Finkel, N.H. et al., Barcoding the Microwold, Anal Chem. 76:353A-359A (2004).
Fisher et al., Photoinitiated Polymerization of Biomaterials, Annu. Rev. Mater. Res. 31:171-81 (2001).
Fodor, S. P. et al., Multiplexed biochemical assays with biological chips, Nature 364(6437):555-6 (1993).
Fotin et al., Parallel thermodynamic analysis of duplexes on oligodeoxyribonucleotide microchips, Nucleic Acids Research 26(6):1515-1521 (1998).
Fulton, R.J. et al., Advanced multiplexed analysis with the FlowMetrix system, Clin. Chem 43(9):1749 (1997).
Gershon, D., Microarray technology: an array of opportunities, Nature 416(6883):885-91 (2002).
Ghosh et al., Covalent attachments of oligonucleotides to solid supports, Nucleic Acids Research, 15; 5353-5372 (1987).
Gill et al., Encapsulation of Biologicals within Silicate, Siloxane, and Hybrid Sol-Gel Polymers: An Effecient and Generic Approach, J. Am. Chem. Soc. 120: 8587-98 (1998).
Hall et al., Integrons found in different locations have identical 5' ends but variable 3' ends, Journal of Bacteriology, 179: 6286-6294 (1994).
Han, M. et al., Quantum-dot-tagged microbeads for multiplexed optical coding of biomolecules, Nat Biotechnol. 19(7):631-5 (2001).
Hergt, R. et al., Physical Limits of Hyperthermia using Magnetite Fine Particles, IEEE Trans. Maqn. 34(5):3745-54 (1998).
Hillborg et al., Crosslinked Polydimethylsilozane Exposed to Ocygen Plasma Studied by Neutron Reflectrometry and Other Surface Specific Techniques, Polymer 41(18): 6851-6863 (2000).
Huh, D., et al., Microfluidics for flow cytometric analysis of cells and particles, Physiol. Meas. 26(3):R73-98 (2005).
Hunt, H.C. et al., Optofluidic Integration for Microanalysis, Microfluidics and Nanofluidics 4:53-79 (2008).
International Search Report for PCT/US2006/041668 dated Jun. 18, 2007, 5 pages.
International Search Report for PCT/US2007/080426 dated Sep. 30, 2008, 6 pages.
International Search Report for PCT/US2009/061474 dated on May 28, 2009, 3 pages.
International Search Report for PCT/US2009/66778 dated on Jan. 13, 2010, 2 pages.
International Search Report for PCT/US2011/39531 dated Feb. 23, 2012, 6 pages.
International Search Report for PCT/US2013/029854 dated Jul. 4, 2013, 4 pages.
Irizarry, R. A. et al., Comparison of Affymetrix GeneChip expression measures, Bioinformatics 22(7):789-94 (2006).
Jo et al., Three-Dimensional Micro-Channel Fabrication in Polydimethylsiloxane (PDMS) Elastomer, Journal of Microelctromechanical Systems 9(1): 76-81 (2000).
Ju et al., Fluorescence energy transfer dye-labeled primers for DNA sequencing and analysis, Proc. Nat'l Acad. Sci., 92; 4347 (1995).
Kellar, K. et al., Multiplexed microsphere-based flow cytometric immunoassays for human cytokines, J. Immunol. Methods 279(1-2):277-85 (2003).
Kellar, K.L., et al., Multiplexed microsphere-based flow cytometric assays, Exp. Hematol. 30(11): 1227-37 (2002).
Kenis et al., Microfabrication Inside Capillaries Using Multiphase Laminar Flow Patterning, Science 285: 83-85 (1999).
Kim et al., Hydrodynamic Fabrication of Polymeric Barcoded Strips as Components for Parallelll Bio-Analysis and Programmable Microactuation, Lab Chip 5: 1168-1172 (2005).
Kohara, Y. et al., DNA probes on beads arrayed in a capillary, 'Bead-array', exhibited high hybridization performance, Nucleic Acids Res. 30(16):e87 (2002).
Kroschwitz, The Concise Encyclopedia Of Polymer Science And Engineering, 858-9 (1990).
Lee et al., Colour-barcoded magnetic microparticles for multiplexed bioassays, Nature Materials, 9; 745-749 (2010).
Lee et al., DNA-based bioanalytical microsystems for handheld device applications, Analytica Chemica 556(1):26-37 (2006).
Lu et al., MicroRNA expression profiles classify human cancers, Nature 435(7043):834-8 (2005).
Lund et al., Assessment of methods for covalent binding of nucleic acids to magnetic beads, DynabeadsTM and the characteristics of the bound nucletic acids in hybridization reactions, Nucleic Acids Research, 16; 10861-80 (1988).
Lyamichev et al., Invader Assay for SNP Genotyping, Methods in Molecular Biology 212:229-40 (2002).
MacBeath, G. and S.L Schreiber, Printing proteins as microarrays for high-throughput function determination, Science 289(5485):1760-3 (2000).
McClain et al., Microfluidic devices for the high-throughput chemical analysis of cells, Anal. Chem., 75(21):5646-55 (2003).
McHugh, T. M. et al., Simultaneous detection of antibodies to cytomegalovirus and herpes simplex virus by using flow cytometry and a microsphere-based fluorescence immunoassay, J. Clin. Microbia 26(10):1957-61 (1988).
Mellott, M.B., Release of protein from highly cross-linked hydrogels of poly(ethylene glycol) diacrylate fabricated by UV polymerization, Biomaterials 22(9):929-41 (2001).
Millman et al., Anisotropic Particle Synthesis in Dielectrophoretically Controlled Microdroplet Reactors, Nature Materials 4:98-102 (2005).
Moran, E. J. et al., Radio Frequency Tag Encoded Combinatorial Library Method for the Discovery of Tripeptide-Substituted Cinnamic Acid Inhibitors of the Protein Tyrosine Phosphatase PTP1B, J. Am. Chem. Soc. 117(43):10787-88 (1995).
Morgan, E. et al., Cytometric bead array: a multiplexed assay platform with applications in various areas of biology, Clin. Immunol. 110(3):252-66 (2004).
Mukhoadhyay, Microparticles of all Shapes and Chemistries, Analysical Chemistry 4247 (2006).
Nailis et al., Development and evaluation of different normalization strategies for gene expression studies in Candida albicans biofilms by real-time PCR. BMC Mol. Biol. 7:25 (2006).
Nazarenko et al., Multiplex quantitative PCR using self-quenched primers labeled with a single fluorophore, Nucleic Acids Research 30(9):e37 (2002).
Nicewarner-Pena et al., Submicrometer metallic barcodes, Science 294(5540):137-41 (2001).
Nicolaou, K. C. et al., Radiofrequency Encoded Combinatorial Chemistry, Agnew. Chem. Int. Ed. 34(20):2289 (1995).
Nie et al., Janus and Ternanry Particles Generated by Microfludic Synthesis: Design, Synthesis and selfassembly, J. Am. Chem. Soc. 128(29):9408-12 (2006).
Nisisako et al., Synthesis of Monodisperse Bicolored Janus Particles with Electrical Anisotropy Using a Microfluidic Co-Flow System, Adv. Mater. 18: 1152-1156 (2006).
Nolan T. et al., Quantification of mRNA using realtime RT-PCR, Nat. Protoc. 1(3):1559-1582 (2006).
Nolan, J.P. et al., Suspension array technology: evolution of the flat-array paradigm, Trends Biotechnol. 20(1):9 (2002).
Noor, M.R. et al., Electrical Detection of Single-Base DNA Mutation Using Functionalized Nanoparticles, Applied Physics Letters, 95(7), 4 pages (2009).
O'Connell et al., Testing of the BioSeeq (Smiths Detection Handheld PCR Instrument): Sensitivity, Specificity, and Effect of Interferents on Bacillus Assay Performance (2004).
Panda et al., Stop-flow lithography to generate cell-laden microgel particles, Lab on a Chip 8(7):1056-61 (2008).
Pearce, M.E. et al., Multifunctional nanorods for biomedical applications, Pharmaceutical Research, 24(12):2335-52 (2007).
Peck et al., A Method for High-Throughput Gene Expression Signature Analysis, Genome Biology, 7(7):R61 (2006).
Perro et al., Design and Sythesis of Janus Micro- and Nonoparticles, Journal of Materials Chemistry 15: 3745-3760 (2005).

(56) References Cited

OTHER PUBLICATIONS

Pregibon and Doyle, Optimization of encoded hydrogel particles for nucleic acid quantification, Anal. Chem. 81(12):4873-81 (2009).
Pregibon, D.C. et al., Magnetically and biologically active bead-patterned hydrogels, Langmuir 22(11):5122-8 (2006).
Ray UK Startup DNA Electronics Developing Handheld Device to Detect Genetic Risk for Drug AEs, Pharmacogenomics Reporter (2009).
Rehman, F. N. et al., Immobilization of acrylamide-modified oligonucleotides by copolymerization, Nucleic Acids Res. 27(2):649-55 (1999).
Research Highlights, Microparticle Synthesis by Continuous-Flow Lithography, Lab Chip 6: 707-709 (2006).
Research Highlights, Particle Shape Up, Nature 440: 848 (2006).
Roh, K.H. et al., Biphasic Janus particles with nanoscale anisotropy, Nature Materials 4(10):759-63 (2005).
Rolland et al., Direct Fabrication and Harvesting of Monodisperse, Shape-Specific Nanobiomaterials, J. Am. Chem. Soc. 127: 10096-100 (2005).
Rubina, A.Y. et al., Hydrogel-based protein microchips: manufacturing, properties, and applications, Biotechniques 34(5):1008-14, 1016-20, 1022 (2003).
Service, R. F., Radio Tags Speed Compound Service, Science 270(5236):577 (1995).
Sha, M. Y. et al., Multiplexed SNP genotyping using nanobarcode particle technology, Anal Bioanal. Chem. 384(3):658-66 (2006).
Shiku et al., Oxygen Permeability of Surface-Modified Poly(dimethylsiloxane) Charactarized by Scanning Electrochemical Microscopy, Chemistry Letters 35(2): 234-5 (2006).
Simonnet, C., et al., High-throughput and high-resolution flow cytometry in molded microfluidic devices, Anal. Chem. 78(16):5653-63 (2006).
Sinclair et al., Design, construction, characterization, and application of a hyperspectral microarray scanner, Appl. Optics, 43(10):2079-88 (2004).
Sorokin et al., Kinetics of hybridization on surface oligonucleotide microchips: Theory, experiment, and comparison with hybridization on gel-based microchips, Journal of Biomolecular Structure & Dynamics 24(1): 57-66 (2006).
Stears et al., A novel, sensitive detection system for high-density microarrays using dendrimer technology, Physiol Genomics 3: 93-9 (2000).
Stevens, P. W. etal., DNA hybridization on microparticles: determining capture-probe density and equilibrium dissociation constants, Nucleic Acids Res. 27(7):1719-27 (1999).
Stockton et al., Multiplex PCR for typing and subtyping influenza and respiratory syncytial viruses, J. Clin. Microbiol 36(10):2990-5 (1998).
Su, X. et al., Composite organic-inorganic nanoparticles (COINs) with chemically encoded optical signatures, Nano Lett. 5(1):49-54 (2005).
Sugiura et al., Preparation of Monodispersed Polymeric Microspheres over 50 Micron Employing Microchanncel Emulsification, Ind. Eng. Chem. Res. 4043-7 (2002).
Tamura et al., MEGA5: molecular evolutionary genetics analysis using maximum likelihood, evolutionary distance, and maximum parsimony methods, Mol. Biol. Evol. 28(10):2731-9 (2011).
Vaino, A R. et al., Euclidean shape-encoded combinatorial chemical libraries, Nat. Acad. Sc. U.S.A 97(14):7692-6 (2000).
Van Doorn et al., Quantitative Multiplex Detection of Plant Pathogens Using a Novel Ligation Probe-Based System coupled with Universal, High-Throughput Real-Time PCR on OpernArrays(TM), BMC Genomics 8(1): 1-14 (2007).
Vasiliskov, A.V. et al., Fabrication of microarray of gel-immobilized compounds on a chip by copolymerization, Biotechniques 27(3):592-606 (1999).
Wang et al., A model for Joule heating-induced dispersion in microchip electrophoresis, Lab Chip, 4(6):625-31 (2004).
Wang et al., Direct and sensitive miRNA profiling from low-input total RNA, RNA 13(1):151-9 (2007).
Watson et al., Cystic fibrosis population carrier screening: 2004 revision of American College of Medical Genetics mutation panel, Genet. Med. 6(5):387-91 (2004).
Wessensteiner et al., PCR Technology: Current Innovations (2007).
Wolf et al., Rapid hybridization kinetics of Dna attached to submicron latex particles, Nucleic Acids Research, 15; 2911-26 (1987).
Written Opinion for PCT/US2006/041668, dated Jun. 18, 2007, 9 pages.
Written Opinion for PCT/US2007/080426, dated Sep. 30, 2008, 8 pages.
Written Opinion for PCT/US2009/66778, dated on Jan. 13, 2010, 9 pages.
Written Opinion for PCT/US2011/039529, dated Feb. 9, 2012, 5 pages.
Written Opinion for PCT/US2011/39531, dated Feb. 23, 2012, 8 pages.
Written Opinion for PCT/US2013/029854, dated Jul. 4, 2013, 8 pages.
Xu, H. et al., Multiplexed SNP genotyping using the Qbead system: a quantum dot-encoded microsphere-based assay, Nucleic Acids Res. 31(8):e43 (2003).
Yang, A. et al., Hydrodynamic focusing investigation in a microflow cytometer, Biomed. Microdevices 9(2):113-22 (2007).
Zhao, X.W. et al., Uniformly Colorized Beads for Multiplex Immunoassay, Chem. Mater. 18(9):2443-49 (2006).
Zhi, Z. Let al., Micromachining microcarrier-based biomolecular encoding for miniaturized and multiplexed immunoassay, Anal. Chem. 75(16):4125-31 (2003).
Zhu et al., High-Sensitivity Capillary Electrophoresis of Double-Stranded DNA Fragments Using Monomeric and Dimeric Fluorescent Intercalating Dyes, Anal. Chem., 66; 1941-8 (1994).
Extended European Search Report for EP Application 11793064.4, 3 pages (Oct. 9, 2013).
He, B. et al., Nanowire sensors for multiplexed detection of biomolecules, Current Opinion in Chemical Biology, Current Biology Ltd., London, GB, 12(5): 522-528 (2008).
International Search Report for PCT/US2014/035578, 3 pages (Sep. 4, 2014).
Meade, S. et al., Multiplexed DNA Detection Using Spectrally Encoded Porous SiO 2 Photonic Crystal Particles, Analytical Chemistry, 81(7): 2618-2625 (2009).
Written Opinion for PCT/US2014/035578, 4 pages (Sep. 4, 2014).

* cited by examiner

Traditional Beads

Particle Design

Code, FL1 and FL3
Bound Target, FL2

Flow and Detection Setup

Multi-Event Particles

Codes, FL1-FL3
Bound Target, FL2

RAW Signal from PMTs

Processed Events to PC

| Event # | SSC-H | FL1-H | FL2-H | FL3-H | width |
|---|---|---|---|---|---|
| 1 | 85 | 48 | 94 | 38 | 12 |
| 2 | 79 | 91 | 35 | 84 | 14 |
| 3 | 88 | 72 | 31 | 82 | 11 |
| 4 | 94 | 36 | 89 | 93 | 13 |
| 5 | 76 | 84 | 62 | 37 | 14 |

| | Event # | SSC-H | FL1-H | FL2-H | FL3-H | width |
|---|---|---|---|---|---|---|
| particle #1 | 1 | 84 | 67 | 32 | 92 | 20 |
| | 2 | 85 | 2 | 94 | 2 | 18 |
| | 3 | 79 | 41 | 31 | 89 | 38 |
| particle #2 | 4 | 78 | 65 | 28 | 88 | 40 |
| | 5 | 81 | 1 | 76 | 1 | 17 |
| | 6 | 82 | 89 | 92 | 32 | 19 |

SCANNING MULTIFUNCTIONAL PARTICLES

RELATED REFERENCES

This application is a national filing under 35 U.S.C. § 371 of International Application No. PCT/US2011/39529 (PCT Publication No. WO 2011/156432), filed Jun. 7, 2011, which claims priority to U.S. provisional patent applications Ser. No. 61/352,018, filed Jun. 7, 2010, Ser. No. 61/365,738, filed Jul. 19, 2010, and Ser. No. 61/387,958, filed Sep. 29, 2010, the entire contents of which are herein incorporated by reference.

BACKGROUND

In biological, clinical and diagnostic research the need exists to identify a set of different biomolecules that might be present in the same sample, at a specific point in time. A typical solution to multiplexed detection is to mix a sample with encoded particles, each of which is functionalized with a probe that will recognize a specific target, and then analyze results from each of those particles. For this method to work reliably, it is important to (1) encode each particle so it can be reliably identified and to (2) quantify the amount of target bound to each particle. An example of such solution relies on color-coded particles that are interrogated by scanning them in a flow cytometer. In this approach, encoding is achieved by using precisely-controlled levels of various fluorochromes embedded in the particles, while target quantification is achieved by measuring the fluorescence intensity of a fluorophore bound to the target, which is in turn bound to the particle's surface. In this method, code identification and target quantification are performed contemporaneously. In other words, both the encoding and the target-bound dyes are located in the same place, so their signals need to be de-convoluted by sophisticated optical or electronic methods. For this reason, higher multiplexing requires more expensive equipment. Therefore, there is a need in this industry for robust and inexpensive methods for multiplexed analysis.

SUMMARY

The present invention provides, among other things, improved methods and systems for multiplexed detection and/or quantification of target analytes by scanning multifunctional particles (or other objects) using simple, inexpensive or portable detection systems such as standard flow cytometers. The present invention is, in part, based on the discovery that objects such as particles may be engineered to behave like a series of cells that flow past the cytometer interrogation zone. For example, objects (e.g., particles) may be created to have multiple functional regions (e.g., code region(s) and target region(s)) that are spatially separated. Each functional region can be interrogated at a different time, while the object (e.g., particle) is flowing through the illuminating laser beam of a flow cytometer. Standard flow cytometry data may then be decoded to reconstruct the particles, their corresponding functional regions and the bound target analytes. This approach provides for much higher levels of multiplexing, greater encoding flexibility, more accurate target quantification, and the ability to interrogate several targets per particle.

Thus, in one aspect, the present invention provides a method for characterizing multifunctional objects comprising (a) interrogating a plurality of objects, wherein each individual object comprises one or more interrogation regions detectable as a sequence of events; (b) recording multiple events, wherein each individual event corresponds to each individual interrogation region detectable above a pre-determined triggering threshold; (c) grouping the recorded multiple events, and (d) characterizing the plurality of objects based on the grouped events.

In some embodiments, suitable objects are selected from the group consisting of particles, beads, phages, macromolecules, cells, micro-organisms, and combination thereof. In some embodiments, suitable objects are particles. In some embodiments, suitable objects are macromolecules selected from proteins, DNAs and/or RNAs. In some embodiments, suitable objects are micro-organisms selected from *C. elegans*, bacteria, yeast, and/or fungi.

In some embodiments, the multiple events are recorded non-contemporaneously. In some embodiments, the multiple events are recorded contemporaneously. In some embodiments, the events are recorded using a flow cytometer. In some embodiments, the objects are illuminated with one or more lasers. In some embodiments, the events comprise fluorescent and/or scatter signal.

In some embodiments, each individual object comprises separate probe and coding regions. In some embodiments, each individual object comprises two coding regions and one probe region separated by inert spacers. In some embodiments, the probe region contains DNA, RNA, proteins, and/or cells. In some embodiments, the probe region comprises a generic linking chemistry. In some embodiments, the probe region contains a single-stranded polynucleotide template containing capturing sequence specific for a target nucleic acid and an adjacent adapter sequence for binding a universal adapter such that a binding of both the target nucleic acid and the universal adapter (e.g., detectablely labeled) to the polynucleotide template is detectable via post-hybridization labeling.

In some embodiments, the coding and/or probe regions are labeled with fluorophores. In some embodiments, the fluorescence levels are used to characterize the objects. In some embodiments, the level of one detectable signal is used to scale the magnitude of another. In some embodiments, the signal used for scaling is obtained from the same excitation source as the signal being scaled. In some embodiments, the widths of the coding and/or probe regions are used to characterize the objects.

In some embodiments, the interrogation regions contain entities that cause scatter such that a scatter signal is used to trigger event recording. In some embodiments, the interrogation regions contain fluorescent entities and fluorescence is used to trigger event recording. In some embodiments, the interrogation regions comprise coding and/or probe regions.

In some embodiments, the interrogating step comprises a step of flowing the plurality of objects through a detection zone. In some embodiments, the interrogating step comprises a step of detecting the plurality of objects in a static manner.

In some embodiments, the events are grouped based on spatial and temporal-proximity. In some embodiments, the events are grouped based on patterns of measured properties for each event. In some embodiments, the grouping step comprises statistical analysis.

In some embodiments, the characterizing step comprises determining the identity of individual objects. In some embodiments, the characterizing step comprises quantifying one or more objects. In some embodiments, the characterizing step comprises comparing the grouped events to a functional table indicative of identities of individual particles.

In another aspect, the present invention provides a method for detecting multiple analytes in a sample comprising (a) mixing a plurality of multifunctional particles with a sample containing one or more target analytes, wherein each individual particle comprises one or more interrogation regions detectable as a sequence of events and one or more probes specific for the one or more target analytes; (b) interrogating the plurality of multifunctional particles; (c) recording multiple events wherein each individual event corresponds to each individual interrogation region detectable above a pre-determined triggering threshold, and wherein the binding between a probe and its corresponding target analyte alters corresponding event associated with the interrogation region containing the probe; (d) grouping the events for each particle; and (e) detecting the presence of the one or more target analytes by detecting altered events based on the grouping result from step (d) as compared to a control.

In some embodiments, in step (c), the binding between the probe and its corresponding target permits post-binding labeling with fluorescent signals thereby altering corresponding event associated with the interrogation region containing the probe. In some embodiments, the method further comprises associating a code to each particle using events associated with coding regions. In some embodiments, the code for each particle is determined in part by event width, fluorescence or scatter height, fluorescence or scatter area, or any combination thereof.

In some embodiments, the method further comprises quantifying the amount of bound target analyte. In some embodiments, the quantifying step comprises determining fluorescence levels in events associated with interrogation regions containing the corresponding probe. In some embodiments, the amount of bound target analyte is determined in part by event width, fluorescence or scatter height, fluorescence or scatter area, or any combination thereof.

In some embodiments, the interrogating step comprises flowing the plurality of multifunctional particles past a detection zone. In some embodiments, the recording step comprises recording temporal signals from the one or more interrogation regions. In some embodiments, the temporal signals comprise fluorescent and/or scatter signals. In some embodiments, the method further comprises processing the temporal signals to identify characteristic signal features indicative of individual particles. In some embodiments, the processing step comprises identifying coding and probe regions of particles based on the characteristic features. In some embodiments, the process step further comprises categorizing the particles based on the characteristic features indicative of coding regions.

In yet another aspect, the present invention provides a method for characterizing multifunctional objects comprising (a) interrogating a plurality of objects, wherein each individual object comprises one or more interrogation regions, each interrogation region characterized with a detectable signal pattern once interrogated; (b) recording detectable signals; (c) grouping the recorded detectable signals, and (d) characterizing the plurality of objects based on the grouping results from step (c). In some embodiments, the detectable signal pattern is continuous. In some embodiments, the detectable signals are selected from fluorescent and/or scatter signals. In some embodiments, the signals are grouped based on spatial and temporal-proximity. in some embodiments, the signals are grouped based on patterns of fluorescent and/or scatter signals. In some embodiments, the interrogating step comprises a step of flowing the plurality of objects through a detection zone.

In still another aspect, the present invention provides a method for detecting multiple analytes in a sample comprising (a) mixing a plurality of multifunctional particles with a sample containing one or more target analytes, wherein each individual particle comprises one or more interrogation regions, each interrogation region characterized with a detectable signal pattern once interrogated, and one or more probes specific for the one or more target analytes; (b) interrogating the plurality of multifunctional particles; (c) recording detectable signals wherein the binding between a probe and its corresponding target analyte alters corresponding detectable signal pattern associated with the interrogation region containing the probe; (d) grouping the detectable signals for each particle; (e) detecting the presence of the one or more target analytes by detecting altered signal pattern based on the grouping result from step (d) as compared to a control. In some embodiments, the detectable signal pattern is continuous.

Among other things, the present invention provides various particles described herein. In some embodiments, the present invention provides particles comprising multiple interrogation regions, wherein the particle is detectable by a flow cytometer and wherein the multiple interrogation regions are detectable as a sequence of events.

In some embodiments, the present invention provides a particle comprising one or more interrogation regions, wherein the particle is detectable by a flow cytometer and wherein each individual interrogation region is characterized with a detectable signal pattern once interrogated. In some embodiments, the detectable signal pattern is continuous.

In various embodiments, the multiple interrogation regions are distinct regions separated by undetectable spacers. In various embodiments, the multiple interrogation regions comprise regions loaded with probes. In various embodiments, the multiple interrogation regions comprise encoded regions. In various embodiments, the encoded regions are loaded with nanoparticles or microparticles. In various embodiments, the encoded regions are loaded with a fluorochrome. In various embodiments, the multiple interrogation regions comprise a series of bands.

In various embodiments, a particle according to the invention has an aspect ratio greater than one (e.g., great than 1.0, 1.2, 1.4, 1.5, 1.6, 1.8, 2.0, 2.5). In various embodiments, a particle according to the invention has a morphology that facilitates its self-alignment in flow. In various embodiments, a particle of the invention is bar-shaped or rod-shaped. In various embodiments, a particle of the invention is made from a polymer. In various embodiments, suitable polymer contains PEG.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

BRIEF DESCRIPTION OF THE FIGURES

The drawings are for illustration purposes only, not for limitation.

Multifunctional particles bear functional regions that can be doped with triggering entities (that cause scatter for instance) and single particles are recorded as multiple events. By analyzing the shape and time-sequence of these events, and by appropriately designing particles, one can reconstruct from this series of events, which ones belong in the same particle.

Figure 15:
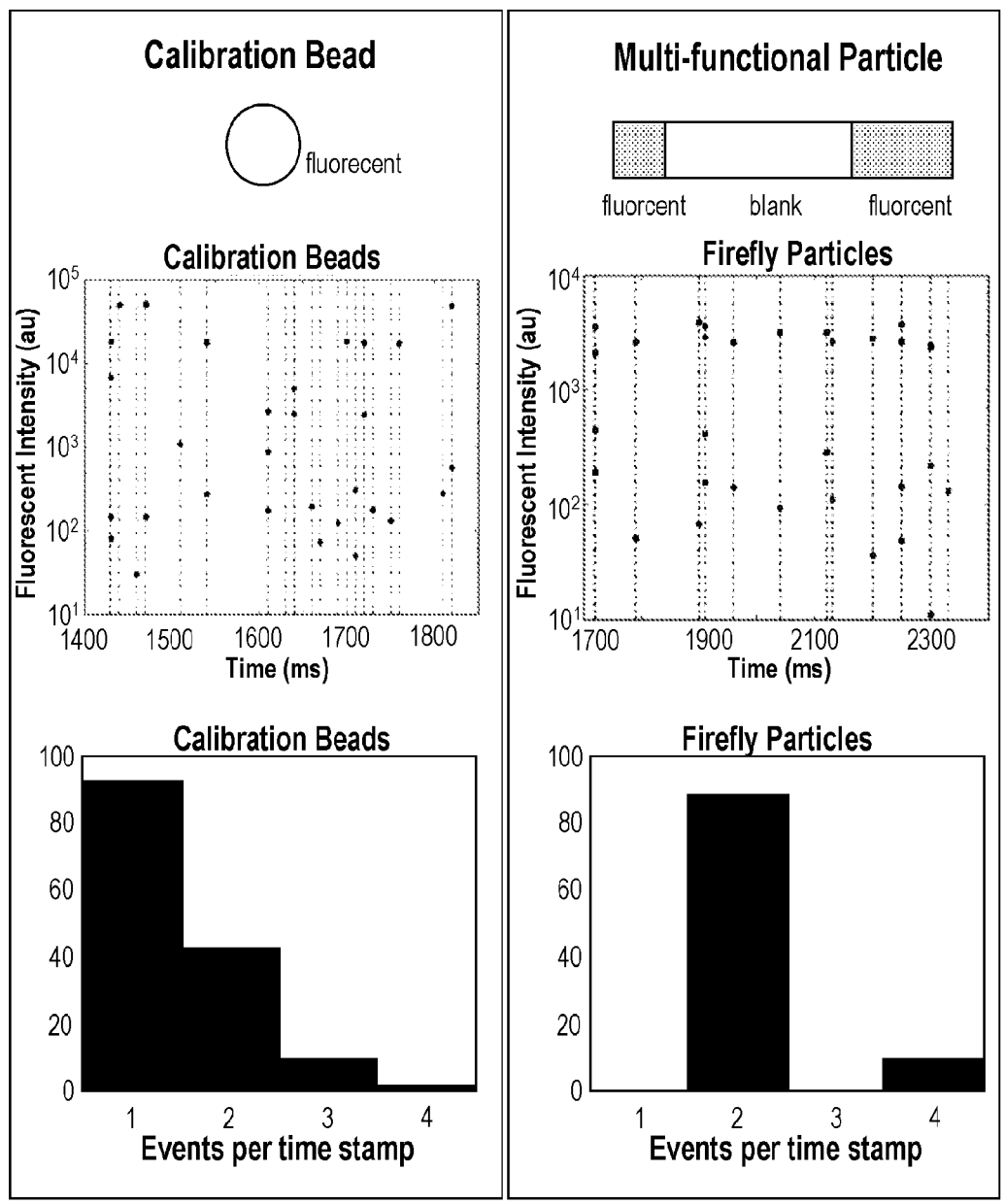

FIG. 15 illustrates exemplary comparison of scanning fluorescent calibration beads versus multifunctional particles. Shown is particle design (top), recorded events at each 1 ms timestamp (middle), and distribution of events per timestamp for timestamps where at least one event was recorded for calibration beads and multi-functional particles with two fluorescent regions (bottom).

Figure 16:
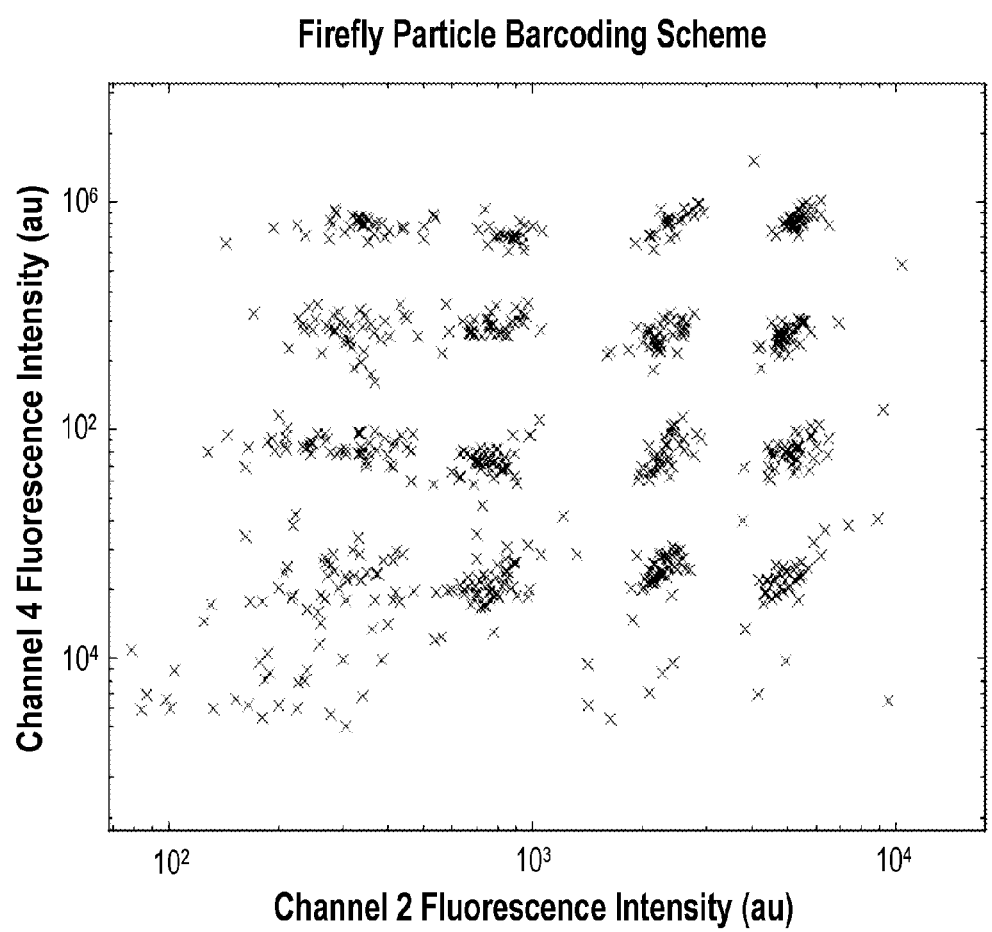

FIG. 16 illustrates an exemplary fluorescence scatter plot for multifunctional particles with a single code region functionalized with four distinct levels of Cy3 (shows in Channel 2) and Cy5 (Channel 4).

Figure 17:
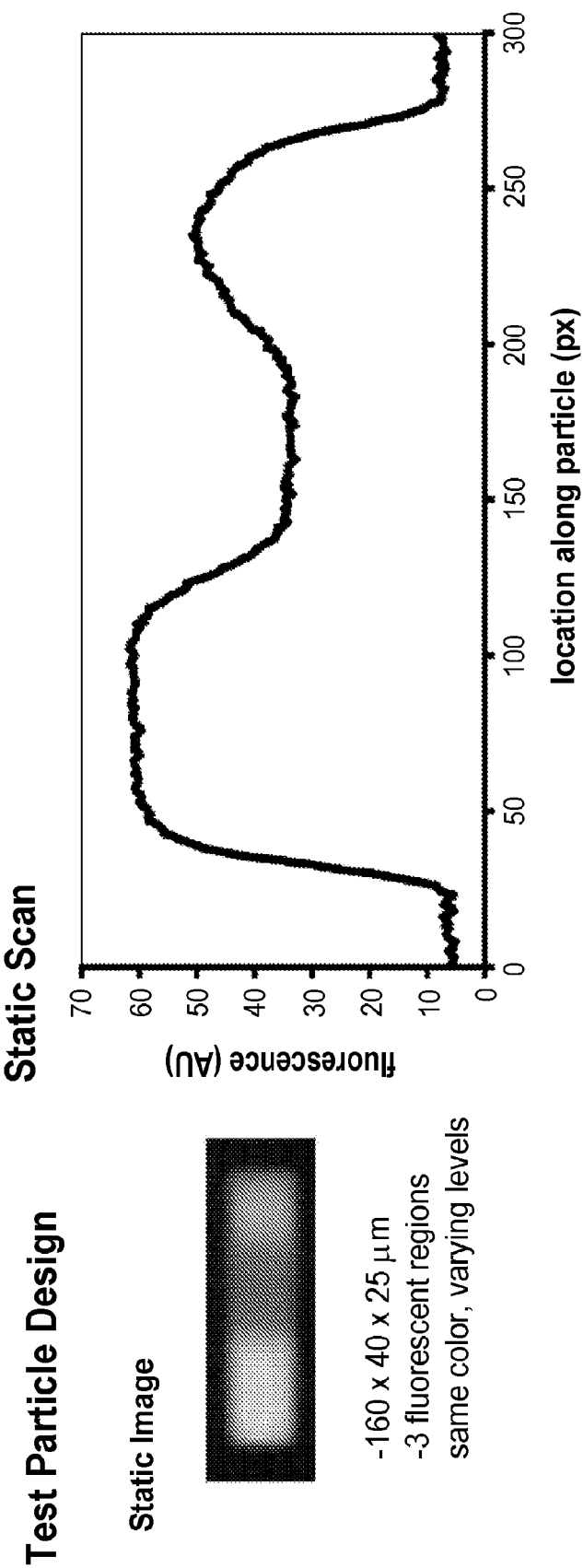

FIG. 17 illustrates exemplary design and use of a standard set of test particles to assess alignment and consistency of scan.

Figure 18:
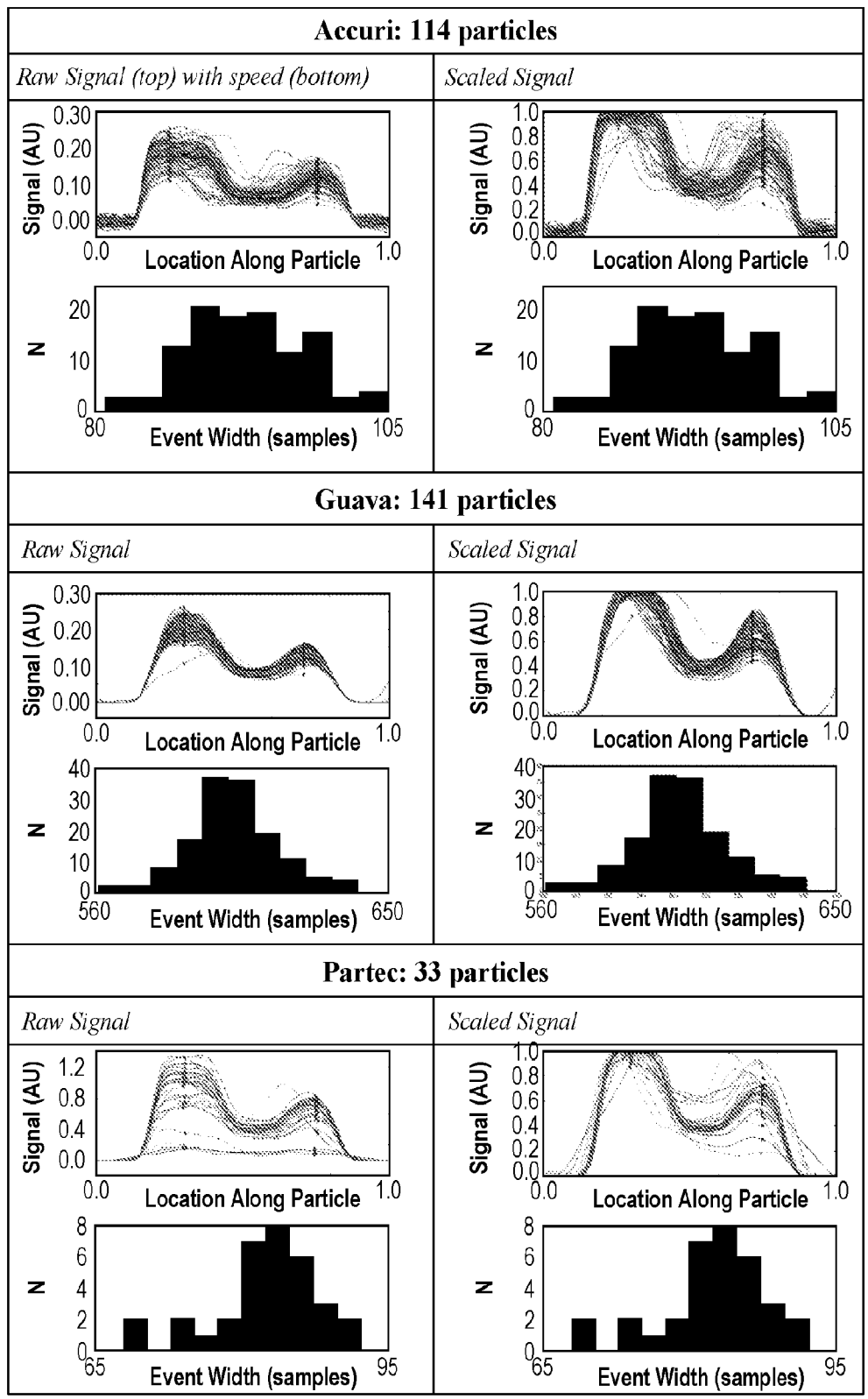

FIG. 18 illustrates exemplary results of a standard set of test particles to assess alignment and consistency of scan.

Figure 19:
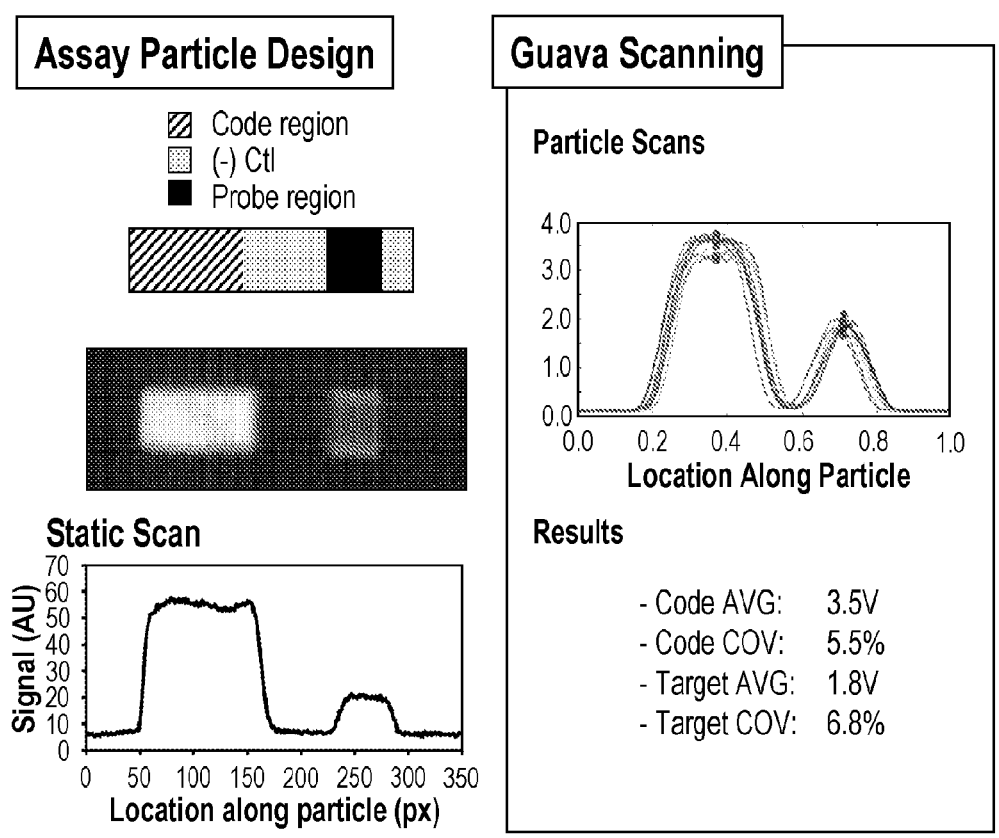

FIG. 19 illustrates exemplary results of nucleic acid detection using particles with a single, wide fluorescent region to represent a "barcode" and a narrow probe region.

Figure 20:
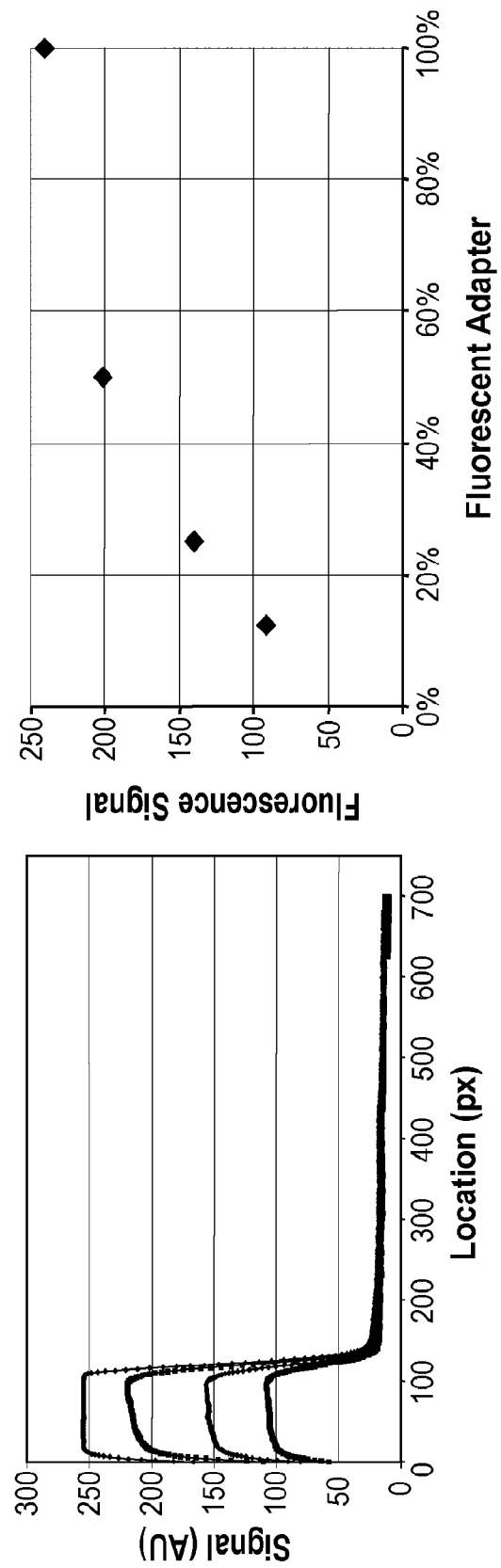

FIG. 20 illustrates exemplary results of average scans along the particle length (averaging over half of the width). The bottom signal, second lowest signal, second highest signal, and highest signal correspond to 12.5%, 25%, 50%, and 100% fluorescent ligation mix solutions, respectively.

Figure 21:
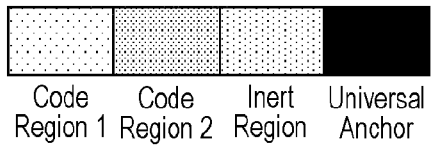
Figure 21:
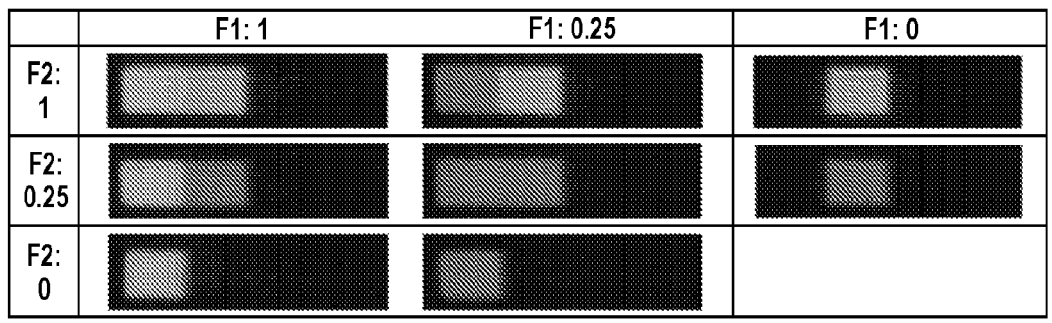
Figure 21:
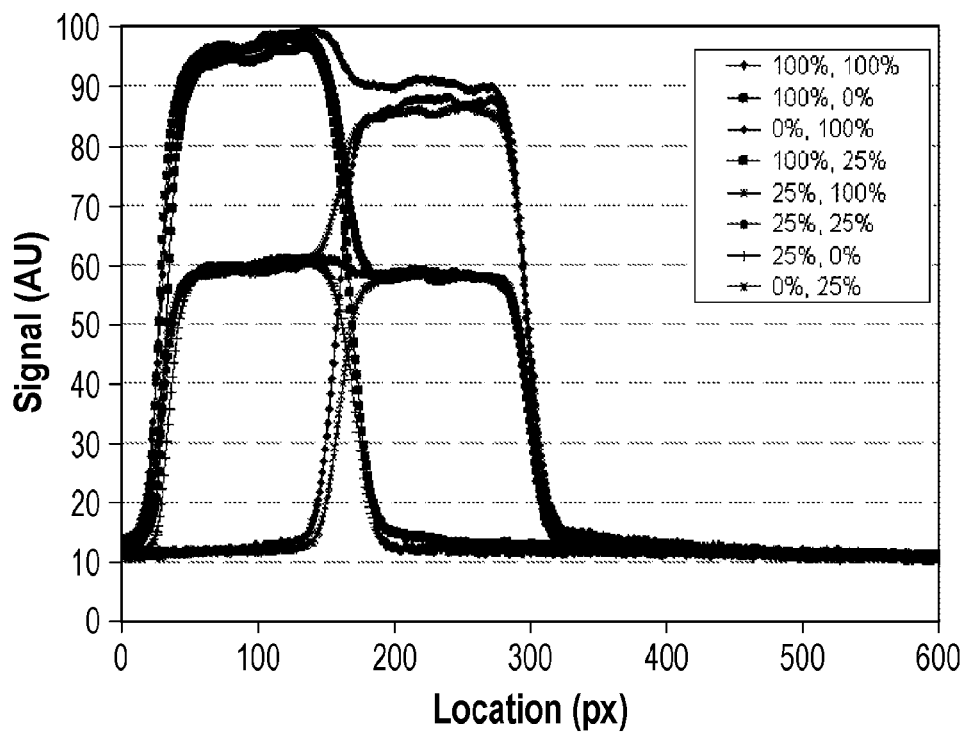

FIG. 21 illustrates examples of a) particle design and images for each mixture; and b) average scans over 5 particles for each mixture. (1 μm~3.3 px, numbers in legend represent F1 and F2.)

Figure 22:
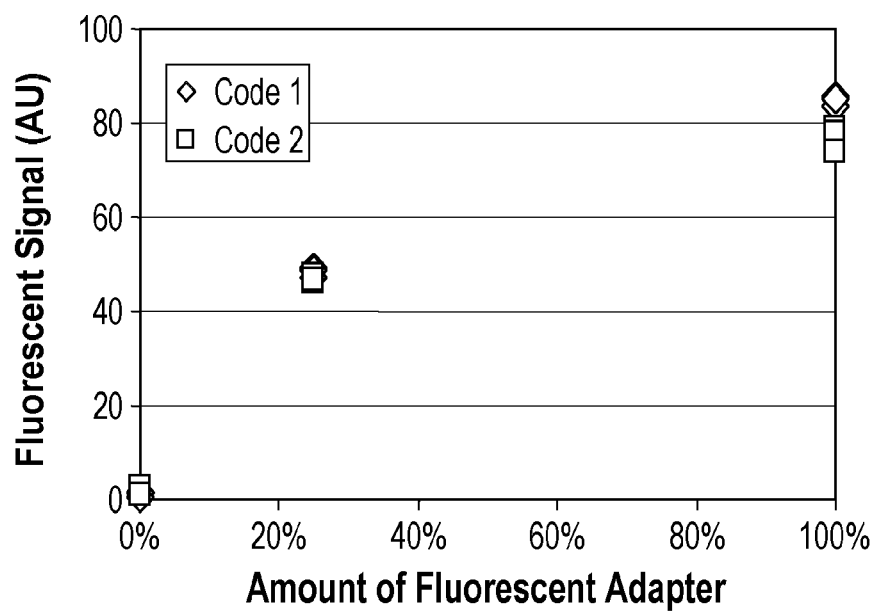

FIG. 22 illustrates exemplary results of measured fluorescence versus the adapter amount from each ligation mix.

Figure 23:
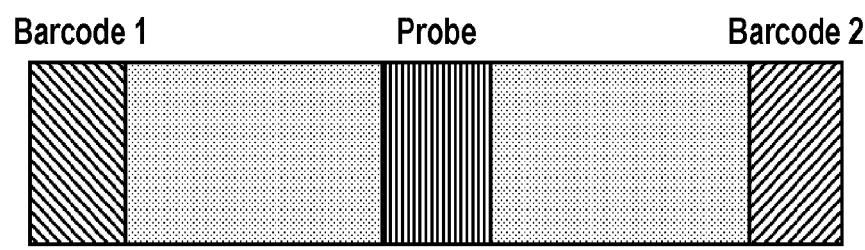

FIG. 23 illustrates exemplary general particle design for universal encoding.

Figure 24:
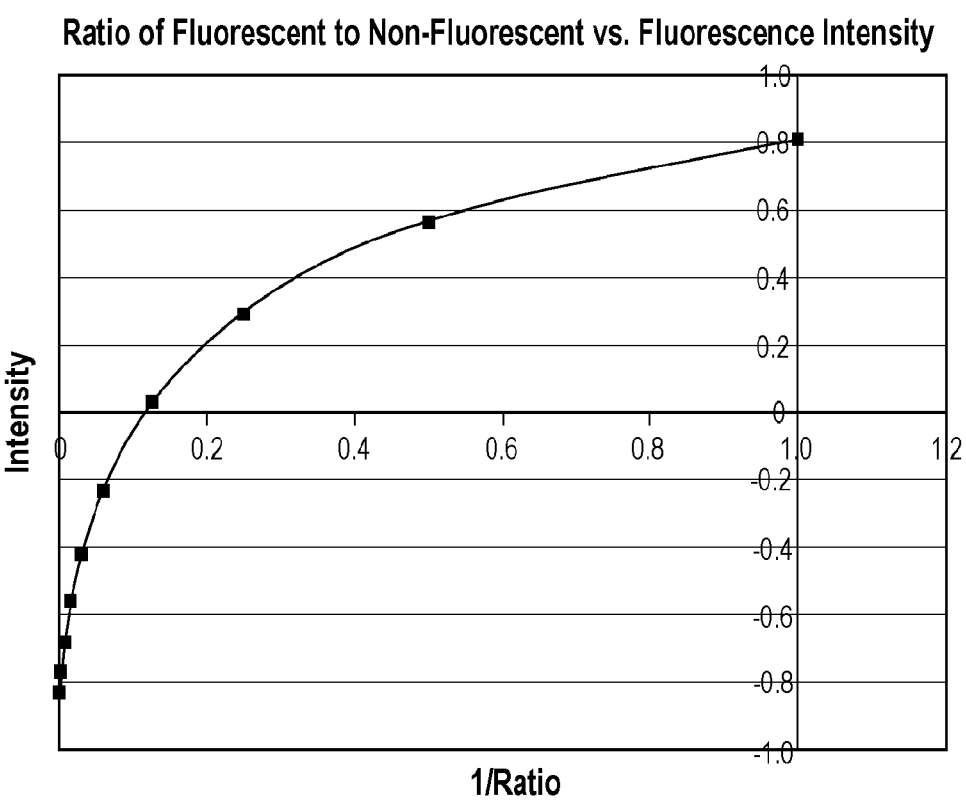

FIG. 24 illustrates exemplary fluorescent signal obtained in Barcode 1 region with varying ratios of fluorescent (Cy3) to non-fluorescent adapter.

Figure 25:
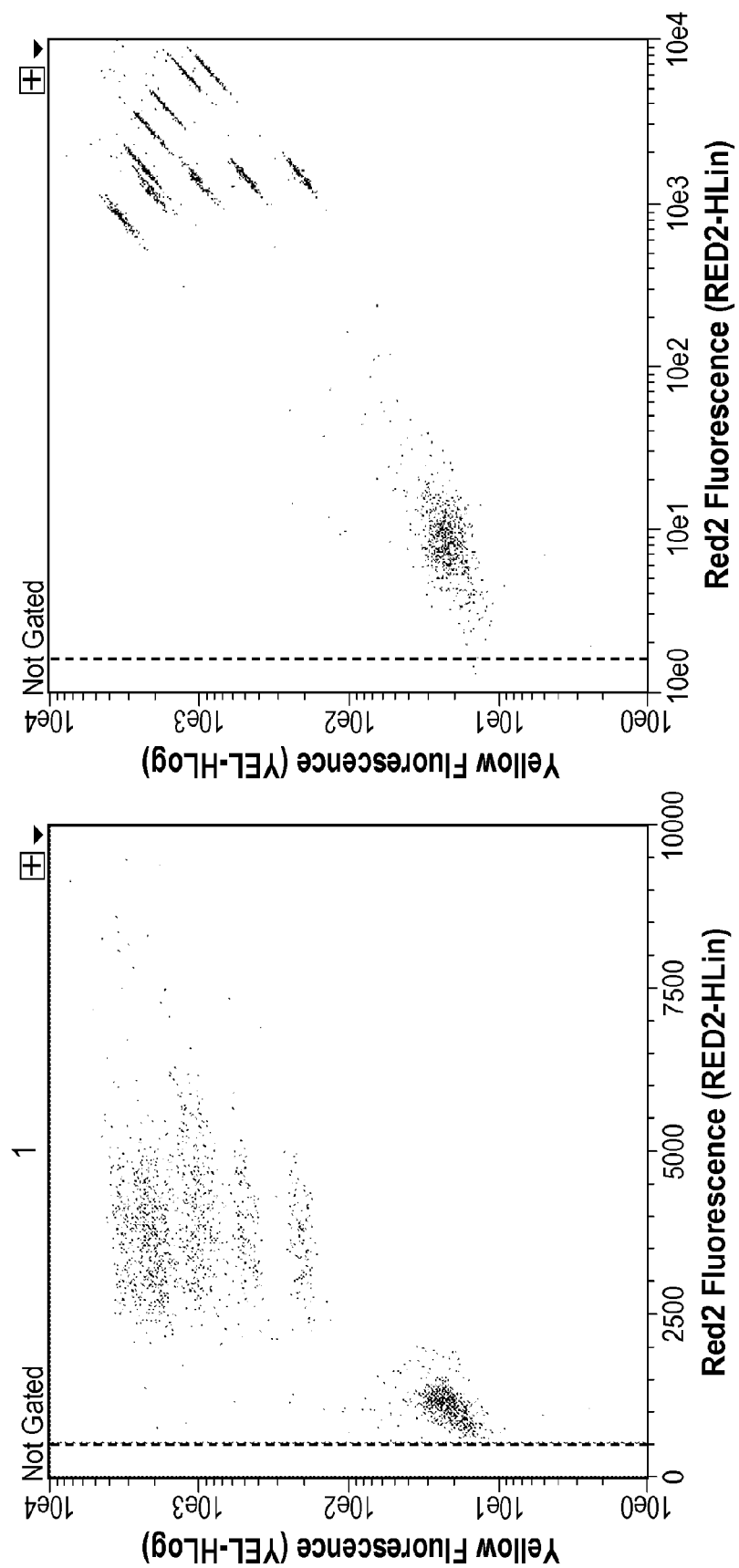

FIG. 25 illustrates exemplary plot of events associated with barcoded gel particles. Shown on the left is a plot of YEL fluorescence (used for barcoding) versus RED2 fluorescence (used for triggering) and on the right YEL fluorescence (used for barcoding) versus GRN fluorescence (used for orientation).

Figure 26:
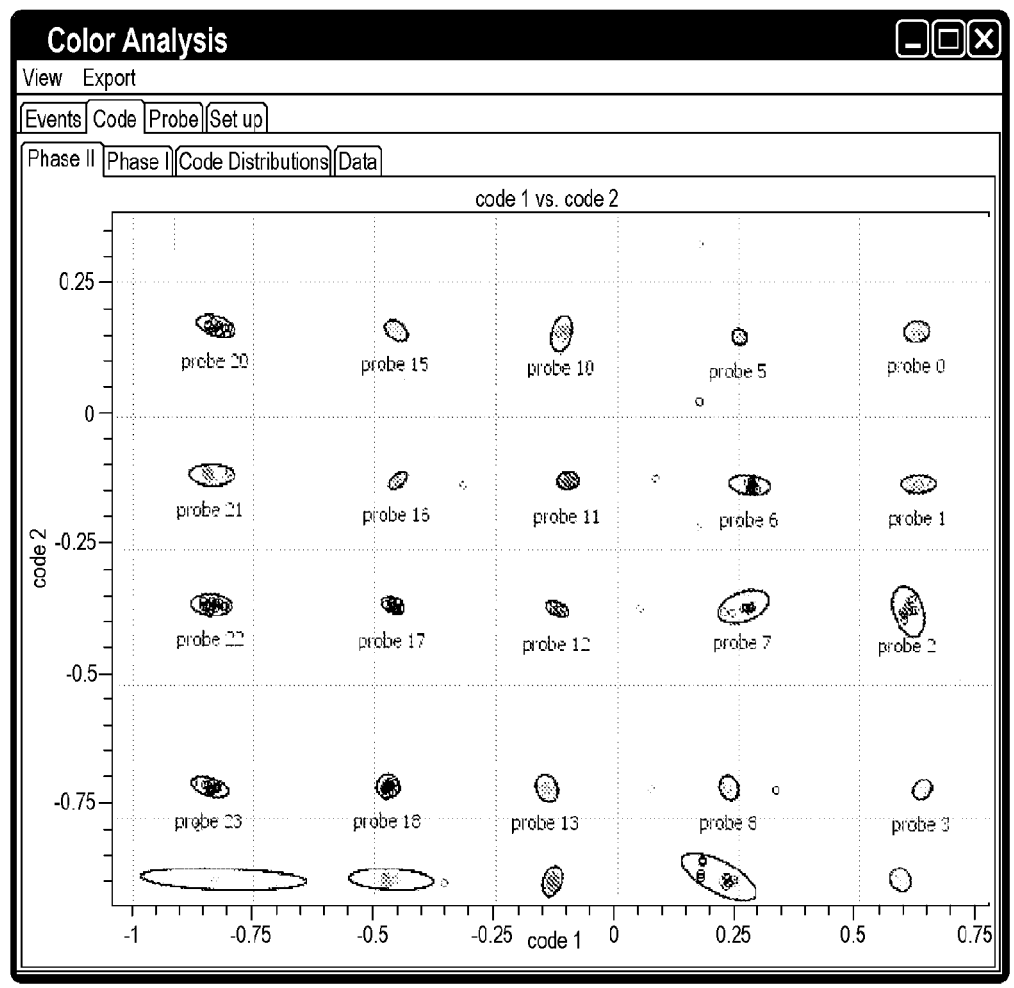

FIG. 26 illustrates exemplary demonstration of 25-plex encoding using 5 unique levels of YEL fluorescence on both Barcode 1 and Barcode 2 regions of encoded particles. These data have been reconstructed from raw events saved in a FCS file from the Guava software.

Figure 27:
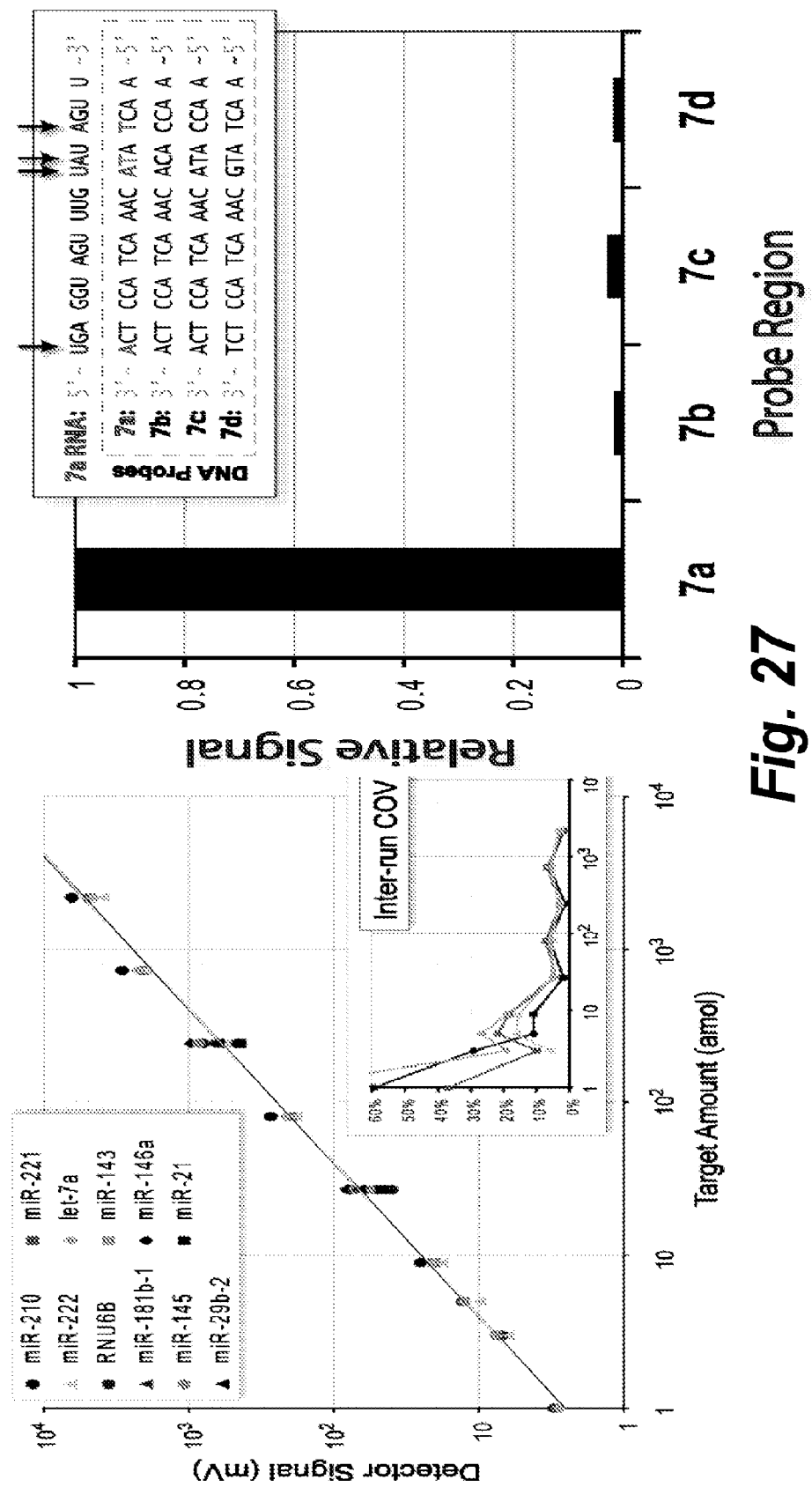

FIG. 27 illustrates exemplary demonstration of attomole sensitivity (left), >3 log dynamic range (left), and single-nucleotide specificity (right) using Firefly BioWorks' custom assay for microRNA targets. We used Firefly's 3-hour assay (total RNA to results) to detect dilutions of eleven microRNA targets spiked into 250 ng of *E. coli* total RNA, reporting the average detector signal versus spike-in amount with inter-run COV (inset). Specificity was assessed by spiking let-7a RNA target samples containing particles bearing probes for let-7a, 7b, 7c, and 7d—each which varied by only one or two nucleotides (right).

Figure 28:
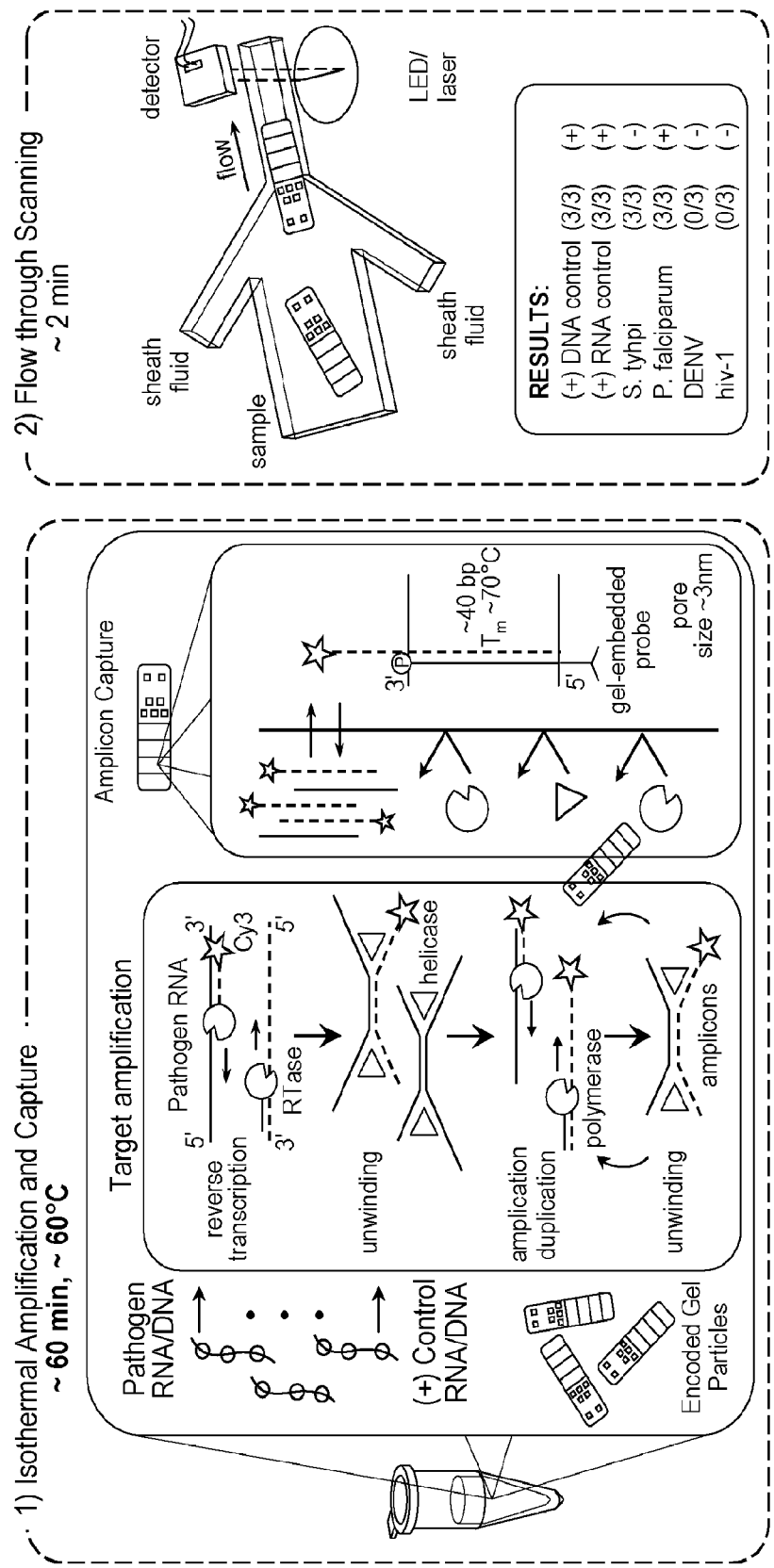

FIG. 28 illustrates exemplary multiplexed isothermal amplification and capture assay for panel-based pathogen detection. Fluorescent amplicons generated using reverse transcription helicase-dependent amplification (RT-HDA) will be captured on encoded hydrogel particles in a single step. Each particle, bearing probe regions for three signatures of a given species and porosity-tuned to exclude helicase penetration, will immediately be scanned in a microdevice without the need for rinsing. The high sensitivity of encoded gel particles and two-levels of specificity (amplification and hybridization) will mitigate false-positive or negative reads.

Figure 29:
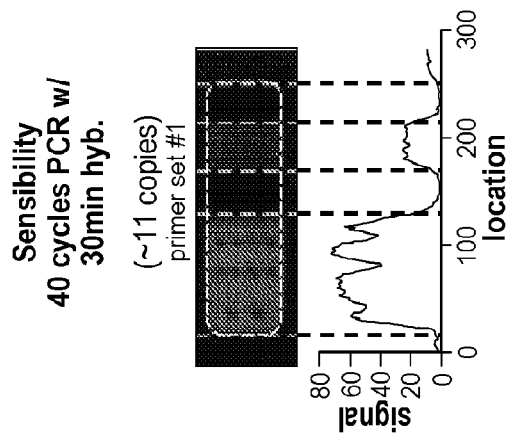
Figure 29:
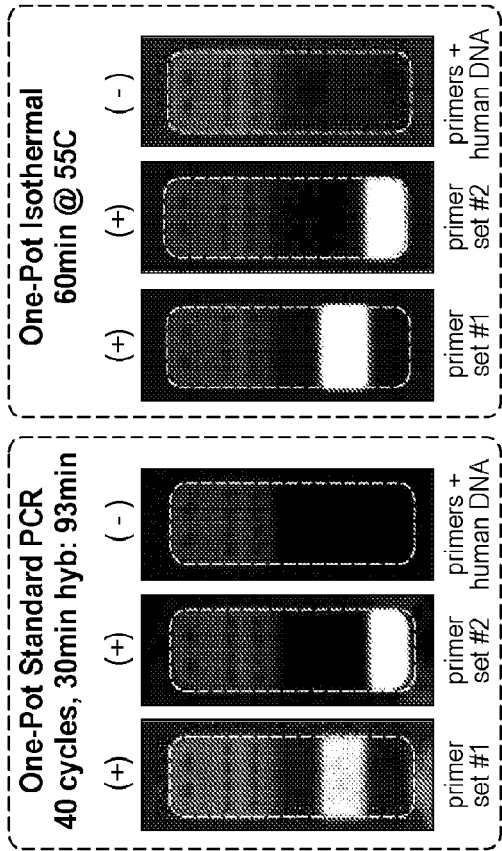
Figure 29:
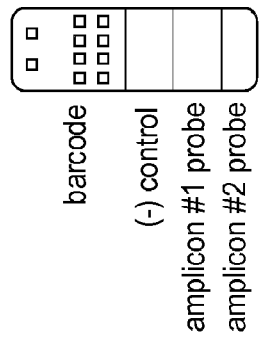

FIG. 29 illustrates exemplary proof-of-concept one-pot assays using standard PCR and isothermal amplification, demonstrating specificity of amplification and sensitive detection of ~11 template copies. We assessed the specificity of amplification for two targeted regions of λ-phage DNA, using a one-pot reaction with probes designed against the amplicons generated by two separate primer sets. Template λ-phage was spiked into (+) samples at ~11,000 copies for specificity tests, though we were also able to detect amplified product with only ~11 copies present (right). For specificity against human genomic DNA, we spiked ~11,000 copies of human genomic DNA into the reaction with no λ-phage present.

Figure 30:
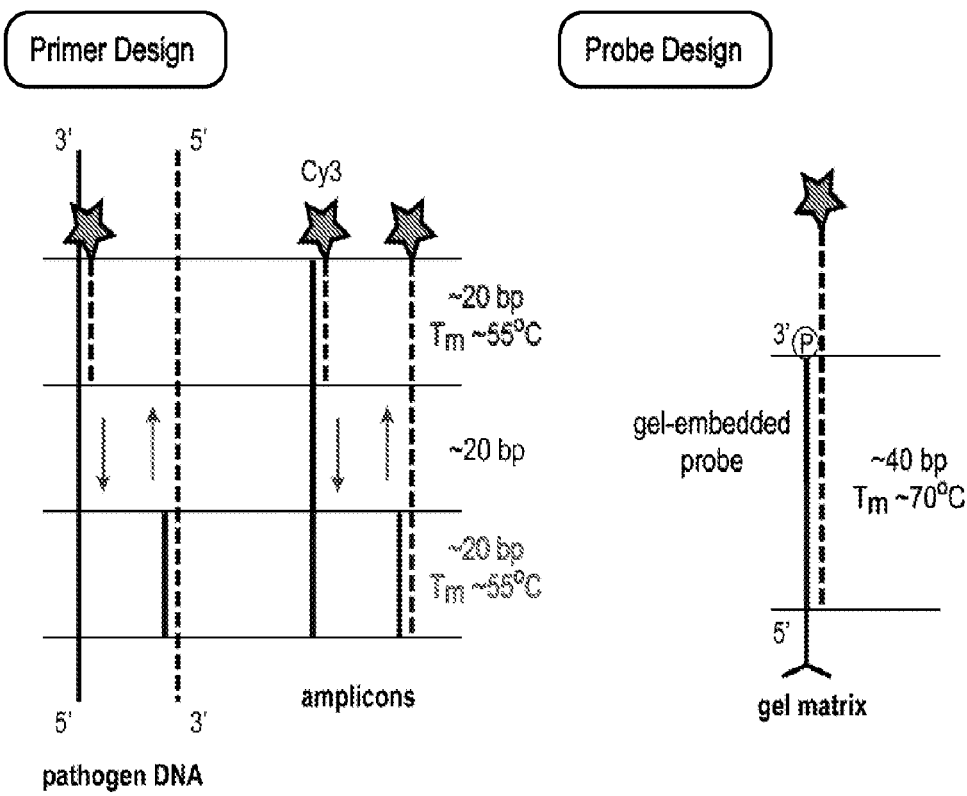

FIG. 30 illustrates exemplary amplification primer (left) and amplicon probe (right) design for multiplexed detection assays. Forward primers will have a single Cy3 fluorophore. Probes will be designed to have a $T_m$ than primers and will be 3' phosphorylated to avoid incidental 3'-extension.

Figure 31:
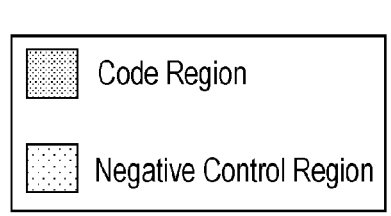
Figure 31:
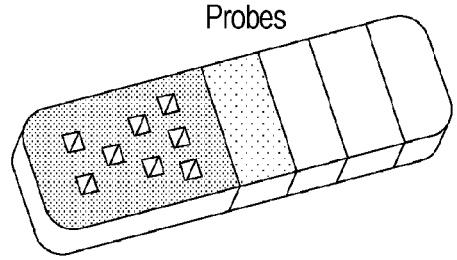
Figure 31:
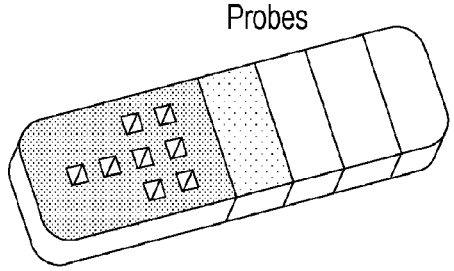
Figure 31:
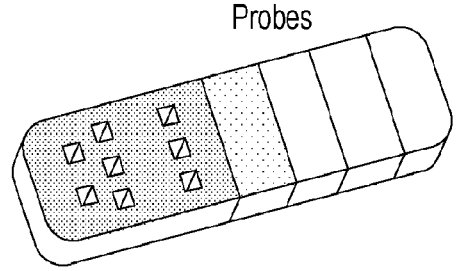

FIG. 31 illustrates exemplary design of barcoded gel particles for species-specific amplicon quantification.

DEFINITIONS

In order for the present invention to be more readily understood, certain terms are first defined below. Additional definitions for the following terms and other terms are set forth throughout the specification.

In order for the present invention to be more readily understood, certain terms are first defined below. Additional definitions for the following terms and other terms are set forth throughout the specification.

"Adjacent": As used herein, the term "adjacent" means "next to," "contiguous," "adjoining," "abutting" or having a common boundary.

"Analyte": As used herein, the term "analyte" broadly refers to any substance to be analyzed, detected, measured, or quantified. Examples of analytes include, but are not limited to, proteins, peptides, hormones, haptens, antigens, antibodies, receptors, enzymes, nucleic acids, polysaccharides, chemicals, polymers, pathogens, toxins, organic drugs, inorganic drugs, cells, tissues, microorganisms, viruses, bacteria, fungi, algae, parasites, allergens, pollutants, and combinations thereof.

"Associated": As used herein, the terms "associated", "conjugated", "linked", "attached", "complexed", and "tethered," and grammatical equivalents, typically refer to two or more moieties connected with one another, either directly or indirectly (e.g., via one or more additional moieties that serve as a linking agent), to form a structure that is sufficiently stable so that the moieties remain connected under the conditions in which the structure is used, e.g., physiological conditions. In some embodiments, the moieties are attached to one another by one or more covalent bonds. In some embodiments, the moieties are attached to one another by a mechanism that involves specific (but non-covalent) binding (e.g. streptavidin/avidin interactions, antibody/antigen interactions, etc.). Alternatively or additionally, a sufficient number of weaker interactions (non-covalent) can provide sufficient stability for moieties to remain connected. Exemplary non-covalent interactions include, but are not limited to, affinity interactions, metal coordination, physical adsorption, host-guest interactions, hydrophobic interactions, pi stacking interactions, hydrogen bonding interactions, van der Waals interactions, magnetic interactions, electrostatic interactions, dipole-dipole interactions, etc.

"Biomolecules": The term "biomolecules", as used herein, refers to molecules (e.g., proteins, amino acids, peptides, polynucleotides, nucleotides, carbohydrates, sugars, lipids, nucleoproteins, glycoproteins, lipoproteins, steroids, etc.) whether naturally-occurring or artificially created (e.g., by synthetic or recombinant methods) that are commonly found in cells and tissues. Specific classes of biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

"Biocompatible": The term "biocompatible", as used herein is intended to describe materials that do not elicit a substantial detrimental response in vivo. In some embodiments, a substance is considered to be "biocompatible" if its addition to cells in vitro or in vivo results in less than or equal to about 50%, about 45%, about 40%, about 35%, about 30%, about 25%, about 20%, about 15%, about 10%, about 5%, or less than about 5% cell death.

"Biodegradable": As used herein, the term "biodegradable" refers to substances that are degraded under physiological conditions. In some embodiments, a biodegradable substance is a substance that is broken down by cellular machinery. In some embodiments, a biodegradable substance is a substance that is broken down by chemical processes.

"Complement": As used herein, the terms "complement," "complementary" and "complementarity," refer to the pairing of nucleotide sequences according to Watson/Crick pairing rules. For example, a sequence 5'-GCGGTCCCA-3' has the complementary sequence of 5'-TGGGACCGC-3'. A complement sequence can also be a sequence of RNA complementary to the DNA sequence. Certain bases not commonly found in natural nucleic acids may be included in the complementary nucleic acids including, but not limited to, inosine, 7-deazaguanine, Locked Nucleic Acids (LNA), and Peptide Nucleic Acids (PNA). Complementary need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

"Contemporaneous" and "non-contemporaneous": As used herein, the terms "contemporaneous," "contemporaneously," or grammatical equivalents, mean that multiple events occur or happen at the same time without a detectable or identifiable sequential order. As used herein, the terms "non-contemporaneous," "non-contemporaneously," or grammatical equivalents, mean that multiple events occur or happen in a detectable or identifiable sequential order.

"Crude": As used herein, the term "crude," when used in connection with a biological sample, refers to a sample which is in a substantially unrefined state. For example, a crude sample can be cell lysates or biopsy tissue sample. A crude sample may exist in solution or as a dry preparation.

"Encoding region," "coding region," or "barcoded region": As used herein, the terms "encoding region," "coding region," "barcoded region", or grammatical equivalents, refer to a region on an object or substrate (e.g., particle) that can be used to identify the object or substrate (e.g., particle). These terms may be used inter-changeably. Typically, an encoding region of an object bears graphical and/or optical features associated with the identity of the object. Such graphical and/or optical features are also referred to as signature features of the object. In some embodiments, an encoding region of an object bears spatially patterned features (e.g., stripes with various shapes and/or dimensions, or a series of holes with various sizes) that give rise to variable fluorescent intensities (of one or multiple wavelengths). In some embodiments, an encoding region of an object bears various type and/or amount of fluorophores or other detectable moieties, in various spatial patterns, that give rise to variable fluorescent signals (e.g., different colors and/or intensities) in various patterns.

"Functionalization: As used herein, the term "functionalization" refers to any process of modifying a material by bringing physical, chemical or biological characteristics different from the ones originally found on the material. Typically, functionalization involves introducing functional groups to the material. As used herein, functional groups are specific groups of atoms within molecules that are responsible for the characteristic chemical reactions of those molecules. As used herein, functional groups include both chemical (e.g., ester, carboxylate, alkyl) and biological groups (e.g., adapter, or linker sequences).

"Hybridize": As used herein, the term "hybridize" or "hybridization" refers to a process where two complementary nucleic acid strands anneal to each other under appropriately stringent conditions. Oligonucleotides or probes suitable for hybridizations typically contain 10-100 nucleotides in length (e.g., 18-50, 12-70, 10-30, 10-24, 18-36 nucleotides in length). Nucleic acid hybridization techniques are well known in the art. See, e.g., Sambrook, et al., 1989, Molecular cloning: A Laboratory Manual, Second Edition, Cold Spring Harbor Press, Plainview, N.Y. Those skilled in the art understand how to estimate and adjust the stringency of hybridization conditions such that sequences having at least a desired level of complementary will stably hybridize, while those having lower complementary will not. For examples of hybridization conditions and parameters, see, e.g., Sambrook, et al., 1989, Molecular cloning: A Laboratory Manual, Second Edition, Cold Spring Harbor Press, Plainview, N.Y.; Ausubel, F. M. et al. 1994, Current Protocols in Molecular Biology. John Wiley & Sons, Secaucus, N.J.

"Hydrodynamic diameter": The term "hydrodynamic diameter", as used herein, generally refers to the effective diameter of a hydrated molecule (e.g., macromolecules, colloids, or particles) in solution, corresponding to the diameter of a sphere with equal mobility in solution. In some embodiments, a hydrodynamic diameter is used to describe the measured size of particles in solution. In certain embodiments, hydrodynamic diameter may be determined by dynamic light scattering size measurement. For example, Zetasizer Nano ZS instrument (Malvern) can be used to measure the hydrodynamic diameter of particles as demonstrated in the Example Section below.

"Inert region": As used herein, the terms "inert region," "inert spacer" or grammatical equivalents, when used in connection with a region on an object (e.g., particle), refer to a region that is not detectable above a pre-determined triggering threshold by a flow-through scanning device such as a flow cytometer. Typically, an inert region or spacer is a non-functionalized region. For example, an inert region is a region not loaded with probes or other detectable moieties.

"Interrogate": As used herein, the terms "interrogate," "interrogating," "interrogation" or grammatical equivalents, refer to a process of characterizing or examining to obtain data.

"Labeled": The terms "labeled" and "labeled with a detectable agent or moiety" are used herein interchangeably to specify that an entity (e.g., a nucleic acid probe, antibody, etc.) can be visualized, for example following binding to another entity (e.g., a nucleic acid, polypeptide, etc.). The detectable agent or moiety may be selected such that it generates a signal which can be measured and whose intensity is related to (e.g., proportional to) the amount of bound entity. A wide variety of systems for labeling and/or detecting proteins and peptides are known in the art. Labeled proteins and peptides can be prepared by incorporation of, or conjugation to, a label that is detectable by spectroscopic, photochemical, biochemical, immunochemical, electrical, optical, chemical or other means. A label or labeling moiety may be directly detectable (i.e., it does not require any further reaction or manipulation to be detectable, e.g., a fluorophore is directly detectable) or it may be indirectly detectable (i.e., it is made detectable through reaction or binding with another entity that is detectable, e.g., a hapten is detectable by immunostaining after reaction with an appropriate antibody comprising a reporter such as a fluorophore). Suitable detectable agents include, but are not limited to, radionucleotides, fluorophores, chemiluminescent agents, microparticles, enzymes, colorimetric labels, magnetic labels, haptens, molecular beacons, aptamer beacons, and the like.

"Monodisperse": As used herein, the terms "monodisperse" or "monosized" refer to a collection of objects that have substantially the same size and shape when in the context of particles, and substantially the same mass in the context of polymers. Conversely, a collection of objects that have an inconsistent size, shape and mass distribution are called polydisperse. Monodisperse particles are typically synthesized through the use of template-based synthesis.

"Object" or "substrate": As used herein, the terms "object" and "substrate" are used interchangeably and refer to any discrete mass. An object or substrate can be a particle, bead, planar surface, phage, macromolecules, cell, microorganism, and the like.

"Particle": The term "particle," as used herein, refers to a discrete object. Such object can be of any shape or size. Composition of particles may vary, depending on applications and methods of synthesis. Suitable materials include, but are not limited to, plastics, ceramics, glass, polystyrene, methylstyrene, acrylic polymers, metal, paramagnetic materials, thoria sol, carbon graphited, titanium dioxide, latex or cross-linked dextrans such as Sepharose, cellulose, nylon, cross-linked micelles and teflon. In some embodiments, particles can be optically or magnetically detectable. In some embodiments, particles contain fluorescent or luminescent moieties, or other detectable moieties. In some embodiments, particles having a diameter of less than 1000 nanometers (nm) are also referred to as nanoparticles.

"Polynucleotide", "nucleic acid", or "oligonucleotide": The terms "polynucleotide", "nucleic acid", or "oligonucleotide" refer to a polymer of nucleotides. The terms "polynucleotide", "nucleic acid", and "oligonucleotide", may be used interchangeably. Typically, a polynucleotide comprises at least three nucleotides. DNAs and RNAs are polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

"Probe": As used herein, the term "probe" refers to a fragment of DNA or RNA of variable length (e.g., 3-1000 bases long), which is used to detect the presence of target nucleotide sequences that are complementary to the sequence in the probe. Typically, the probe hybridizes to single-stranded nucleic acid (DNA or RNA) whose base sequence allows probe-target base pairing due to complementarity between the probe and target.

"Secondary Structure": As used herein, the term "secondary structure", when used in connection with a nucleic acid structure, refers to any structure formed by basepairing interactions within a single molecule or set of interacting molecules. Exemplary secondary structures include stem-loop or double helix.

"Signal": As used herein, the term "signal" refers to a detectable and/or measurable entity. In certain embodiments, the signal is detectable by the human eye, e.g., visible. For example, the signal could be or could relate to intensity and/or wavelength of color in the visible spectrum. Non-limiting examples of such signals include colored precipitates and colored soluble products resulting from a chemical reaction such as an enzymatic reaction. In certain embodiments, the signal is detectable using an apparatus. In some embodiments, the signal is generated from a fluorophore that emits fluorescent light when excited, where the light is detectable with a fluorescence detector. In some embodiments, the signal is or relates to light (e.g., visible light and/or ultraviolet light) that is detectable by a spectrophotometer. For example, light generated by a chemiluminescent reaction could be used as a signal. In some embodiments, the signal is or relates to radiation, e.g., radiation emitted by radioisotopes, infrared radiation, etc. In certain embodiments, the signal is a direct or indirect indicator of a property of a physical entity. For example, a signal could be used as an indicator of amount and/or concentration of a nucleic acid in a biological sample and/or in a reaction vessel.

"Specific": As used herein, the term "specific," when used in connection with an oligonucleotide primer, refers to an oligonucleotide or primer, under appropriate hybridization or washing conditions, is capable of hybridizing to the target of interest and not substantially hybridizing to nucleic acids which are not of interest. Higher levels of sequence identity are preferred and include at least 60%, 65%, 70%, 75%, 80%, 85%, 90%, 95%, 98%, 99%, or 100% sequence identity. In some embodiments, a specific oligonucleotide or primer contains at least 4, 6, 8, 10, 12, 14, 16, 18, 20, 22, 24, 26, 28, 30, 35, 40, 45, 50, 55, 60, 65, 70, or more bases of sequence identity with a portion of the nucleic acid to be hybridized or amplified when the oligonucleotide and the nucleic acid are aligned.

"Stem-loop": As used herein, the term "stem-loop", when used in connection with a nucleic acid structure, refers to a structure caused by an intramolecular base pairing typically occurring in single-stranded DNA or in RNA. The structure is also known as a hairpin or hairpin loop. Typically, it occurs when two regions of the same strand, usually complementary in nucleotide sequence when read in opposite directions, base-pair to form a double helix that ends in an unpaired loop, resulting in lollipop-shaped structure.

"Substantially": As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

"Substantially complementary": As used herein, the term "substantially complementary" refers to two sequences that can hybridize under stringent hybridization conditions. The skilled artisan will understand that substantially complementary sequences need not hybridize along their entire length. In some embodiments, "stringent hybridization conditions" refer to hybridization conditions at least as stringent as the following: hybridization in 50% formamide, 5×SSC, 50 mM $NaH_2PO_4$, pH 6.8, 0.5% SDS, 0.1 mg/mL sonicated salmon sperm DNA, and 5×Denhart's solution at 42° C. overnight; washing with 2×SSC, 0.1% SDS at 45° C.; and washing with 0.2×SSC, 0.1% SDS at 45° C. In some embodiments, stringent hybridization conditions should not allow for hybridization of two nucleic acids which differ over a stretch of 20 contiguous nucleotides by more than two bases.

Detailed Description of Certain Embodiments

The present invention provides, among other things, methods and systems for characterizing multifunctional objects using a flow-through device, such as, a flow cytometer. In some embodiments, an inventive method according to the present invention includes one or more steps of (a) interrogating a plurality of objects (e.g., particles), wherein each individual object (e.g., particle) comprises one or more interrogation regions detectable as a sequence of events; (b) recording multiple events, wherein each individual event corresponds to each individual interrogation region detectable above a pre-determined triggering threshold; (c) grouping the recorded multiple events, and (d) characterizing the plurality of objects based on the grouped events. In some embodiments, the multiple events are recorded non-contemporaneously. In some embodiments, each interrogation region is characterized by a detectable signal pattern once interrogated. In some embodiments, the recorded events or signal patterns may be grouped based on spatial and/or temporal-proximity. In some embodiments, the recorded events or signal patterns may be grouped based on patterns of measured properties.

The present invention are particularly useful for multiplexed analyte detection and/or quantification. According to the invention, the binding between one or more target analytes and one or more objects (e.g., particles) typically alters events or signal patterns detected by inventive methods described herein. Therefore, the presence of the one or more target analytes may be detected based on the altered patterns. In some embodiments, the amount of analytes bound to objects (e.g., particles) may be further quantified based on the level of alteration.

Thus, the present invention provides compositions, methods and systems that permit multiplexed, robust, and efficient detection and/or quantification of target analytes based on rapid flow-through particle scanning using simple, inexpensive, or portable devices.

Various aspects of the invention are described in further detail in the following subsections. The use of subsections is not meant to limit the invention. Each subsection may apply to any aspect of the invention. In this application, the use of "or" means "and/or" unless stated otherwise.

Objects

The present invention may be used to characterize any objects. Suitable objects include, but are not limited to, particles, beads, phages (e.g., phages suitable for phage display), macromolecules (e.g., proteins including peptides or aggregated peptides, DNAs including DNA origami, and/or RNAs), cells including any genetically engineered cells (e.g., cells carrying green fluorescent protein (GFP) derivatives thereof and the like), micro-organisms (e.g., *C. elegans* (e.g., engineered nematodes for drug testing), bacteria, yeast, and/or fungi) including any genetically engineered micro-organisms (e.g., micro-organisms carrying GFP derivatives thereof and the like).

For illustration purposes, particles are described in connection with various embodiments below.

Particles

Particles suitable for use in accordance with the present invention can be made of any materials. Suitable particles can be biocompatible, non-biocompatible. Suitable particles can also be biodegradable or non-biodegradable.

Materials

In some embodiments, particles are made of polymers. Exemplary polymers include, but are not limited to, poly (arylates), poly(anhydrides), poly(hydroxy acids), polyesters, poly(ortho esters), poly(alkylene oxides), polycarbonates, poly(propylene fumerates), poly(caprolactones), polyamides, polyamino acids, polyacetals, polylactides, polyglycolides, poly(dioxanones), polyhydroxybutyrate, polyhydroxyvalyrate, poly(vinyl pyrrolidone), polycyanoacrylates, polyurethanes and polysaccharides. In some embodiments, polymers of particles include polyethylene glycol (PEG). In some embodiments, polymers of particles may be formed by step or chain polymerization. The amount and kind of radical initiator, e.g., photo-active initiator (e.g., UV or infrared), thermally-active initiator, or chemical initiator, or the amount of heat or light employed, may be used to control the rate of reaction or modify the molecular weight. Where desired, a catalyst may be used to increase the rate of reaction or modify the molecular weight. For example, a strong acid may be used as a catalyst for step polymerization. Trifunctional and other multifunctional monomers or cross-linking agents may also be used to increase the cross-link density. For chain polymerizations, the concentration of a chemical initiator in a mixture of one or more monomers may be adjusted to manipulate final molecular weight.

Exemplary methods for making particles are described in U.S. Pat. No. 7,709,544 and US Application Publication No.: 20080176216, the entire contents of which are incorporated herein by reference. For example, processes as discussed can be conducted with any polymerizable liquid-phase monomer in which shapes of particles suitable for use in the present invention, can be defined and polymerized in a single lithography-polymerization step. Exemplary monomers include Allyl Methacrylate, Benzyl Methylacrylate, 1,3-Butanediol Dimethacrylate, 1,4-Butanediol Dimethacrylate, Butyl Acrylate, n-Butyl Methacrylate, Diethyleneglycol Diacrylate, Diethyleneglycol Dimethacrylate, Ethyl Acrylate, Ethyleneglycol Dimethacrylate, Ethyl Methacrylate, 2-Ethyl Hexyl Acrylate, 1,6-Hexanediol Dimethacrylate, 4-Hydroxybutyl Acrylate, Hydroxyethyl Acrylate, 2-Hydroxyethyl Methacrylate, 2-Hydroxypropyl Acrylate, Isobutyl Methacrylate, Lauryl Methacrylate, Methacrylic Acid, Methyl Acrylate, Methyl Methacrylate, Monoethylene Glycol, 2,2,3,3,4,4,5,5-Octafluoropentyl Acrylate, Pentaerythritol Triacrylate, Polyethylene Glycol (200) Diacrylate, Polyethylene Glycol (400) Diacrylate, Polyethylene Glycol (600) Diacrylate, Polyethylene Glycol (200) Dimethacrylate, Polyethylene Glycol (400) Dimethacrylate, Polyethylene Glycol (600) Dimethacrylate, Stearyl Methacrylate, Triethylene Glycol, Triethylene Glycol Dimethacrylate, 2,2,2-Trifluoroethyl 2-methylacrylate, Trimethylolpropane Triacrylate, Acrylamide, N,N,-methylene-bisacryl-amide, Phenyl acrylate, Divinyl benzene, etc. In certain embodiments, a monomer is characterized by a polymerization reaction that can be terminated with a termination species. The terminating species, lithographic illumination, and monomer constituents are therefore selected in cooperation to enable making particles suitable for use in the present invention.

In some embodiments, particles are hydrogels. In general, hydrogels comprise a substantially dilute crosslinked network. Water or other fluids can penetrate in the network forming such a hydrogel. In some embodiments, hydrogels suitable for use in the present invention are made of or comprise a hydrophilic polymer. For example, hydrophilic polymers may comprise anionic groups (e.g. phosphate group, sulphate group, carboxylate group); cationic groups (e.g. quaternary amine group); or polar groups (e.g. hydroxyl group, thiol group, amine group). In some embodiments, hydrogels are superabsorbent (e.g. they can contain over 99% water) and possess a degree of flexibility very similar to natural tissue, due to their significant water content. Both of weight and volume, hydrogels are fluid in composition and thus exhibit densities to those of their constituent liquids (e.g., water). The present invention encompasses the recognition that hydrogels are particularly useful in some embodiments of the present invention. Without wishing to be bound to any particular theory, it is contemplated that hydrogels enable 1) ease of implementation with detection instruments, in particular, commercially available instruments without substantial modifications (e.g., flow cytometers), and 2) ease of incorporation of functional moieties (e.g., in a single lithography-polymerization step) without requiring surface functionalization. Due to their bio-friendly nature, hydrogels have been used extensively in the fields of tissue engineering, drug delivery, and biomolecule separation.

Various additional materials and methods can be used to synthesize particles. In some embodiments, particles may be made of or comprise one or more polymers. Polymers used in particles may be natural polymers or unnatural (e.g. synthetic) polymers. In some embodiments, polymers can be linear or branched polymers. In some embodiments, polymers can be dendrimers. Polymers may be homopolymers or copolymers comprising two or more monomers. In terms of sequence, copolymers may be block copolymers, graft copolymers, random copolymers, blends, mixtures, and/or adducts of any of the foregoing and other polymers.

In some embodiments, particles of the present invention may be made of or comprise a natural polymer, such as a carbohydrate, protein, nucleic acid, lipid, etc. In some embodiments, natural polymers may be synthetically manufactured. Many natural polymers, such as collagen, hyaluronic acid (HA), and fibrin, which derived from various components of the mammalian extracellular matrix can be used in particles of the present invention. Collagen is one of the main proteins of the mammalian extracellular matrix, while HA is a polysaccharide that is found in nearly all animal tissues. Alginate and agarose are polysaccharides that are derived from marine algae sources. Some advantages of natural polymers include low toxicity and high biocompatibility.

In some embodiments, a polymer is a carbohydrate. In some embodiments, a carbohydrate may be a monosaccharide (i.e. simple sugar). In some embodiments, a carbohydrate may be a disaccharide, oligosaccharide, and/or polysaccharide comprising monosaccharides and/or their derivatives connected by glycosidic bonds, as known in the art. Although carbohydrates that are of use in the present invention are typically natural carbohydrates, they may be at least partially-synthetic. In some embodiments, a carbohydrate is a derivatized natural carbohydrate.

In certain embodiments, a carbohydrate is or comprises a monosaccharide, including but not limited to glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid. In certain embodiments, a carbohydrate is or comprises a disaccharide, including but not limited to lactose, sucrose, maltose, trehalose, and cellobiose. In certain embodiments, a carbohydrate is or comprises a polysaccharide, including but not limited to hyaluronic acid (HA), alginate, heparin, agarose, chitosan, N,O-carboxylmethylchitosan, chitin, cellulose, microcrystalline cellulose, hydroxypropyl methylcellulose (HPMC), hydroxycellulose (HC), methylcellulose (MC), pullulan, dextran, cyclodextran, glycogen, starch, hydroxyethylstarch, carageenan, glycon, amylose, starch, heparin, konjac, glucommannan, pustulan, curdlan, and xanthan. In certain embodiments, the carbohydrate is a sugar alcohol, including but not limited to mannitol, sorbitol, xylitol, erythritol, maltitol, and lactitol.

In some embodiments, particles of the present invention may be made of or comprise synthetic polymers, including, but not limited to, poly(arylates), poly(anhydrides), poly(hydroxy acids), poly(alkylene oxides), poly(propylene fumerates), polymethacrylates polyacetals, polyethylenes, polycarbonates (e.g. poly(1,3-dioxan-2-one)), polyanhydrides (e.g. poly(sebacic anhydride)), polyhydroxyacids (e.g. poly(β-hydroxyalkanoate)), polypropylfumarates, polycaprolactones, polyamides (e.g. polycaprolactam), polyacetals, polyethers, polyesters (e.g. polylactide, polyglycolide, poly(dioxanones), polyhydroxybutyrate,), poly(orthoesters), polycyanoacrylates, polyvinyl alcohols, polyurethanes, polyphosphazenes, polyacrylates, polymethacrylates, polyureas, polyamines and copolymers thereof. Exemplary polymers also include polyvalerolactone, poly(sebacic anhydride), polyethylene glycol, polystyrenes, polyhydroxyvalyrate, poly(vinyl pyrrolidone)poly(hydroxyethyl methacrylate) (PHEMA), poly(vinyl alcohol) (PVA), and derivatives and copolymers thereof.

In some embodiments, polymers of particles may be formed by step or chain polymerization. The amount and kind of radical initiator, e.g., photo-active initiator (e.g., UV or infrared), thermally-active initiator, or chemical initiator, or the amount of heat or light employed, may be used to control polymerization rate or modify molecular weights of resulting polymers. Where desired, a catalyst may be used to increase the rate of reaction or modify the molecular weight. For example, a strong acid may be used as a catalyst for step polymerization. Trifunctional and other multifunctional monomers or cross-linking agents may also be used to increase cross-link density of polymers. For chain polymerizations, the concentration of a chemical initiator in a mixture of one or more monomers may be adjusted to manipulate final molecular weight.

In some embodiments, photocrosslinking methods are utilized to make polymeric particles in accordance with the present invention. Photoinitiators produce reactive free radical species that initiate the crosslinking and/or polymerization of monomers upon exposure to light. Any photoinitiator may be used in the crosslinking and/or polymerization reaction. Photoinitiated polymerizations and photoinitiators are discussed in detail in Rabek, *Mechanisms of Photophysical Processes and Photochemical Reactions in Polymers*, New York: Wiley & Sons, 1987; Fouassier, *Photoinitiation, Photopolymerization, and Photocuring*, Cincinnati, Ohio: Hanser/Gardner; Fisher et al., 2001, *Annu. Rev. Mater. Res.*, 31:171. A photoinitiator may be designed to produce free radicals at any wavelength of light. In certain embodiments, the photoinitiator is designed to work using UV light (200-500 nm). In certain embodiments, long UV rays are used. In other embodiments, short UV rays are used. In some embodiments, a photoinitiator is designed to work using visible light (400-800 nm). In certain embodiments, a photoinitiator is designed to work using blue light (420-500 nm). In some embodiments, the photoinitiator is designed to work using IR light (800-2500 nm). The output of light can be controlled to provide greater control over the crosslinking and/or polymerization reaction. Control over polymerization in turn results in control over characteristics and/or properties of the resulting hydrogel.

In some embodiments, particle can be or comprises inorganic polymer such as silica ($SiO_2$). In some embodiments, particles according to the invention are silica-based. For example, silicate materials may be useful for the present applications due to their biocompatibility, ease of production and functionalization, and large surface-to-volume ratio. Silica-based particles such as porous silica particles, and any modified or hybrid particles can be of use in accordance with the present invention.

As well known in the art, silica-based particles may be made by a variety of methods. Some methods utilize the Stöber synthesis which involves hydrolysis of tetraethoxyorthosilicate (TEOS) catalyzed by ammonia in water/ethanol mixtures, or variations thereof. In some embodiments, silica-based particles are synthesized using known sol-gel chemistry, e.g., by hydrolysis of a silica precursor or precursors. Silica precursors can be provided as a solution of a silica precursor and/or a silica precursor derivative. Hydrolysis can be carried out under alkaline (basic) or acidic conditions. For example, hydrolysis can be carried out by addition of ammonium hydroxide to a solution comprising one or more silica precursor and/or derivatives. Silica precursors are compounds which under hydrolysis conditions can form silica. Examples of silica precursors include, but are not limited to, organosilanes such as, for example, tetraethoxysilane (TEOS), tetramethoxysilane (TMOS) and the like. In some embodiments, silica precursor has a functional group. Examples of such silica precursors includes, but is not limited to, isocyanatopropyltriethoxysilane (ICPTS), aminopropyltrimethoxysilane (APTS), mercaptopropyltrimethoxysilane (MPTS), and the like. In some embodiments, microemulsion procedures can be used to synthesize particles suitable for use in the present invention. For example, a water-in-oil emulsion in which water droplets are dispersed as nanosized liquid entities in a continuous domain of oil and surfactants and serve as nanoreactors for nanoparticle synthesis offer a convenient approach.

In some embodiments, particles may contain detectable moieties that generate fluorescent, luminescent and/or scatter signal. In certain embodiments, particles contain quantum dots (QDs). QDs are bright, fluorescent nanocrystals with physical dimensions small enough such that the effect of quantum confinement gives rise to unique optical and electronic properties. Semiconductor QDs are often composed of atoms from groups II-VI or III-V in the periodic table, but other compositions are possible. By varying their size and composition, the emission wavelength can be tuned (i.e., adjusted in a predictable and controllable manner) from the blue to the near infrared. QDs generally have a broad absorption spectrum and a narrow emission spectrum. Thus different QDs having distinguishable optical properties (e.g., peak emission wavelength) can be excited using a single source. In general, QDs are brighter and photostable than most conventional fluorescent dyes. QDs and methods for their synthesis are well known in the art (see, e.g., U.S. Pat. Nos. 6,322,901; 6,576,291; and 6,815,064; all of which are incorporated herein by reference). QDs can be rendered water soluble by applying coating layers comprising a variety of different materials (see, e.g., U.S. Pat. Nos. 6,423,551; 6,251,303; 6,319,426; 6,426,513; 6,444,143; and 6,649,138; all of which are incorporated herein by reference). For example, QDs can be solubilized using amphiphilic polymers. Exemplary polymers that have been employed include octylamine-modified low molecular weight polyacrylic acid, polyethylene-glycol (PEG)-derivatized phospholipids, polyanhydrides, block copolymers, etc.

Exemplary QDs suitable for use in accordance with the present invention in some embodiments, includes ones with a wide variety of absorption and emission spectra and they are commercially available, e.g., from Quantum Dot Corp. (Hayward Calif.; now owned by Invitrogen) or from Evident Technologies (Troy, N.Y.). For example, QDs having peak emission wavelengths of approximately 525 nm, approximately 535 nm, approximately 545 nm, approximately 565 nm, approximately 585 nm, approximately 605 nm, approximately 655 nm, approximately 705 nm, and approximately 800 nm are available. Thus QDs can have a range of different colors across the visible portion of the spectrum and in some cases even beyond.

In certain embodiments, optically detectable particles are or comprise metal particles. Metals of use include, but are not limited to, gold, silver, iron, cobalt, zinc, cadmium, nickel, gadolinium, chromium, copper, manganese, palladium, tin, and alloys thereof. Oxides of any of these metals can be used.

Certain metal particles, referred to as plasmon resonant particles, exhibit the well known phenomenon of plasmon resonance. The features of the spectrum of a plasmon resonant particle (e.g., peak wavelength) depend on a number of factors, including the particle's material composition, the shape and size of the particle, the refractive index or dielectric properties of the surrounding medium, and the presence of other particles in the vicinity. Selection of particular particle shapes, sizes, and compositions makes it possible to produce particles with a wide range of distinguishable optically detectable properties thus allowing for concurrent detection of multiple analytes by using particles with different properties such as peak scattering wavelength.

Magnetic properties of particles can be used in accordance with the present invention. Particles in some embodiments are or comprise magnetic particles, that is, magnetically responsive particles that contain one or more metals or oxides or hydroxides thereof. Magnetic particles may comprise one or more ferrimagnetic, ferromagnetic, paramagnetic, and/or superparamagnetic materials. Useful particles may be made entirely or in part of one or more materials selected from the group consisting of: iron, cobalt, nickel, niobium, magnetic iron oxides, hydroxides such as maghemite ($\gamma$-$Fe_2O_3$), magnetite ($Fe_3O_4$), feroxyhyte (FeO(OH)), double oxides or hydroxides of two- or three-valent iron with two- or three-valent other metal ions such as those from the first row of transition metals such as Co(II), Mn(II), Cu(II), Ni(II), Cr(III), Gd(III), Dy(III), Sm(III), mixtures of the afore-mentioned oxides or hydroxides, and mixtures of any of the foregoing. See, e.g., U.S. Pat. No. 5,916,539 (incorporated herein by reference) for suitable synthesis methods for certain of these particles. Additional materials that may be used in magnetic particles include yttrium, europium, and vanadium.

Size and Shape

In general, particles suitable for the present invention can be of any size. In some embodiments, suitable particles have a greatest dimension (e.g. diameter) of less than 1000 micrometers (μm). In some embodiments, suitable particles have a greatest dimension of less than 500 μm. In some embodiments, suitable particles have a greatest dimension of less than about 250 μm. In some embodiments, suitable particles have a greatest dimension (e.g. diameter) of less than about 200 μm, about 150 μm, about 100 μm, about 90 μm, about 80 μm, about 70 μm, about 60 μm, about 50 μm, about 40 μm, about 30 μm, about 20 μm, or about 10 μm. In some embodiments, suitable particles have a greatest dimension of less than 1000 nm. In some embodiments, suitable particles have a greatest dimension of less than 500 nm. In some embodiments, suitable particles have a greatest dimension of less than about 250 nm. In some embodiments, a greatest dimension is a hydrodynamic diameter.

Suitable particles can have a variety of different shapes including, but not limited to, spheres, oblate spheroids, cylinders, ovals, ellipses, shells, cubes, cuboids, cones, pyramids, rods (e.g., cylinders or elongated structures having a square or rectangular cross-section), tetrapods (particles having four leg-like appendages), triangles, prisms, etc. In some embodiments, particles are rod-shaped. In some embodiments, particles are bar-shaped. In some embodiments, particles are bead-shaped. In some embodiments, particles are column-shaped. In some embodiments, particles are ribbon or chain-like. In some embodiments, particles can be of any geometry or symmetry. For example, planar, circular, rounded, tubular, ring-shaped, tetrahedral, hexagonal, octagonal particles, particles of other regular geometries, and/or particles of irregular geometries can also be used in the present invention. Additional suitable particles with various sizes and shapes are disclosed in U.S. Pat. Nos. 7,709,544 and 7,947,487 and can be used in the present invention, which are incorporated herein by reference.

Particles may have various aspect ratios of their dimensions, such as length/width, length/thickness, etc. Particles, in some embodiments, can have at least one dimension, such as length, that is longer than another dimension, such as width. According to the present invention, particles having at least one aspect ratio greater than one may be particularly useful in flow-through scanning (e.g., in a flow cytometer) to facilitate their self-alignment. In some embodiments, particles may have at least one aspect ratio of at least 1.5:1, at least 2:1, at least 2.5:1, at least 3:1, at least 5:1, at least 10:1, or even greater.

It is often desirable to use a population of particles that is relatively uniform in terms of size, shape, and/or composition so that each particle has similar properties. In some embodiments, a population of particles with homogeneity with diameters (e.g., hydrodynamic diameters) are used. As used herein, a population of particles with homogeneity with diameters (e.g., hydrodynamic diameters) refers to a population of particles with at least about 80%, at least about 90%, or at least about 95% of particles with a diameter (e.g., hydrodynamic diameter) that falls within 5%, 10%, or 20% of the average diameter (e.g., hydrodynamic diameter). In some embodiments, the average diameter (e.g., hydrodynamic diameter) of a population of particles with homogeneity with diameters (e.g., hydrodynamic diameters) ranges as discussed above. In some embodiments, a population of particles with homogeneity with diameters (e.g., hydrodynamic diameters) refers to a population of particles that has a polydispersity index less than 0.2, 0.1, 0.05, 0.01, or 0.005. For example, polydispersity index of particles used in accordance with the present invention is in a range of about 0.005 to about 0.1. Without wishing to be bound by any theory, it is contemplated that particles with homogeneity (e.g., with respect to particle size) may have higher repeatability and can produce more accuracy in the present application. In some embodiments, a population of particles may be heterogeneous with respect to size, shape, and/or composition.

Particles can be solid or hollow and can comprise one or more layers (e.g., nanoshells, nanorings, etc.). Particles may have a core/shell structure, wherein the core(s) and shell(s) can be made of different materials. Particles may comprise gradient or homogeneous alloys. Particles may be composite particles made of two or more materials, of which one, more than one, or all of the materials possesses magnetic properties, electrically detectable properties, and/or optically detectable properties.

Particles may have a coating layer. Use of a biocompatible coating layer can be advantageous, e.g., if the particles contain materials that are toxic to cells. Suitable coating materials include, but are not limited to, natural proteins such as bovine serum albumin (BSA), biocompatible hydrophilic polymers such as polyethylene glycol (PEG) or a PEG derivative, phospholipid-(PEG), silica, lipids, polymers, carbohydrates such as dextran, other nanoparticles that can be associated with inventive nanoparticles etc. Coatings may be applied or assembled in a variety of ways such as by dipping, using a layer-by-layer technique, by self-assembly, conjugation, etc. Self-assembly refers to a process of spontaneous assembly of a higher order structure that relies on the natural attraction of the components of the higher order structure (e.g., molecules) for each other. It typically occurs through random movements of the molecules and formation of bonds based on size, shape, composition, or chemical properties. In some embodiments, particles with coating are also referred to as functionalized particles or surface treated particles.

In certain embodiments of the invention, a particle is porous, by which is meant that the particle contains holes or channels, which are typically small compared with the size of a particle. For example a particle may be a porous silica particle, e.g., a porous silica nanoparticle or may have a coating of porous silica. Particles may have pores ranging from about 1 nm to about 200 nm in diameter, e.g., between about 1 nm and 50 nm in diameter. Between about 10% and 95% of the volume of a particle may consist of voids within the pores or channels.

In some embodiments, particles may optionally comprise one or more dispersion media, surfactants, release-retarding ingredients, or other pharmaceutically acceptable excipient. In some embodiments, particles may optionally comprise one or more plasticizers or additives.

In various embodiments, particles described herein may have at least one region bearing one or more probes described herein. In some embodiments, particles may have at least one encoded region. In some embodiments, particles have at least one encoded region and at least one region bearing one or more probes. Such regions can be discrete regions of substrates (objects) including particles used in accordance with the present invention. Each region, in some embodiments, can be optionally functionalized. In various embodiments, particles described herein may bear an indicator for orientation (e.g., indicating coding region first followed by probe region or vice versa).

Functionalization

Various methods known in the art (e.g., as discussed in U.S. Pat. Nos. 7,709,544 and 7,947,487) and provided in the present application are useful for functionalization of substrates or objects (e.g., particles) described herein.

Various functional moieties or groups may be introduced to the surface of the objects that produce selected functionality (e.g., to capture encoding adapters, probes or target nucleic acids). Such functional moieties can be chemically attached to the surface, e.g., by covalent incorporation, or can be physically attached thereto or entrapped therein.

In some embodiments, at least a portion of an object (e.g., particle) is made from a monomer. Such a monomer can be used alone or in combination with copolymerized species to provide a selected functionality in the resulting object. For example, a functional moiety can be provided as a monomer or a part of a monomer that are polymerized, for example, by a lithography-polymerization step of particle synthesis (see, U.S. Pat. Nos. 7,709,544 and 7,947,487 for details).

It is not intended that the present invention be limited to a particular coding scheme. A signature for encoding can be a visually detectable feature such as, for example, color, apparent size, or visibility (i.e. simply whether or not the particle is visible under particular conditions).

In many embodiments, graphical signatures and/or optically detectable signatures are particularly useful in the present invention. In various embodiments of the present invention, graphically encoding as discussed in U.S. Pat. No. 7,947,487 and encoding (e.g., universal encoding) as disclosed herein are used.

In some embodiments, a graphical signature for encoding is or comprises one or more spatially patterned features. In some embodiments, spatially patterned features include a plurality of open and closed coding elements. Coding elements can be arranged in a two-dimensional grid. Coding elements can also have non-uniform shapes or sizes. In certain embodiments, spatially patterned features further include an orientation indicator.

Additionally or alternatively, an optical signature can be used in accordance with the present invention. In some embodiments, an optical signature for encoding is or comprises a feature of an absorption, emission, reflection, refraction, interference, diffraction, dispersion, scattering, or any combination thereof.

In some embodiments, an optical signature is intrinsic to functionalized substrates in accordance with the present invention. In some embodiments, an optical signature is introduced to functionalized substrates. Such introduction can be done before, with or after contacting with a sample, generating a signal from such contacting, and/or detecting such a signal.

To give but one example, a functionalized object (e.g., particle) may carry a functional moiety that is not itself detectable, but upon further interaction with and/or modification by other moieties can become detectable. In some embodiments, such a functional moiety can be a functional group or moiety to facilitate association between a substrate and other entities.

Thus, additionally or alternatively, object surface is functionalized to introduce chemical functional moieties that are designed to facilitate association between a substrate and other entities (e.g., probes, encoding agents, etc.). Suitable functional moieties can be introduced to a surface of substrates by covalent attachment. In some embodiments, coupling agents can be used with various substrates for functionalization. Exemplary coupling agents may include bifunctional, tri-functional, and higher functional coupling agents, which are well known in the art, such as $MeSiCl_3$, dioctylphthalate, polyethylene-glycol (PEG), etc. In some embodiments, substrates are functionalized by covalent attachment of streptavidin onto their surface via a heterobifunctional cross-linker with a polyethylene-glycol (PEG) spacer arm. A variety of functionalization methods are known in the art and can be used to practice the present invention.

In some embodiments, an object surface is functionalized by introducing capturing or anchor oligonucleotides to facilitate capturing and immobilization of individual nucleic acid molecules such as single-stranded polynucleotide templates, encoding adapters or probes. In some embodiments, capturing or anchor oligonucleotides can contain sequences complementary to a universal sequence present on nucleic acid template molecules. Exemplary capturing or anchor oligonucleotides can contain various numbers of nucleotides. For example, suitable oligonucleotides may contain 1-50 nucleotides (e.g., 3-40, 3-30, 3-20, 30-15, 3-10, 6-40, 6-30, 6-20, 6-10, 8-30, 8-20, 8-15, 10-30, 10-20, 10-15 nucleotides). In some embodiments, suitable oligonucleotides may contain 1, 2, 3, 6, 8, 10, 12, 14, 16, 18, 20, 25, 30, 35, 40, 45, or 50 nucleotides. Various methods are known in the art for design and synthesize suitable capturing or anchor oligonucleotides and such methods are well within skills of ordinary artisan.

In some embodiments, capturing or anchor oligonucleotides may be separately synthesized and attached to a substrate surface for use, e.g. as disclosed by Lund et al. Nucleic Adds Research, 16: 10861-10880 (1988); Albretsen et al, Anal. Biochem., 189: 40-50 (1990); Wolf et al, Nucleic Acids Research, 15: 2911-2926 (1987); or Ghosh et al, Nucleic Acids Research, 15: 5353-5372 (1987).

In some embodiments, the attachment is covalent in nature. In further embodiments, the covalent binding of the capturing or anchor oligonucleotides and nucleic acid template(s) to the substrate is induced by a crosslinking agent such as for example 1-ethyl-3-(3-dimethylaminopropyl)-carbodiimide hydrochloride (EDC), succinic anhydride, phenyldiisothiocyanate or maleic anhydride, or a heterobifunctional crosslinker such as for example m-maleimidobenzoyl-N-hydroxysuccinimide ester (MBS), N-succinimidyl[4-iodoacethyl]aminobenzoate (SIAB), Succinimidyl 4-[N-maleimidomethyl]cyclohexane-1-carboxylate (SMCC), N-y-maleimidobutyryloxy-succinimide ester (GMBS), Succinimidyl-4-[p-maleimidophenyl]butyrate (SMPB) and the sulfo (water-soluble) corresponding compounds.

In some embodiments, functionalized objects bearing chemical groups or capturing or anchor oligonucleotides are used for encoding and/or probe region functionalization. In particular embodiments, universal encoding is used to encode particles for the present invention.

Universal Encoding

Universal encoding enables the production of functionalized objects (e.g., particles) with a universal architecture, which can be further encoded to generate subgroups of objects with distinct barcode giving rise to distinct identity. For highly multiplexed assays, this greatly reduces production time and cost compared to independent synthesis of distinct objects for each target.

In some embodiments, a functionalized object (e.g., particle) comprises one or more universal encoding regions. Such encoding regions may be separated by inert or non-functionalized regions. Typically, each universal encoding region bearing one or more templates for capturing encoding adapters by covalent link via the functional groups or by hybridization and/or ligation to a capturing or anchor oligonucleotides on the functionalized surface. In some embodiments, a template is or comprises a single-stranded polynucleotide. For example, such a single-stranded polynucleotide can include a predetermined nucleotide sequence that specifically bind a desired encoding adapter. In some embodiments, a template further include a stem-loop structure (i.e., a hairpin structure). Predetermined nucleotide sequences, in certain embodiments, may be adjacent to stem-loop structures to facilitate ligation between the template and the encoding adapter. In such embodiments, an encoding adapter that binds the template typically does not form a secondary structure. In some embodiments, a single stranded template does not forms a hairpin structure, while an encoding adapter does.

In general, a predetermined nucleotide sequence with any base combinations or lengths can be used in accordance with the present invention. In some embodiments, a predetermined nucleotide sequence has a length of 1, 2, 3 bases or more. In some embodiments, a predetermined nucleotide sequence has a length of or more than 4 bases, 5 bases, 6 bases, 7 bases, 8 bases, 9 bases, 10 bases, 11 base, 12 bases, 13 bases, 14 bases, 15 bases, 20 bases, 25 bases or 30 bases. In some embodiments, a predetermined nucleotide sequence has a length in a range of any two values above. The length of predetermined nucleotide sequences can be the same for one substrate or can vary from each other. Typically, the predetermined sequence of a polynucleotide template complements the lock sequence of an encoding adapter.

In some embodiments, single-stranded polynucleotide templates can be used to capture encoding adapters. Suitable encoding adapters may be DNA, RNA, or any type of nucleic acid analog. In many embodiments, an encoding adapter is or comprises a single-stranded polynucleotide. In some embodiments, an encoding adapter comprises a nucleotide sequence that is complementary to the predetermined sequence of a corresponding template. Typically, an encoding adapter contains up to 30, 25, 20, 18, 16, 15, 14, 13, 12, 11, 10, 9, 8, 7, 6, 5, 4, 3, 2, or 1 nucleotides. In some embodiments, an encoding adapter contains about 10 bases with terminal 4 bases unique for each adapter and complementary to the predetermined sequence of a corresponding template ("lock sequence") and the other 6 bases common to all adapters.

In some embodiments, encoding adapters, once bound to the template, can be joined to the template by T4 DNA ligase or via other enzymatic or chemical coupling.

Encoding adapters can be labeled or unlabeled. In some embodiments, encoding adapters is labeled with a detectable moiety (e.g., an optically detectable moiety). Various detectable moieties may be used including fluorophores, chromophores, radioisotopes, quantum dots, nanoparticles and/or intercalating DNA/RNA dyes. Additional examples of detectable moieties are described in the Detectable Moieties section above.

In various embodiments, encoding adapters used in accordance with the present invention is a blend of labeled and unlabeled encoding adapters. In some embodiments, the labeled and unlabeled encoding adapters have the same or similar sequences and bind the same templates. In some embodiments, by varying the amount of labeled encoding adapters versus unlabeled encoding adapter, it is possible to control the amount of signal generated (e.g. fluorescence) in a region to achieve desired level. In some embodiments, a lock sequence can be used to selectively dictate which adapters will bind and be ligated to each hairpin probe region. In this way, several stripes of independently addressable hairpin probe regions can be used for encoding.

In some embodiments, a signal of at least one labeled encoding adapter is used to determine the orientation of the object (e.g., particle). In some embodiments, a signal of at least one labeled encoding adapter is used to normalized detectable signals form other labeled encoding adapters.

It is possible to use multiple colors (or emission wavelengths in general) when implementing the universal encoding scheme described herein. This may be accomplished by using blends of universal adapters modified with varying species, such as fluorophores, with unique emission spectra. Depending on the amount of each adapter added to the ligation mix, varying amounts will be ligated to the templates embedded in the particles, allowing levels of multiple "colors" to be adjusted in each encoding region. In one example, two fluorophores can be used to generate two-color codes on particles/substrates as shown below, but more colors can easily be used.

In some embodiments, fluorescence in each coding region can be distinguishable at multiple levels, e.g., up to 10-20 levels (e.g., up to 1, 2, 3, 4, 5, 6, 7, 8, 9, 10, 11, 12, 13, 14, 15, 16, 17, 18, 19, or 20 levels). For example, when three encoding regions are used and 10 levels are distinguishable for each, it would allow up to 1000 (10×10×10) unique codes. Additionally or alternatively, multiple signals (e.g., different fluorescent colors) can be used for encoding. In some embodiments, each encoding region has one signal distinct from each other. In some embodiments, substrates and encoding adapters can be designed such that at least one encoding region of the substrates is attached with one or more kinds of encoding adapters generating multiple signals. In some embodiments, each encoding region has multiple signals and by varying the amount of encoding adapters, a desired signal ratio can be achieved for encoding.

Probe Region Functionalization

Figure 1A:
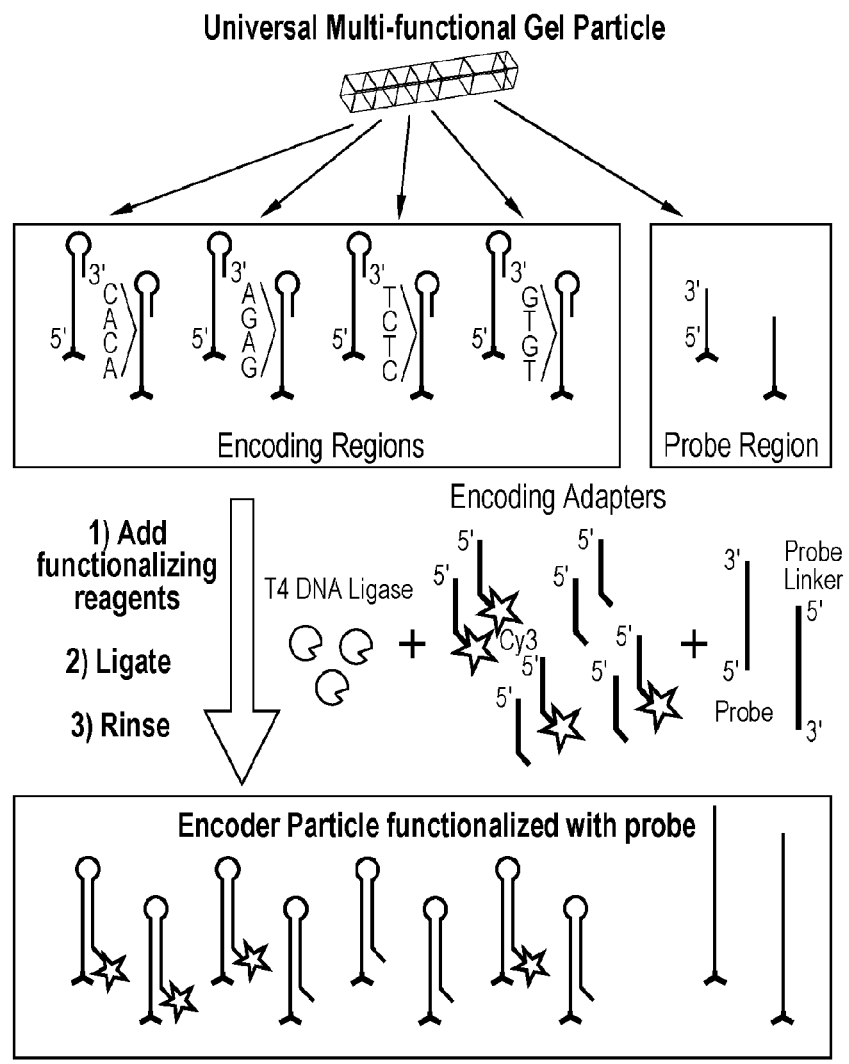
FIG. 1 illustrates an exemplary schematic for universal encoding and functionalization. (a) Hydrogel particles are made to have several universal encoding regions, each with a stem-loop structure and unique 4 bp sequence adjacent to the stem-loop, and a universal anchor in the probe region. In a ligation reaction, encoding adapters are added at varying ratios of fluorescently-modified to unmodified in order to achieve a desired fluorescence level in each region while probes are added with linker sequence to add functionality to the particle probe region. (b) An example of two batches of particles with unique code and probes generated using a universal particle set with varying ligation adapters.
Figure 1B:
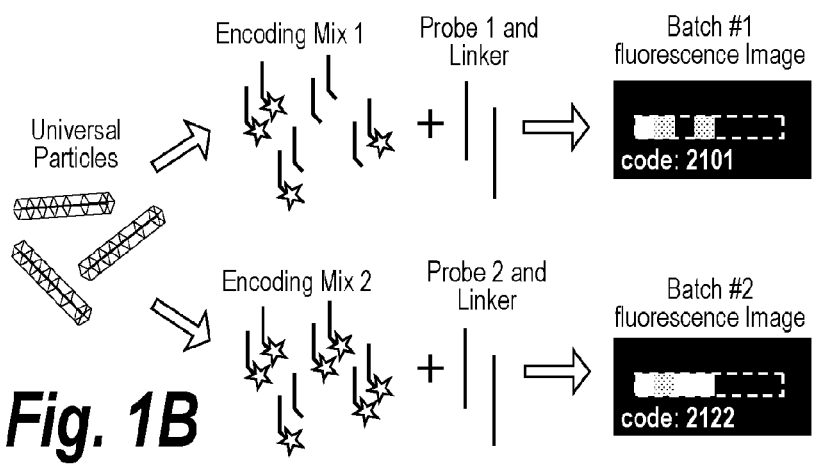
Figure 2:
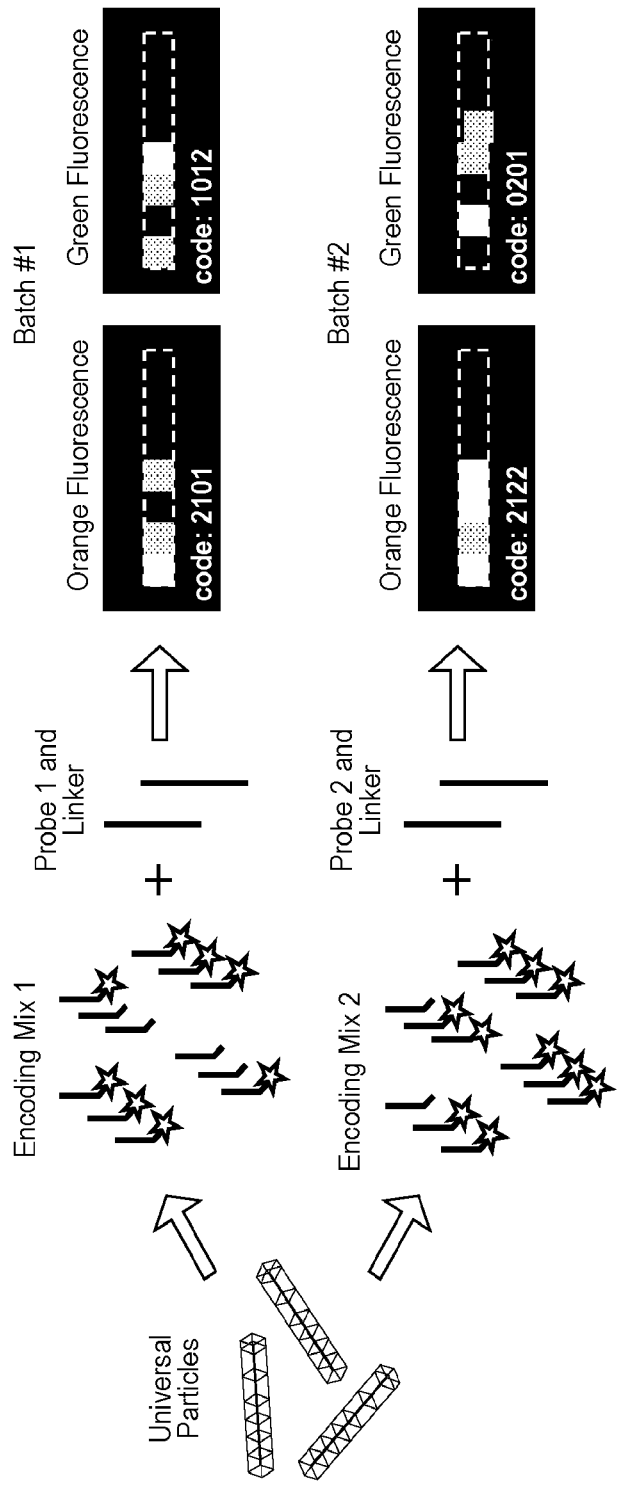
FIG. 2 illustrates an exemplary schematic for universal encoding using multiple fluorophores. Multiple adapter variants may be used, each with unique emission spectrum, to encode particles or substrates with more than one color (or otherwise functional species). The level of each color can be modulated by adjusting the ratio of each adapter variant to give unique signatures of multiple fluorescent colors in the coding regions of the particles.
Figure 3:
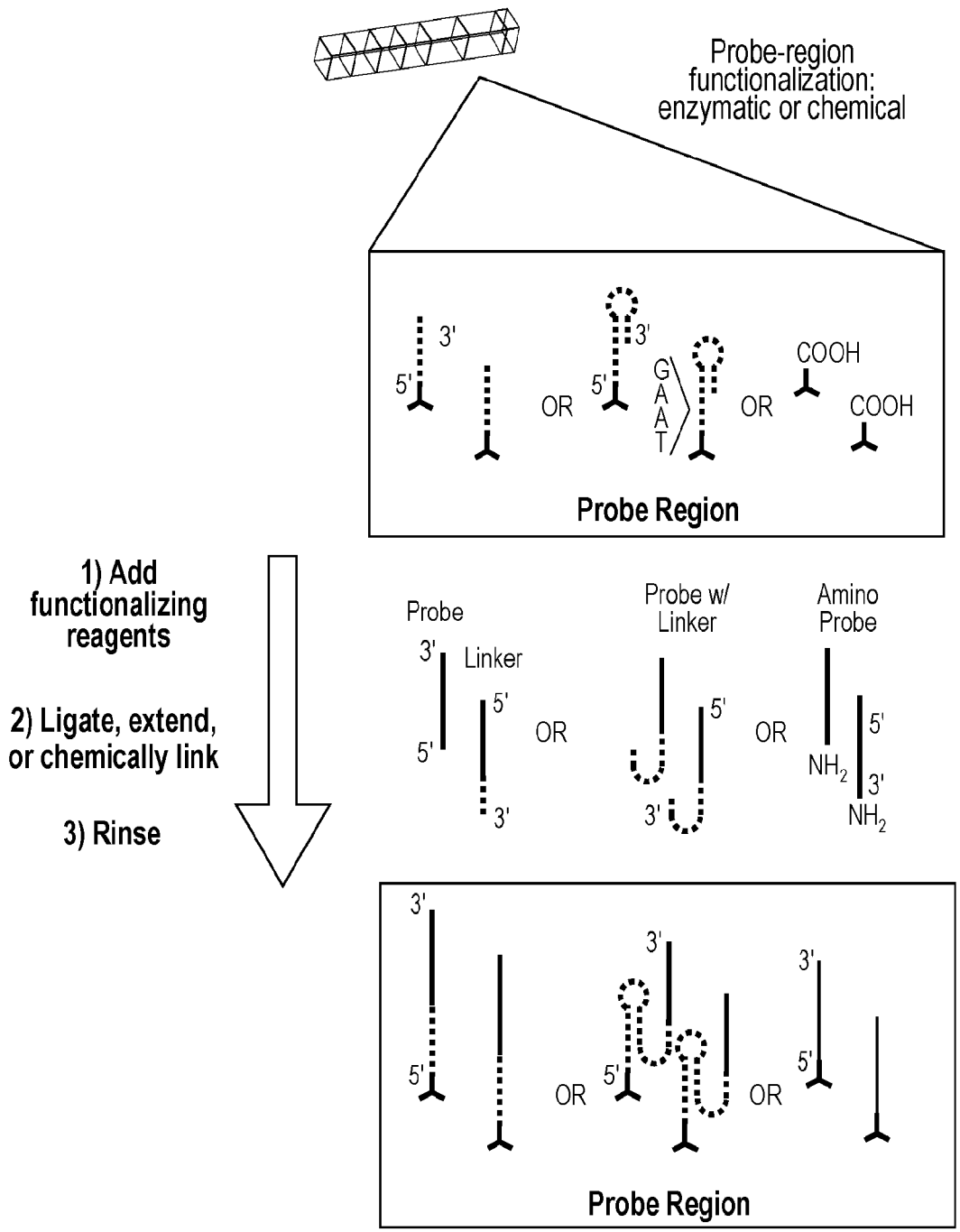
FIG. 3 illustrates an exemplary schematic of probe-region functionalization using three-species ligation, two-species ligation, and chemical modification.

A substrate used in accordance with the present invention can comprise one or more probe-bearing regions in addition to encoding regions. Two typical schematics for universal encoding and probe functionalization are represented in FIG. 1 and FIG. 2. In some embodiments, each probe region bears anchors for attaching probes of interest via, e.g., ligation-based approach. Ligation can be performed with three species (anchor, linker, and probe) or two species (hairpin anchor and probe). A schematic of probe-region functionalization using three-species ligation, two-species ligation, and chemical modification is depicted in FIG. 3.

In some embodiments, probe region functionalization includes chemical modification, such as the use of peptide chemistry to attach aminated probes to carboxylated substrates using carbodiimide chemistry. Exemplary methods for functionalization are shown in the Examples section below.

Desired probes specific for target nucleic acids may be designed using various methods known in the art. In some embodiments, desired probes for probe region functionalization include nucleic acid probes for post-hybridization labeling. For example, such a nucleic acid probe contains a capturing sequence for binding a target nucleic acid and an adjacent adapter sequence for binding a universal adapter (e.g., typically detectably labeled) such that binding of both the target nucleic acid and the universal adapter to the nucleic acid probe is detectable via post-hybridization labeling. See international application entitled "Nucleic Acid Detection and Quantification by Post-hybridization Labeling and Universal Encoding," filed on even date, the disclosure of which is hereby incorporated by reference.

In some embodiments, probe regions and encoding regions are separated from one another by inert regions. In some embodiments, one or more probe-bearing regions and one or more encoding regions overlap with each other. In some embodiments, an encoding and probe-bearing region can be the same region.

In some embodiments, different detectable signals (e.g., different fluorescent colors) may be used for encoding regions and probe-bearing regions. In some embodiments, same type of detectable signals are used, in particular, when encoding regions and probe-bearing regions are separated from each other.

For two-species functionalization, it is possible to use linear anchors and adapters that have hairpins. The adapter and anchor species may be designed to have minimal hairpin formation in ligation conditions or vary tightly bound hairpins. Detectable moieties for encoding may include fluorophores, chromophores, radioactive species, magnetic species, quantum dots, conductive materials, etc. Any number of coding regions may be used, and they need not be stripes. Any number of colors or otherwise distinguishable signals may be included in each encoding region. This approach may be used with other substrates including beads, planar surfaces, gel pads, etc. The substrates may be solid, polymer, emulsions, etc.

Figure 4:
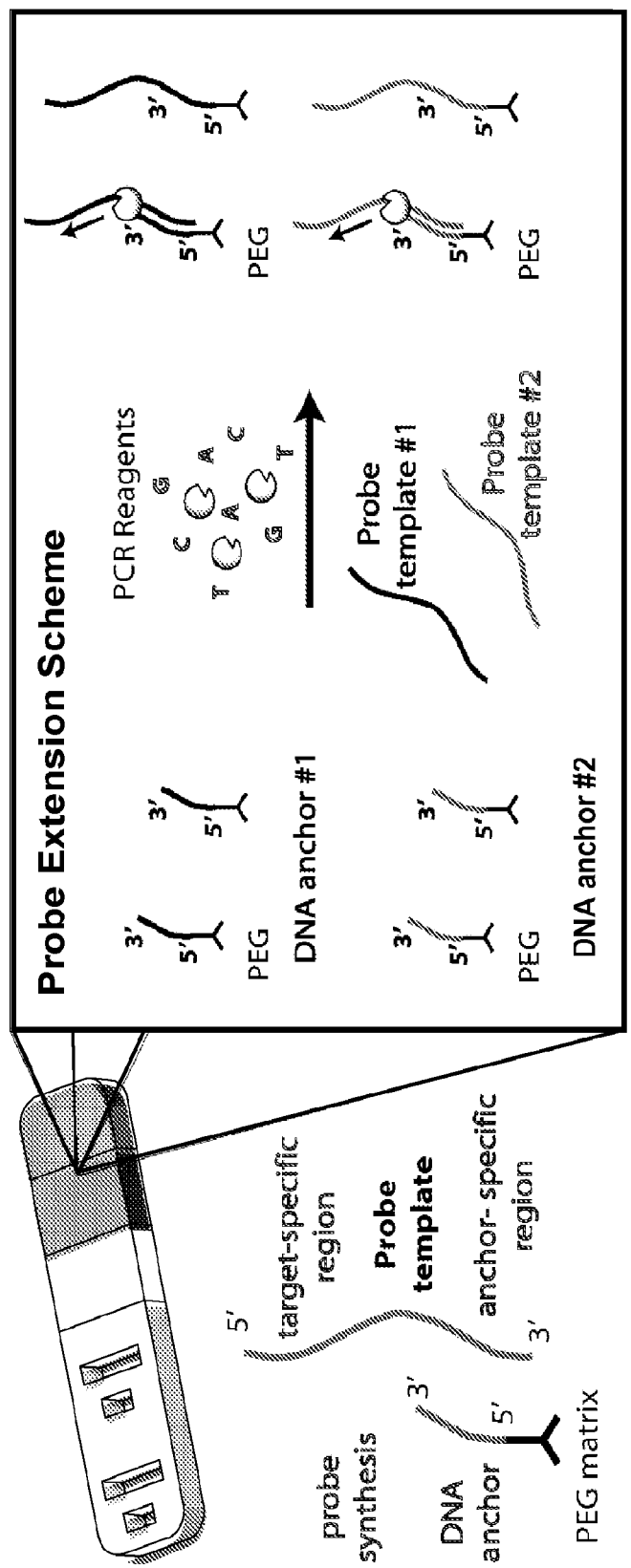
FIG. 4 illustrates an exemplary schematic showing the use of polymerase with probe-specific templates to add functionality to particles or substrates. Universal anchors (in this case there are two different anchors) are used with linkers that bear a region specific for one anchor and a probe sequence. Polymerases are used to extend the anchors along the linker, functionalizing the particles/substrates in one or multiple regions.

In addition to ligation based approach, inventive methods for universal encoding and/or functionalization can be implemented with other enzymes including ligases, polymerases, among others. For example, although T4 DNA ligase was used in the experiments described below, it is possible to use other enzymes to join oligonucleotides together. Other possible enzymes include, but are not limited to, other DNA ligases, RNA ligases, polymerases, etc. In a slightly different approach, polymerases can also be used to extend oligonucleotides, using a desired nucleic acid template, as means of adding nucleic acid probes for functionalization or labeled species for encoding or detection (FIG. 4). Using this approach or ligation-based approaches, multiple probe regions can be added to a single particle when multiple probe "anchors" are used.

Detectable Entities

Any of a wide variety of detectable agents can be used in the practice of the present invention. Suitable detectable agents include, but are not limited to: various ligands, radionuclides; fluorescent dyes; chemiluminescent agents (such as, for example, acridinum esters, stabilized dioxetanes, and the like); bioluminescent agents; spectrally resolvable inorganic fluorescent semiconductors nanocrystals (i.e., quantum dots); microparticles; metal nanoparticles (e.g., gold, silver, copper, platinum, etc.); nanoclusters; paramagnetic metal ions; enzymes; colorimetric labels (such as, for example, dyes, colloidal gold, and the like); biotin; dioxigenin; haptens; and proteins for which antisera or monoclonal antibodies are available.

In some embodiments, the detectable moiety is biotin. Biotin can be bound to avidins (such as streptavidin), which are typically conjugated (directly or indirectly) to other moieties (e.g., fluorescent moieties) that are detectable themselves.

Below are described some non-limiting examples of other detectable moieties.

Fluorescent Dyes

In certain embodiments, a detectable moiety is a fluorescent dye. Numerous known fluorescent dyes of a wide variety of chemical structures and physical characteristics are suitable for use in the practice of the present invention. A fluorescent detectable moiety can be stimulated by a laser with the emitted light captured by a detector. The detector can be a charge-coupled device (CCD) or a confocal microscope, which records its intensity.

Suitable fluorescent dyes include, but are not limited to, fluorescein and fluorescein dyes (e.g., fluorescein isothiocyanine or FITC, naphthofluorescein, 4',5'-dichloro-2',7'-dimethoxyfluorescein, 6-carboxyfluorescein or FAM, etc.), carbocyanine, merocyanine, styryl dyes, oxonol dyes, phycoerythrin, erythrosin, eosin, rhodamine dyes (e.g., carboxytetramethyl-rhodamine or TAMRA, carboxyrhodamine 6G, carboxy-X-rhodamine (ROX), lissamine rhodamine B, rhodamine 6G, rhodamine Green, rhodamine Red, tetramethylrhodamine (TMR), etc.), coumarin and coumarin dyes (e.g., methoxycoumarin, dialkylaminocoumarin, hydroxycoumarin, aminomethylcoumarin (AMCA), etc.), Oregon Green Dyes (e.g., Oregon Green 488, Oregon Green 500, Oregon Green 514., etc.), Texas Red, Texas Red-X, SPECTRUM RED™, SPECTRUM GREEN™, cyanine dyes (e.g., CY-3™, CY-5™, CY-3.5™, CY-5.5™, etc.), ALEXA FLUOR™ dyes (e.g., ALEXA FLUOR™ 350, ALEXA FLUOR™ 488, ALEXA FLUOR™ 532, ALEXA FLUOR™ 546, ALEXA FLUOR™ 568, ALEXA FLUOR™ 594, ALEXA FLUOR™ 633, ALEXA FLUOR™ 660, ALEXA FLUOR™ 680, etc.), BODIPY™ dyes (e.g., BODIPY™ FL, BODIPY™ R6G, BODIPY™ TMR, BODIPY™ TR, BODIPY™ 530/550, BODIPY™ 558/568, BODIPY™ 564/570, BODIPY™ 576/589, BODIPY™ 581/591, BODIPY™ 630/650, BODIPY™ 650/665, etc.), IRDyes (e.g., IRD40, IRD 700, IRD 800, etc.), and the like. For more examples of suitable fluorescent dyes and methods for coupling fluorescent dyes to other chemical entities such as proteins and peptides, see, for example, "The Handbook of Fluorescent Probes and Research Products", 9th Ed., Molecular Probes, Inc., Eugene, Oreg. Favorable properties of fluorescent labeling agents include high molar absorption coefficient, high fluorescence quantum yield, and photostability. In some embodiments, labeling fluorophores exhibit absorption and emission wavelengths in the visible (i.e., between 400 and 750 nm) rather than in the ultraviolet range of the spectrum (i.e., lower than 400 nm).

A detectable moiety may include more than one chemical entity such as in fluorescent resonance energy transfer (FRET). Resonance transfer results an overall enhancement of the emission intensity. For instance, see Ju et. al. (1995) Proc. Nat'l Acad. Sci. (USA) 92: 4347, the entire contents of which are herein incorporated by reference. To achieve resonance energy transfer, the first fluorescent molecule (the "donor" fluor) absorbs light and transfers it through the resonance of excited electrons to the second fluorescent molecule (the "acceptor" fluor). In one approach, both the donor and acceptor dyes can be linked together and attached to the oligo primer. Methods to link donor and acceptor dyes to a nucleic acid have been described previously, for example, in U.S. Pat. No. 5,945,526 to Lee et al., the entire contents of which are herein incorporated by reference. Donor/acceptor pairs of dyes that can be used include, for example, fluorescein/tetramethylrohdamine, IAEDANS/fluoroescein, EDANS/DABCYL, fluorescein/fluorescein, BODIPY FL/BODIPY FL, and Fluorescein/QSY 7 dye. See, e.g., U.S. Pat. No. 5,945,526 to Lee et al. Many of these dyes also are commercially available, for instance, from Molecular Probes Inc. (Eugene, Oreg.). Suitable donor fluorophores include 6-carboxyfluorescein (FAM), tetrachloro-6-carboxyfluorescein (TET), 2'-chloro-7'-phenyl-1,4-dichloro-6-carboxyfluorescein (VIC), and the like.

A suitable detectable moiety can be an intercalating DNA/RNA dye that have dramatic fluorescent enhancement upon binding to double-stranded DNA/RNA. Examples of suitable dyes include, but are not limited to, SYBR™ and Pico Green (from Molecular Probes, Inc. of Eugene, Oreg.), ethidium bromide, propidium iodide, chromomycin, acridine orange, Hoechst 33258, Toto-1, Yoyo-1, and DAPI (4',6-diamidino-2-phenylindole hydrochloride). Additional discussion regarding the use of intercalation dyes is provided by Zhu et al., *Anal. Chem.* 66:1941-1948 (1994), which is incorporated by reference in its entirety.

Enzymes

In certain embodiments, a detectable moiety is an enzyme or substrate thereof. Examples of suitable enzymes include, but are not limited to, those used in an ELISA, e.g., horseradish peroxidase, beta-galactosidase, luciferase, alkaline phosphatase, etc. Other examples include beta-glucuronidase, beta-D-glucosidase, urease, glucose oxidase, etc. An enzyme may be conjugated to a molecule using a linker group such as a carbodiimide, a diisocyanate, a glutaraldehyde, and the like.

Radioactive Isotopes

In certain embodiments, a detectable moiety is a radioactive isotope. For example, a molecule may be isotopically-labeled (i.e., may contain one or more atoms that have been replaced by an atom having an atomic mass or mass number different from the atomic mass or mass number usually found in nature) or an isotope may be attached to the molecule. Non-limiting examples of isotopes that can be incorporated into molecules include isotopes of hydrogen, carbon, fluorine, phosphorous, copper, gallium, yttrium, technetium, indium, iodine, rhenium, thallium, bismuth, astatine, samarium, and lutetium (i.e., 3H, 13C, 14C, 18F, 19F, 32P, 35S, 64Cu, 67Cu, 67Ga, 90Y, 99 mTc, 111In, 125I, 123I, 129I, 131I, 135I, 186Re, 187Re, 201Tl, 212Bi, 213Bi, 211At, 153Sm, 177Lu).

In some embodiments, signal amplification is achieved using labeled dendrimers as the detectable moiety (see, e.g., Physiol Genomics 3:93-99, 2000), the entire contents of which are herein incorporated by reference in their entirety. Fluorescently labeled dendrimers are available from Genisphere (Montvale, N.J.). These may be chemically conjugated to the oligonucleotide primers by methods known in the art.

Target Analytes

Methods and compositions described herein may be used to detect and/or quantify any target analytes. Examples of analytes include, but are not limited to, proteins, peptides, hormones, haptens, antigens, antibodies, receptors, enzymes, nucleic acids, polysaccharides, chemicals, polymers, pathogens, toxins, organic drugs, inorganic drugs, cells, tissues, microorganisms, viruses, bacteria, fungi, algae, parasites, allergens, pollutants, and combinations thereof. In some embodiments, the present invention is used to detect nucleic acids. Exemplary nucleic acids that can be detected and/or quantified using inventive methods of the present invention can be DNA, RNA, or any combination thereof. In certain embodiments of the present invention, a target nucleic acid may be or contain a portion of a gene, a regulatory sequence, genomic DNA, cDNA, RNA including mRNA, rRNA, microRNA, or any combination thereof.

A target nucleic acid, in various embodiments, can be one that is found in a biological organism including, for example, a microorganism or infectious agent, or any naturally occurring, bioengineered or synthesized component thereof.

According to the present invention, provided compositions and methodologies are particularly useful in quantifying transcript (e.g., primary transcripts, mRNA, etc.) nucleic acids. In some embodiments, provided methods herein are used to detect and/or quantify miRNAs. miRNAs can be found in genomes of humans, animals, plants and viruses. According to the present invention, a target nucleic acid, in some embodiments, can be or comprise one or more miRNAs that is/are generated from endogenous hairpin-shaped transcripts. In some embodiments, a target nucleic acid can be or comprise one or more miRNAs that is/are transcribed as long primary transcripts (pri-microRNAs), for example, by RNA polymerase II enzyme in animals. There are total 475 human miRNA genes currently listed in the miRNA database (http://microrna.sanger.ac.uk/sequences/ftp.shtml) and there are predictions that this number will go up to approximately 1000, which would be equivalent to almost 3% of protein-coding genes. Many miRNAs are thought to be important in the regulation of gene expression. Typically, microRNAs are produced in precursor form and then processed to mature form by typically cleaving the 3' arm of the precursor stem-loop structure. Therefore, a precursor microRNA and a mature microRNA have identical 5' end but distinct 3' end. Selective end-labeling can be used to detect mature microRNA species without detection of precursor species by designing a capturing sequence complementary to the 3' end sequence. An example of selective end-labeling is described in the examples section.

Any of a variety of biological samples may be suitable for use with methods disclosed herein. Types of biological samples include, but are not limited to, cells, tissue, whole blood, plasma, serum, urine, stool, saliva, cord blood, chorionic villus samples amniotic fluid, and transcervical lavage fluid. Tissue biopsies of any type may also be used. Cell cultures of any of the afore-mentioned biological samples may also be used in accordance with inventive methods, for example, chorionic villus cultures, amniotic fluid and/or aminocyte cultures, blood cell cultures (e.g., lymphocyte cultures), etc. In some embodiments, biological specimens comprise diseased cells such cancer or tumor cells.

Thus, a typical biological sample suitable for the present invention contain heterogeneous nucleic acids, proteins or other biomolecules. In some embodiments, a biological sample contains a mixture of nucleic acids from different cell types (e.g., normal cells and diseased cells such as tumor cells). In some embodiments, a biological sample (e.g., blood, serum or plasma) contains a mixture of maternal nucleic acids and fetal nucleic acids.

In some embodiments, the present invention is used to detect target analytes that are present in low abundance or as rare events in a biological sample. In some embodiments, target analytes that may be detected by an inventive method of the present invention are present at a concentration ranging from 0.1 amol-10,000 amol. In some embodiments, the target analytes are present at a concentration below 10,000 amol, below 5,000 amol, below 1,000 amol, below 800 amol, below 600 amol, below 400 amol, below 200 amol, below 100 amol, below 50 amol, below 40 amol, below 30 amol, below 20 amol, below 10 amol, or below 1 amol. In some embodiments, the amount of target analytes detected by an inventive method of the present invention represents less than 1% (e.g., less than 0.5%, 0.1%, 0.01%, 0.001%, 0.0001%) of the total nucleic acids in a biological sample. In some embodiments, the amount of target analytes detected by an inventive method of the present invention represents less than 1% (e.g., less than 0.5%, 0.1%, 0.01%, 0.001%, 0.0001%) of the total nucleic acids in a biological sample. In some embodiments, the amount of target analytes detected by an inventive method of the present invention represents less than 1 out of a million of the total nucleic acids in a biological sample. In some embodiments, the amount of target analytes detected by an inventive method of the present invention represents less than 1 out of 10 million of the total nucleic acids in a biological sample. The target analytes may be detected in crude sample or may be detected as isolated or purified sample.

Scanning and Quantification

Objects (e.g., particles) described herein may be characterized using various methods. In particular, various methods involving flow-through scanning and/or static imaging can be used to detect objects (e.g., particles) bound with target analytes and/or to determine amount of the target analytes. Typically, target analytes attached to substrates are determined based on detection of signals. According to the present invention, signals "indicative of" a target analyte are typically associated with the identity of objects (e.g., particles) to which the target analyte is attached. For example, signals emanate from one or more detectably labeled probes or targets that becomes associated with signals indicative of one or more encoding regions of the objects bearing the probes or targets.

Figure 5:
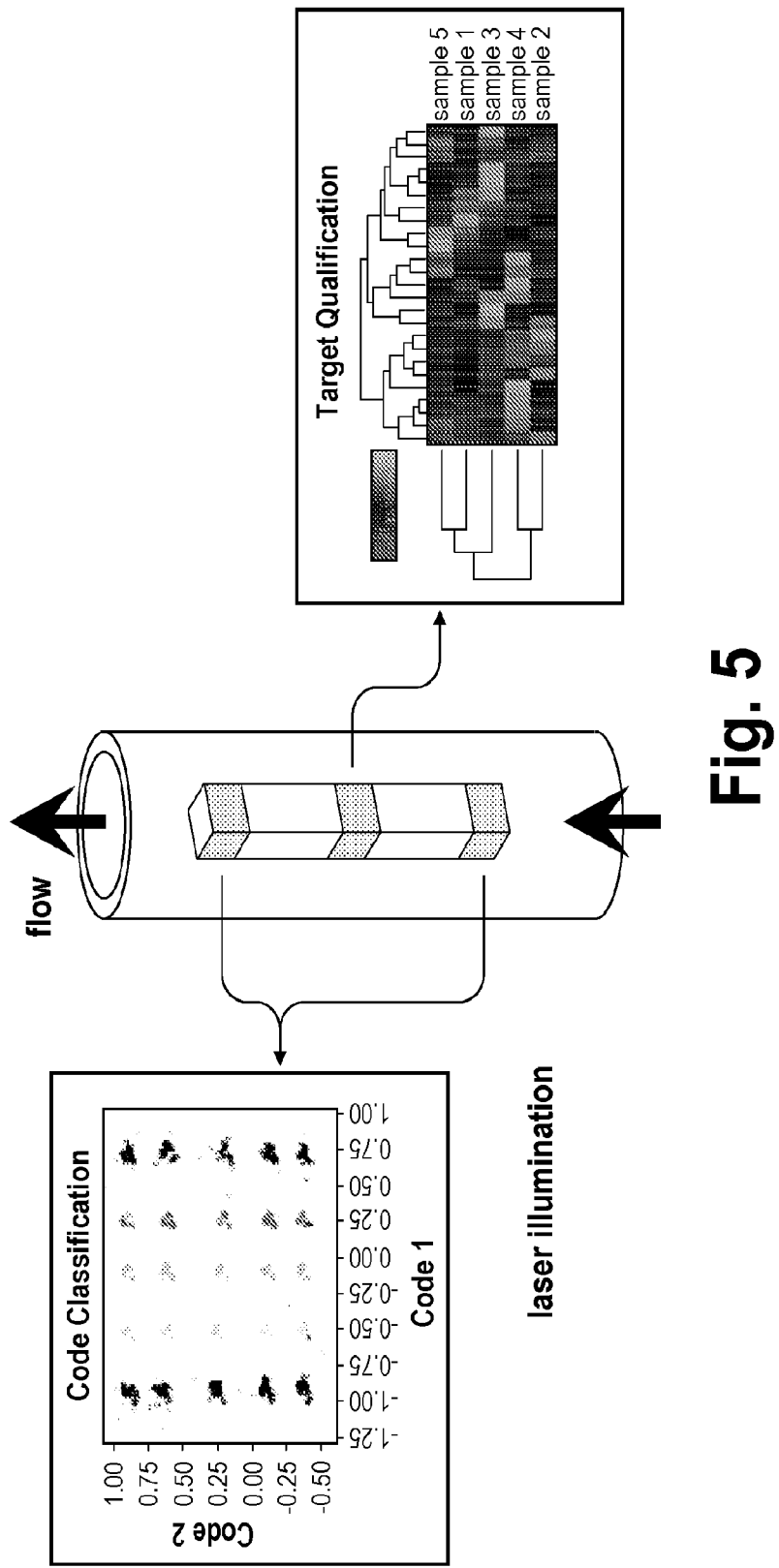
FIG. 5 illustrates an exemplary schematic of multi-color scanning with a flow cytometer.

In some embodiments, signals indicative of targets are generally distinguishable from signals indicative of identity of objects (e.g., particles). In some embodiments, probes or universal adapters specific for a target and encoding adapters for coding regions are labeled with distinctively detectable signals. For example, probes or universal adapters specific for the target may be labeled with fluorescent moieties that have a different emission spectrum (i.e., color and wavelength) than that of the fluorescent moieties with which the coding regions are labeled. Thus, in some embodiments, objects (e.g., particles) of the present invention can be scanned using a multi-scanning system involving more than one excitation sources and detectors (see FIG. 5).

Figure 6:
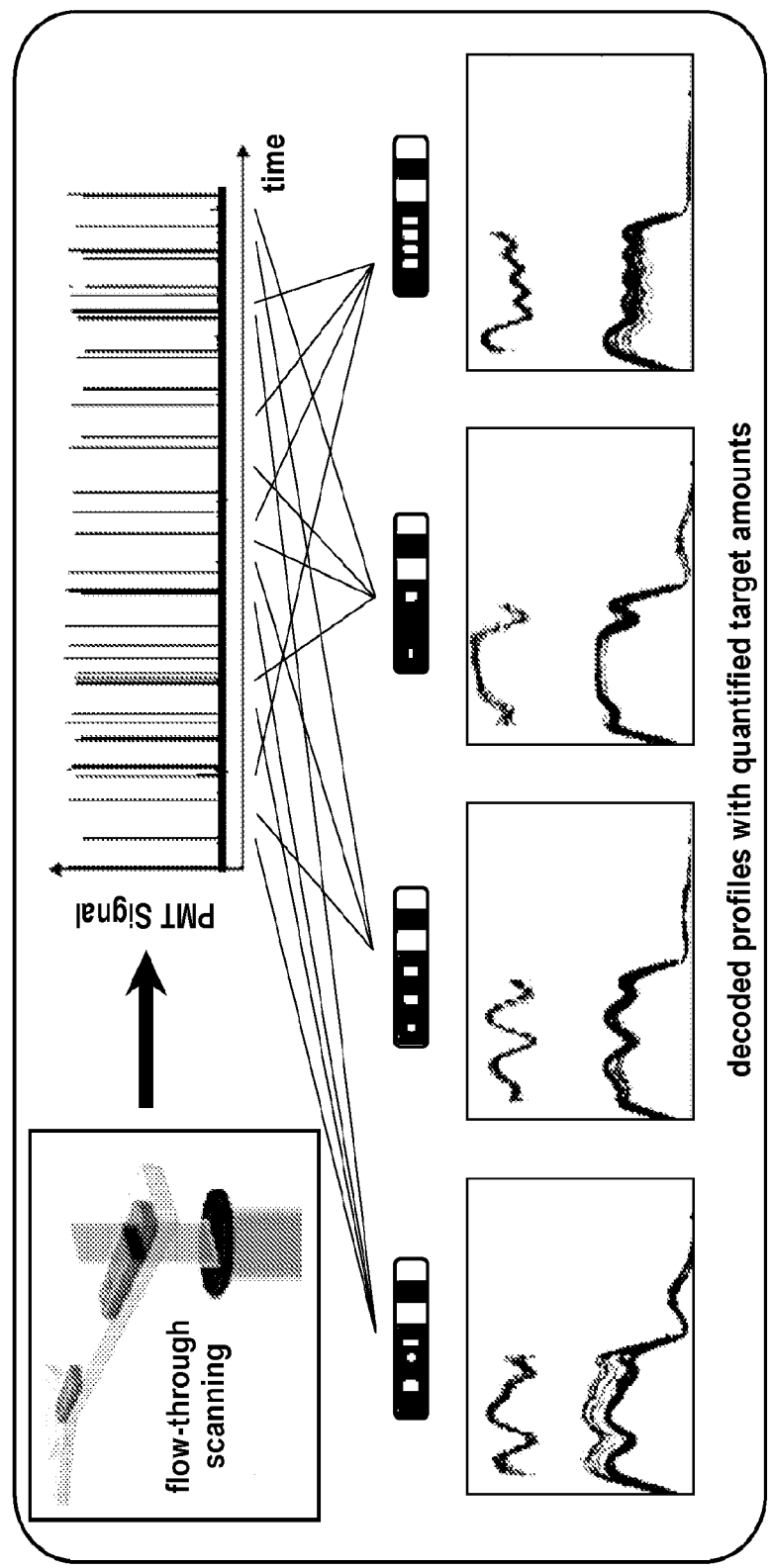
FIG. 6 illustrates an exemplary schematic of single-color scanning with a flow-through device.
Figure 7A:
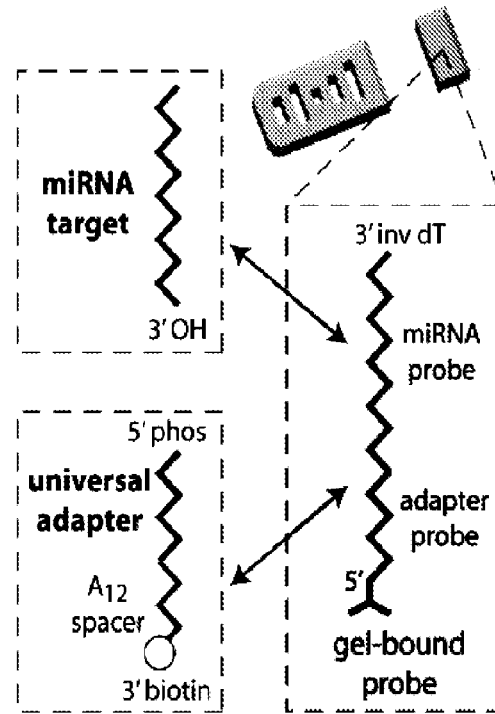
FIG. 7 illustrates exemplary post-hybridization miRNA labeling via ligation to a universal adapter. (a) DNA probes, lined at their 5' end throughout the probe region of encoded hydrogel particles, contain a miRNA specific sequence adjacent to a universal adapter sequence such that the 3' end of a captured target would abut the 5' end of a captured adapter oligonucleotide. The probe is capped with an inverted dT to mitigate incidental ligation and the adapter has a poly(a) spacer to extend its biotinylated 3' end away from the hydrogel backbone for efficient reporting. (b) After particles are hybridized with total RNA, T4 DNA streptavidin-phycoerythrin (SA-PE) is used as a fluorescent reporter. (c) the assay provides about atomole detection limits, defined at signal-to-noise=3. (d) single-nucleotide specificity is provided when synthetic let-7a RNA is spiked at 500 amol with particles bearing probes for let-7a, b, c, and d.
Figure 7B:
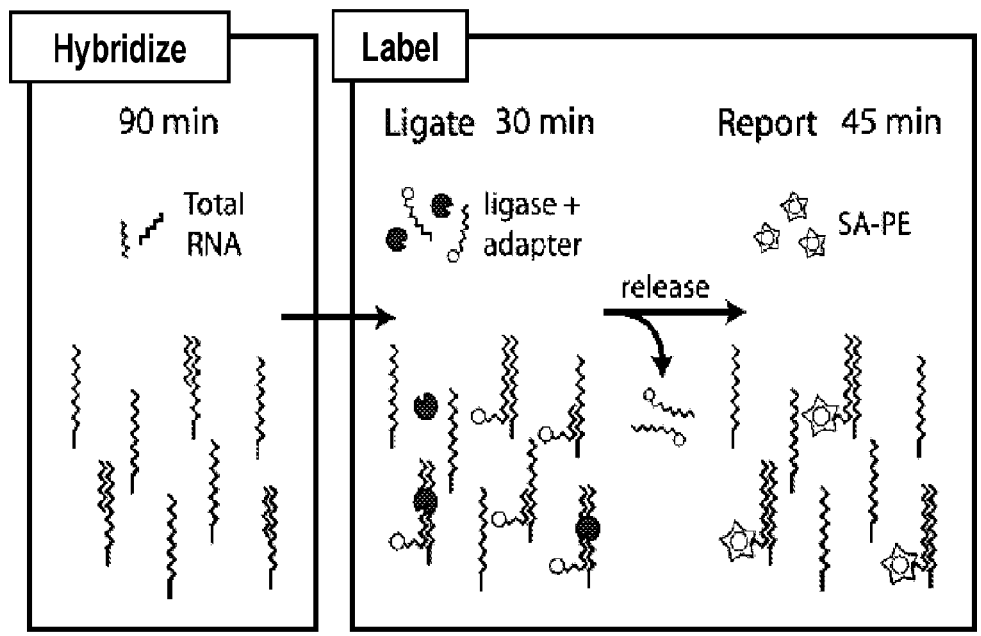
Figure 7C:
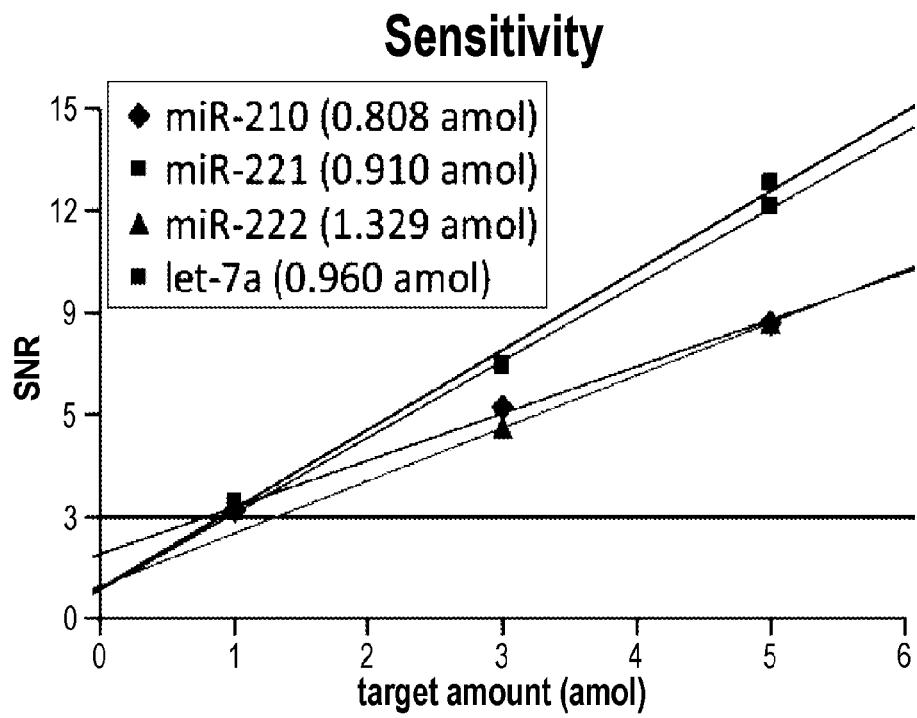
Figure 7D:
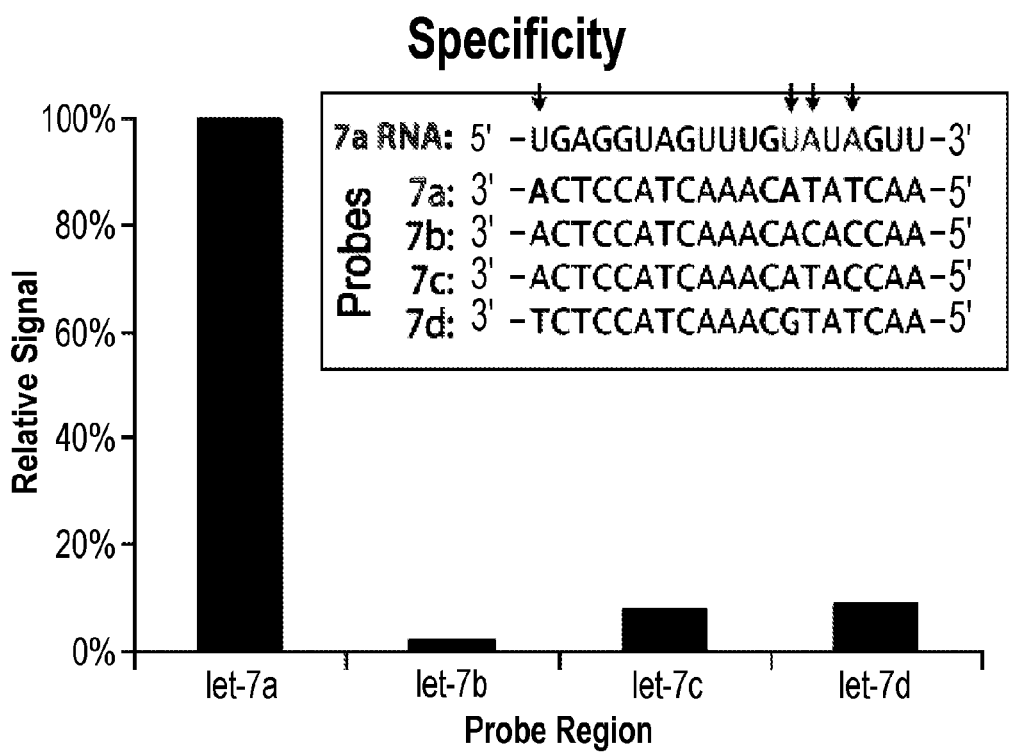

In some embodiments, single-color scanning is used. Signals indicative of separate "code" and "probe" regions are used to identify objects (e.g., particles) and capture targets, respectively. Using particles as examples, as described in detail below, signal patterns from the code regions (e.g., bearing holes, stripes, encoding adapters and/or combination thereof) of a particle serve as the basis for a graphical multiplexing barcode to identify the probe(s) in a particular particle. In some embodiments, unlike traditional bead-based systems that use optical encoding of spheres, an arrangement in which particles have multiple distinct regions makes single-color scanning possible, with only one excitation source and one detector required. In some embodiments, particles can bear graphical features (e.g., stripes, holes, or the like) with variable fluorescent intensities (of one or multiple wavelengths), optical properties, dimensions, etc (see FIG. 6).

Particles are used as examples to illustrate the scanning and quantification process in more detail below. However, methods described herein may be used with various other types of substrates or objects.

Interrogating Particles

In some embodiments, the present invention provides a method for characterizing multifunctional objects (e.g., particles) including one or more steps of (a) interrogating a plurality of objects (e.g., particles), wherein each individual object (e.g., particle) containing one or more interrogation regions detectable as a sequence of events; (b) recording multiple events, wherein each individual event corresponds to each individual interrogation region detectable above a pre-determined triggering threshold; (c) grouping the recorded multiple events, and (d) characterizing the plurality of objects based on the grouped events.

In some embodiments, particles are interrogated using image analysis in either static or flow-through settings. For high-throughput applications, it is desirable to scan the particles rapidly, preferably using existing commercial equipment. For example, flow cytometers are particularly useful for flow-through analysis of fluorescently labeled beads and particles, providing means for particle alignment, precise illumination, and accurate quantification of fluorescence emission. In some embodiments, encoded multifunctional particles are designed such that they can be scanned using commercially-available or custom designed flow-through device, such as, flow cytometers.

In some embodiments, particles suitable for flow-through scanning are engineered to mimic a series of cells (e.g., 2, 3, 4, 5, or more) that flow past an interrogation zone. In particular embodiments, outer regions (e.g., both end regions) of suitable particles are coding regions while one or more inner regions contain probes where the target is captured. Each coding region and probe region can be interrogated separately (e.g., sequentially or non-contemporaneously) and each region is also referred to as an interrogation region. In particular embodiments, rod-shaped particles that bear multiple interrogation regions are recorded as "events" using standard cytometry signal processing. By analyzing the sequence and time-proximity of such events, one can infer which ones belong in the same particle. These events can then be analyzed to decode the particle and quantify target bound to the probe region. Signal quantification can be achieved using fluorescence, light scattering, luminescence, etc.

Typically, raw signal is obtained from the cytometer detectors (or signal processing boards) using standard cytometery software. The signal can then be processed using custom software to import standard flow cytometery (FCS) files and reconstruct the events into particles and corresponding probe and coding regions.

Various flow-cytometery and other flow-through reading devices may be used in accordance with the present invention, including various commercially available flow-cytometers and customly designed devices. Exemplary suitable flow cytometers include, but are not limited to, Millipore Guava 8HT, Guava 5HT, Accuri C6, BD FACSCalibur, and among other cytometers.

Multiple-Event Particles

As a non-limiting example, when a particle travels through a cytometer's flow cell, it is excited with an illumination spot while detectors are used to monitor several parameters including forward scatter and side scatter of the illumination, and various wavelengths of emitted light. By setting a threshold on one of these parameters in a triggering channel, a user can define the instances that the cytometer software will record as events. If the signal from the detector in the triggering channel increases beyond the threshold level set by the user, the cytometery hardware and software will start to record an event—measuring the maximum signal height and integrated area from each detector while the triggering signal remains above the threshold. Events are typically reported with the height and area observed in each channel, along with the event width and a time-stamp of when the event occurred.

Typically, a single particle or bead is recorded as a single event. However, in many embodiments, particles according to the invention (e.g., rod-shaped particles) with multiple functional regions can be read as a sequence of distinct events. This is accomplished by using particles that have functional regions (for example: fluorescent) separated by inert regions (for example: non fluorescent). By incorporating threshold-triggering entities in the functional regions of the particles, but not in the inert regions, typical cytometery signal processing software records the functional regions as discrete events. This can be accomplished using entities that cause scatter or fluorescence. Such entities could include microparticles, nanoparticles, reflective monomers, metallic materials, fluorescently-labeled monomers, quantum dots, fluorescent dyes, carbon nanotubes, liquid crystals, and various detectable entities described herein.

An example is provided in the Examples section to illustrate how this approach works and the distinction from standard cytometery (Example 6). A example of particle scanning using a particular flow cytometery is provided in Example 7.

Data Analysis

For data analysis, an algorithm can be written to group events into particles, orients the particles, normalizes fluorescence against a standard if desired, and quantifies the fluorescence, scatter, or event width in each code and probe region. The corresponding code for each particle can then be given a confidence level, and those that were not called with a pre-defined level of confidence can be excluded from the analysis. The fluorescence in the probe region can then be used to determine the amount of target present in the sample analyzed. This system can be easily automated using software that performed analysis during or after scanning Grouping of Events In some embodiments, events are grouped based on spatial and temporal-proximity. In some embodiments, events are grouped based on patterns of measured properties for each event.

Typically, each event recorded by the cytometer is given a timestamp with a pre-determined resolution of, e.g., 1 ms, based on the flow rate in each cytometery. For example, as particles typically move at rates of ~1 m/s through the flow cell, the interrogation of a particle that is 200 μm long is expected to last ~0.2 ms. As such, it can be expected that the two events recorded from a single multifunctional particle would appear in the same timestamp.

In some embodiments, calibration beads are scanned fairly randomly throughout the course of data acquisition. Typically, at least one event is recorded for calibration beads. The multifunctional particles, on the other hand, typically show clustering of 2 or 4 events per timestamp, which lends very well to the theory that each particle is being read as two events. In addition, it can be clearly seen from the plots of event vs. time that during each timestamp, there is a high- and low-level fluorescence reading. The particles were designed to have one bright and one dim region of fluorescence in the FL-2 channel, which also gives support to the theory that each particle is being read as two discrete events. This approach can be applied to three or more events per particle as well. Each region/event can vary in terms of fluorescence level, forward or side scatter, and width.

In some embodiments, distinct levels of multiple fluorophores are incorporated into each code region of the multifunctional particles to further expand coding levels and increase encoding flexibility.

Various examples of particle scanning and quantification are provided in the Examples section.

Other Embodiments

There are several variations and alternate approaches to the embodiments described above. Although rod-shaped particles are used as examples described here, the present invention may be used to scan objects or particles with many other morphologies as well. For instance, particles may be anisotropic, have a head on one side, include rounded shapes, have holes in them, etc. In some embodiments, the present invention may be used to scan a variety of multifunctional entities including long nucleic acids, DNA origami, self-assembled structures, biological organisms, string-like objects, ribbon-like objects, etc. Furthermore, any combination of information recorded by the cytometer for each event, including height, area, width, or any combination thereof can be used for encoding or target quantification.

Other commercially-available instruments are capable of reading particles with multiple functional regions and can be used to practice the present invention. One example is an instrument capable of measuring changes in electrical conductance, or electrical resistance of a fluidic channel such as a Coulter Counter. The resulting current or voltage generated by a particle by a detector in such systems can be used to characterize particle size, shape, chemical composition, or surface properties. Additionally, laser-scanning cytometry (LSC), which allows high resolution visualization of particles in flow, may be used to identify the identifier regions and probe regions on particles with several functionalized regions. Such LSC systems are commercially available from companies such as CompuCyte. There also exist commercial cytometers that image cells/particles as they pass (eg. Amnis ImageStream). These can be used with suitable image-processing software to decode particles and quantify target. In addition, it may be possible to use non-fluorescent means of quantification such as surface-plasmon resonance or radiation.

Applications

Inventive methods described in the present application can be used in any detection applications, including antibody detection, displacement assays, nucleic acid measurement, enzyme measurement, to name but a few. According to the present invention, detection applications may include qualitative or quantitative detection and/or measurement.

In some embodiments, inventive methods according to the present invention are used to detect antibodies. Assays for antibody are widely used in medicine and clinical analysis for an wide variety of purposes, from detection of infections to determination of autoantibody.

In some embodiments, inventive methods according to the present invention are used in assays for many substances in a clinical laboratory, which are based on the interference with specific ligand-ligate or antigen-antibody interactions. For example, in some assays, one member of the ligand-ligate pair is labeled with a fluorophore and the other member is immobilized on particles. Soluble, unlabeled material (i.e., analyte) which may be ligand or ligate, is added to the reaction mixture to competitively inhibit interaction of the labeled component with the immobilized component.

In some embodiments, inventive methods according to the present invention are used in nucleic acid measurement. Multiplexed DNA analysis utilized in accordance with the present application can be applied to detect any PCR product or DNA/RNA sequences, for example, DNAs of interest for specific polymorphisms or mutations. With the multiplexed techniques provided by the present invention, individuals can be screened for the presence of histocompatibility alleles associated with susceptibility to diseases, mutations associated with genetic diseases, autoimmune diseases, or mutations of oncogenes associated with neoplasia or risk of neoplasia. In some embodiments, inventive methods according to the present invention are used to detect, measure and/or quantify various RNA species, including but not limited to, microRNA, mRNA.

In some embodiments, inventive methods according to the present invention are used in any formats for measurement of enzymes, enzyme inhibitors and other analytes. Enzymes that can be detected and measured using the invention include but are not restricted to, protease, glycosidase, nucleotidase, and oxidoreductase.

In general, samples that can be analyzed using methods according to the present invention include, but are not limited to, plasma, serum, tears, mucus, saliva, urine, pleural fluid, spinal fluid and gastric fluid, sweat, semen, vaginal secretions, fluid from ulcers and other surface eruptions, blisters, and abscesses, and extracts of tissues including biopsies of normal, malignant, and suspect tissues. Exemplary applications that can be used in accordance with the present invention are described in U.S. Pat. No. 5,981,180, the entire contents of which are incorporated herein by reference.

EXAMPLES

Example 1

Microparticle Synthesis

This example demonstrates that various microparticles can be synthesized for use according to the present invention. Exemplary methods are described in detail below.

Exemplary particle batches were synthesized in 38-μm tall polydimethylsiloxane (PDMS) microfluidic channels with the stop-flow lithography method. For the 12-plex study, code and inert buffer regions were polymerized from monomer solutions with 35% (v/v) poly(ethylene glycol) diacrylate (MW=700 g/mol) (PEG-DA 700), 20% poly(ethylene glycol) (MW=200 g/mol) (PEG 200), 40% 3×Tris-EDTA (TE) buffer (pH 8.0), and 5% Darocur 1173 photoinitiator. 1×TE and rhodamine-acrylate (1 mg/me were added to code monomer to give final concentrations of 9.4% and 0.6%, respectively. 1×TE and blue food coloring were added to buffer monomer to give final concentrations of 8.0% and 2.0%, respectively. Food coloring was used to visualize stream widths. Probe regions were polymerized from a different monomer solution that was added to acrydite-modified DNA probe sequences (Integrated DNA Technologies, IDT) suspended in 1×TE to give the desired final concentration of probe, 18% (v/v) PEG-DA 700, 36% PEG 200, and 4.5% Darocur; the remaining balance consisted of 3×TE.

In an effort to coarsely rate-match the binding of the targets used in this exemplary study, we incorporated the probe sequences at different concentrations in the particles (Table 1). As the characteristic time for target depletion scales with the inverse square root of probe concentration, a doubling of the binding rate for a given target will require a 4× increase in the amount of probe incorporated in a probe region of fixed size. In this exemplary study all rates were adjusted to match that of let-7a binding. Without being bound to any particular theory, it is contemplated that higher sensitivities and shorter assays could have been achieved by loading probe at maximum concentration. In this particular case, the goal was to develop a 12-plex assay with broad dynamic range and ~1 amol sensitivity for all targets.

TABLE 1

Exemplary particle codes and probe information for batches synthesized for 12-plex study. Final composition (v/v) of PEG-DA 700, PEG 200, and Darocur 1173 photoinitiator in prepolymer stream for probe were fixed at 18, 36, and 4.5%, respectively. Hairpin melting temperatures are listed in descending order, as calculated for the DNA-RNA duplex by IDT's OligoCalc application for the incubation conditions used in this exemplary study. For each miRNA, the relative binding rate was calculated using the average of target signals from 30- and 60-min incubations with 500 amol of target and ligation labeling. Short incubations were chosen to ensure the system had not reached equilibrium. Quoted probe concentrations refer to prepolymer stream composition. Approximately 11% of the probe in the prepolymer stream was covalently incorporated into the particles (Pregibon, D.C. et al., _Anal. Chem._ 81, 4873-4881 (2009)).

| Target | Probe Sequence | Hairpin Melting Temps (° C.) | Binding Rate Relative to let-7a for Probe Conc. of 50 μM | Adjusted Probe Concentration (μM) | Identifying Codes |
|---|---|---|---|---|---|
| let-7a | 5Acryd/GAT ATA TTT TAA ACT ATA CAA CCT ACT ACC TCA/3InvdT (SEQ ID NO: 1) | 38.0 | 1.00 | 50 | 31131, 32231, 31231, 32131, 31031 |
| miR-21 | 5Acryd/GAT ATA TTT TAT CAA CAT CAG TCT GAT AAG CTA/3InvdT (SEQ ID NO: 2) | 60.4, 52.9, 49.3, 46.6 | 0.45 | 247 | 31112, 32212, 31212, 32112, 31312 |

TABLE 1-continued

Exemplary particle codes and probe information for batches synthesized for 12-plex study. Final composition (v/v) of PEG-DA 700, PEG 200, and Darocur 1173 photoinitiator in prepolymer stream for probe were fixed at 18, 36, and 4.5%, respectively. Hairpin melting temperatures are listed in descending order, as calculated for the DNA-RNA duplex by IDT's OligoCalc application for the incubation conditions used in this exemplary study. For each miRNA, the relative binding rate was calculated using the average of target signals from 30- and 60-min incubations with 500 amol of target and ligation labeling. Short incubations were chosen to ensure the system had not reached equilibrium. Quoted probe concentrations refer to prepolymer stream composition. Approximately 11% of the probe in the prepolymer stream was covalently incorporated into the particles (Pregibon, D.C. et al., *Anal. Chem.* 81, 4873-4881 (2009)).

| Target | Probe Sequence | Hairpin Melting Temps (° C.) | Binding Rate Relative to let-7a for Probe Conc. of 50 μM | Adjusted Probe Concentration (μM) | Identifying Codes |
|---|---|---|---|---|---|
| miR-29b-2 | 5Acryd/GAT ATA TTT AAA ACA CTG ATT TCA AAT GGT GCT A/3InvdT (SEQ ID NO: 3) | 45.9, 44.7, 41.7 | 0.63 | 126 | 31132, 32232, 31232 32132, 31032 |
| miR-181b-1 | 5Acryd/GAT ATA TTT AAA CCC ACC GAC AGC AAT GAA TGT T/3InvdT (SEQ ID NO: 4) | 58.4, 43.2, 38.6 | 0.89 | 63 | 32230, 31130, 31230 32130, 31030 |
| miR-143 | 5Acryd/GAT ATA TTT TAG AGC TAC AGT GCT TCA TCT CA/3InvdT (SEQ ID NO: 5) | 55.2, 51.1 | 1.04 | 50 | 31110, 32210, 31210 32110, 31310 |
| miR-145 | 5Acryd/GAT ATA TTT AAA GGG ATT CCT GGG AAA ACT GGA C/3InvdT (SEQ ID NO: 6) | 47.4, 43.0, 36.6 | 1.01 | 50 | 31121, 32221, 31221 32121, 31321 |
| miR-146a | 5Acryd/GAT ATA TTT AAA ACC CAT GGA ATT CAG TTC TCA/3InvdT (SEQ ID NO: 7) | 64.6, 49.4, 48.3, 43.4 | 0.67 | 111 | 30001, 31101, 32201 31201, 32101 |
| miR-210 | 5Acryd/GAT ATA TTT TAT CAG CCG CTG TCA CAC GCA CAG/3InvdT (SEQ ID NO: 8) | 68.4, 65.6, 59.7, 55.4 | 0.90 | 62 | 31122, 32222, 31222 32122, 31322 |
| miR-221 | 5Acryd/GAT ATA TTT TAG AAA CCC AGC AGA CAA TGT AGC T/3InvdT (SEQ ID NO: 9) | 49.8, 43.6, 42.2, 41.0 | 0.82 | 62 | 31111, 32211, 31211 32111, 31311 |
| miR-222 | 5Acryd/GAT ATA TTT AAA CCC AGT AGC CAG ATG TAG CT/3InvdT (SEQ ID NO: 10) | 68.2, 68.1, 58.1, 47.5 | 0.62 | 130 | 31120, 32220, 31220 32120, 31320 |
| miSpike | 5Acryd/GAT ATA TTT AAA GAC CGC TCC GCC ATC CTG AG/3InvdT (SEQ ID NO: 11) | 66.5, 46.0 | 1.21 | 35 | 30002 31102 32202 31202, 32102 |
| RNU6B | 5Acryd/GAT ATA TTT AAA AAA ATA TGG AAC GCT TCA CGA ATT TGC GTG TCA TCC TTG CG/3InvdT (SEQ ID NO: 12) | 64.4, 58.4, 56.9, 56.1 | 0.95 | 55 | 30000, 31100, 32200 31200, 32100 |

Code, buffer, and probe prepolymer solutions were loaded into four-inlet microfluidic synthesis channels using modified pipette tips (Biosciences) as delivery chambers and forcing pressures of 4.5 psi. Hydrogel microparticles (250× 70×35 μm) were simultaneously synthesized, encoded, and functionalized at rates up to 16,000 per hour with 100-ms UV exposures (Lumen 200 at 75% setting, Prior Scientific) controlled by a shutter system (Uniblitz, Vincent Associates) interfaced with a custom-written Python automation script. Stream widths were adjusted such that code and probe regions spanned 140 and 40 μm, respectively, of the length of the particles. Buffer regions accounted for the remaining 70 μm of the length. We also showed that the same particle dimensions can easily accommodate two probe strips, with no loss in performance upon incubation, labeling, and scanning.

Following polymerization, particles were flushed down the synthesis channel and collected in a 1.7-ml Eppendorf tube containing 950 μl of TET (1×TE with 0.05% (v/v) Tween-20 surfactant (Sigma Aldrich)). Tween was added to prevent particle aggregation. Particles were next suspended in 200 μl of PEG 200 for 5 min and then rinsed with 700 μl of TET. This washing sequence was used to rinse the particles of unreacted PEG-DA, probe, and rhodamine. The wash sequence was repeated two more times and involved manual aspiration of supernatant facilitated by centrifugal separation of the dense particles. Particles were stored in TET at final concentrations of ~12.5 particles/μl in a refrigerator (4° C.).

Example 2 miRNA Incubation Experiments

This Example demonstrates typical sample incubation steps suitable for use in the present invention.

For all exemplary incubations studied, particles synthesized, for example, by the methods described in Example 1, were brought to room temperature prior to use, and each incubation was carried out in a total volume of 50 μl in a 0.65-ml Eppendorf tube with a final salt concentration of 350 mM NaCl and all twelve types of particle present (~360 particles/incubation tube). For calibration and specificity studies, a hybridization buffer (TET with assay-specific NaCl molarity) was first added to the Eppendorf tube, followed by all relevant target sequences (IDT) diluted in a mixture of 1×TE with 500 mM Nacl. Tween was excluded from the dilution buffer to prevent inaccuracies in pipetting steps that can arise from surfactant-induced changes in wettability. Depending on the assay type, either 1 μl of TET or 1 μl of *E. coli* total RNA (200 ng/μl) was introduced. For tissue profiling studies, hybridization buffer was added directly to a tube containing either 2.5 or 1.0 μl of previously frozen extracted total RNA (one individual per tissue type; stored at 100 ng/μl). Primary pair samples consisted of total RNA isolated from primary tumor and its adjacent normal tissue. Total RNA for all tissues was isolated by TRIzol purification; integrity of isolation was confirmed by checking for intact 18S and 28S ribosomal RNA. Lung sample (BioChain) was obtained from 50-year-old male with poorly differentiated squamous cell carcinoma. Breast sample (BioChain) was obtained from 53-year-old female with moderately differentiated invasive lobular carcinoma. Stomach sample (BioChain) was obtained from 70-year-old female with poorly differentiated adenocarcinoma. Pancreas sample (BioServe) was obtained from 65-year-old female with well-differentiated acina cell carcinoma. For all exemplary assays, 1 μl of miSpike (IDT) appropriately diluted in 1×TE with 500 mM NaCl was also introduced to give a total amount of 100 amol of the synthetic sequence to measure consistency of scanning/labeling and for quantification purposes. Prior to the addition of particles, incubation mixtures were heated to 95° C. for 5 min in a Multi-therm shaker (Biomega) and then brought back to room temperature over a 7 min period. A previously prepared master mix of particles (18 per μl) was thoroughly vortexed for 1 min, and 20 μl (~30 particles of each probe type) was introduced to each incubation tube. Incubation with target was carried out at 55° C. for 90 min in a thermomixer (Quantifoil Rio) with a mixing speed of 1800 rpm.

Following hybridization with target, samples were rinsed three times with a solution of 500 μl TET containing 50 mM Nacl. Supernatant was manually aspirated from the tube following centrifugal separation of the particles. All but 50 μl of solution was aspirated after the third rinse. Next, 245 μl of a previously prepared ligation master mix (100 μl 10×NEBuffer 2, 875 μl TET, 250 pmol of ATP, 40 pmol of universal adapter, and 800 U of T4 DNA ligase) was added to the tube. The mixture was placed in the Multi-therm shaker at 21.5° C. for 30 min with a mixing speed of 1500 rpm. Following ligation, an identical three-rinse cycle was performed. Streptavidin-r-phycoerythrin reporter (SA-PE, 1 mg/ml) was diluted 1:50 in TET and added to obtain a final dilution of 1:500. Samples were incubated in the Multi-therm unit at 21.5° C. for 45 min. After another three-rinse cycle, particles were additionally rinsed in 500 μl of PTET (5×TE with 25% (v/v) PEG 400 and 0.05% Tween-20), and then suspended in a final volume of 50 μl PTET for scanning. Prior to use, all PTET was sonicated for 5 mM to eliminate aggregations of polymer.

Example 3

Post-Hybridization Labeling

To generate a detectable signal indicating the presence and capture of nucleic acid targets, an exemplary post-hybridization ligation-based methodology is provided and demonstrated in this Example and Example 4 for labeling.

Such a post-hybridization method can be used to fluorescently label bound selected targets, e.g., miRNA targets. Existing approaches rely on the bulk-labeling of RNA using chemical or enzymatic means. These methods may suffer from high cost, the need for small-RNA purification and clean-up, sequence bias due to secondary structure, or complicated, time-consuming protocols. Here, we provide, for example, a two-step method to efficiently label targets after hybridization in about one hour.

Experimentally, we used T4 DNA ligase to link a universal oligonucleotide adapter to the 3' end of targets captured on gel-embedded DNA probes that act as a ligation templates (FIG. 7). As such, we can use a common, universal adapter to label multiple targets in a single reaction. The labeling process requires only a few simple steps. First, particles are hybridized with the sample, in this case total RNA, to capture appropriate targets in the particle probe regions. After excess sample is rinsed away, a ligation mix is added that includes the appropriate enzymes, all important co-factors (such as ATP), and a common biotinylated adapter. After a short reaction (typically 5-60 min) at room temperature, a low-salt buffer is used to rinse away any unreacted adapter. After rinsing away unreacted adapter, the particles are incubated with phycoerythrin-conjugated streptavidin reporter (SA-PE) to provide fluorescence. After another rinse, the particles can then be analyzed. More importantly, this labeling method was very efficient, had no minimal input RNA requirement, and showed no sequence bias for the targets used in this exemplary study (Examples 3 and 4). For each new miRNA target species, we incorporated a target-specific sequence into the universal probe template; complex modification and customization were not necessary.

In this arrangement, the adapter sequence was designed to minimize probe hairpin formation, which could retard target hybridization, and provide an adapter-probe melting temperature $T_m$ that was ~10-20° C. in ligation buffer. Although we used a reduced salt buffer during the rinse, the dehybridization of unreacted adapter can be accomplished using any condition that destabilizes nucleic acid interactions (low salt, high temperature, additives such as DMSO, PEG, or glycerol, etc.). Typically, we use SA-PE reporter to achieve maximum fluorescent signal. In addition or alternatively, a ligation-based labeling can be performed with adapters that are directly labeled with fluorophores or other reporting entities. Without being bound to any particular theory, it would be appreciated that this reduces the time and complexity of the assay. The process can be used, with appropriate probe and adapter design, to ligate adapters to the 3' end of DNA or RNA species containing a 3' OH, or at the 5' end of these species containing a 5' phosphorylation.

Example 4

Optimization and Variations of Ligation-based Labeling

In various embodiments, several aspects of the labeling technique described in the present invention were optimized, including probe/adapter design, reagent concentrations, rinse buffer salt content, ligation time, and ligation temperature. We show here the effects of ligation time and adapter tail length on labeling efficiency. The nucleic acid probes, targets, and adapters (all received from Integrated DNA Technologies, IDT) are given in the table below:

TABLE 2

Nucleic acid probes and targets used in optimization studies. Sequence in bold represents universal adapter-specific sequences, sequence in regular represents target-specific sequences, and sequence underlined represents poly(A) tails.

| Oligo Name: | Sequence/Modifications: |
|---|---|
| let-7a probe, DNA | /5Acryd/GATATATTTTAAACTATACAACCTACTACCTCA/3InvdT/ (SEQ ID NO: 13) |
| let-7a target, RNA | 5'-UGAGGUAGUAGGUUGUAUAGUU-3' (SEQ ID NO: 14) |
| UA10-Cy3, DNA | /5Phos/TAAAATATAT/3Cy3/ (SEQ ID NO: 15) |
| UA10-bio, DNA | /5Phos/TAAAATATAT/3Bio/ [poly(A) = 0] (SEQ ID NO: 16) |
| | /5Phos/TAAAATATAT<u>AAA</u>/3Bio/ [poly(A) = 3] (SEQ ID NO: 17) |
| | /5Phos/TAAAATATAT<u>AAAAAA</u>/3Bio/ [poly(A) = 6] (SEQ ID NO: 18) |
| | /5Phos/TAAAATATAT<u>AAAAAAAAAAAA</u>/3Bio/ [poly(A) = 12] (SEQ ID NO: 19) |

Adapter/Probe Design

Exemplary probes described above were designed to include a miRNA-specific region and an adapter-specific region, such that when bound, the 3' end of the miRNA target would abut the 5' end of the adapter. We chose to label the 3' end of miRNA targets because it has been demonstrated that when using a DNA template, the action of T4 DNA ligase in joining DNA to RNA molecules proceeds several orders of magnitude more rapidly at the 3' end of RNA versus the 5' end (Bullard, D. R. et al., *Biochem J* 398, 135-144 (2006)). The adapter sequence and length were chosen such that (1) the melting temperature was between 10-20 C in ligation buffer, (2) the sequence was not significantly self-complementary in order to avoid adapter hairpin or homodimer formation, and (3) complete DNA probes (with adapter and miRNA sequences) did not show appreciable hairpins for the miRNAs investigated.

Ligation Time

Figure 8:
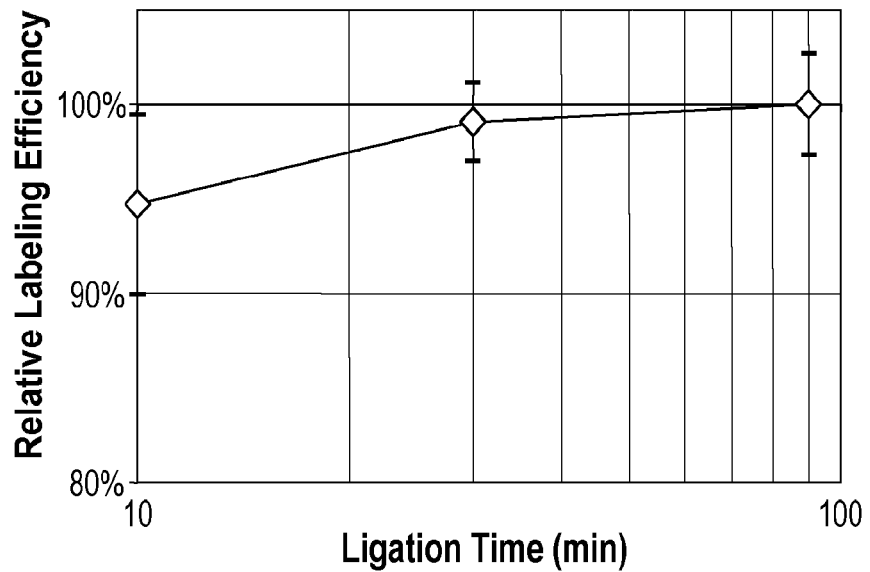
FIG. 8 illustrates an exemplary result showing relative ligation efficiency over time. Error bars represent the standard deviation taken over measurements from five particles.

We performed studies to determine the minimum ligation time needed for our labeling assay, using let-7a as a model system. Particles bearing a let-7a DNA probe region were incubated with 5 fmol synthetic let-7a RNA at 55 C for 110 min Particles were rinsed three times with phosphate buffered saline containing 0.05% Tween-20 (PBST, pH 7.4, Fluka) and incubated with 250 l of a ligation mix containing 200 U T4 DNA ligase, 40 nM Cy3-modified adapter (UA10-Cy3), and 0.05% Tween-20 in T4 DNA ligation buffer (NEB) for 10, 30, or 90 min at 16 C. After ligation, particles were rinsed three times in TE containing 0.025 M Nacl, deposited on a glass slide, and imaged using a CMOS camera (Imaging Source). We measured the fluorescence intensity in the probe region of each particle, subtracting the background fluorescence to get a target signal, which indicated ligation efficiency. The results are shown in FIG. 8

We calculated the relative efficiency by normalizing each signal by that obtained for the 90 min sample. As can be seen in Figure SD1, ligation is >95% complete even after a short 10-min reaction. For the experiments described in this work, we chose to use a ligation time of 30 min to ensure nearly complete ligation.

Tail Length for Biotinylated Adapters

The reporter streptavidin-phycoerythrin (SA-PE) is a large protein structure that has a radius of gyration on the order of ~10-15 nm. As such, when using biotinylated adapters with the SA-PE reporter, we found that it was beneficial to extend the biotin group away from the polymer backbone of the gel matrix. To do this, we used a poly(A) tail at the 3' end of the adapter and investigated the effect of tail length on target signal.

In this experiment, we used the same let-7a particles as in the previous section. We incubated with 50 amol let-7a miRNA for 60 min at 50 C. The particles were rinsed three times in PBST, and divided into four separate tubes. Particles in each tube were incubated for 30 min at room temperature with ligation mix containing 200 U T4 DNA ligase, and 40 nM UA10-bio (with either a 0, 3, 6, or 12 bp poly(A) tail), in 1×T4 DNA ligation buffer (NEB) with 0.05% Tween-20. After ligation, particles were rinsed three times in TE containing 0.05 M Nacl and 0.05% Tween-20. Particles were deposited on a glass slide and imaged using an EB-CCD camera. The target signals were compared to determine the effect of poly(A) tail length, as shown in FIG. 9.

Figure 9:
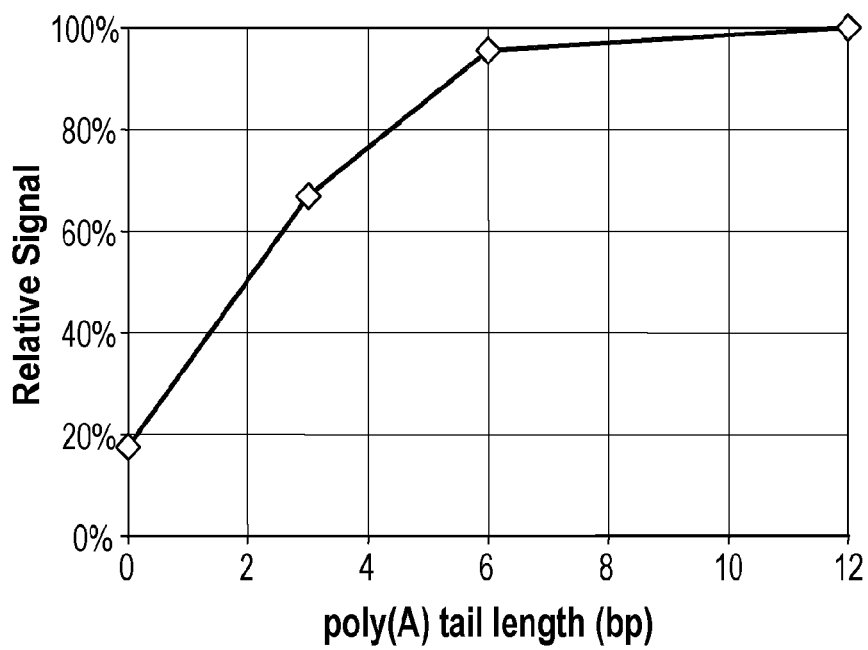
FIG. 9 illustrates an exemplary result showing effect of universal adapter poly(A) tail length on fluorescence signal when using biotinylated adapters with a streptavidin-phycoerythrin reporter. Signals are relative to that measured for a tail length of 12 bp.

As can be seen in FIG. 9, the length of the poly(A) tail has a large effect on target signal obtained. From zero to 12 bp, the signal increases ~5× but seems to level off at that point. For the experiments described in some examples, we chose to use universal adapters with poly(A) tail lengths of 12 bp.

Example 5 miRNA Profiling

The experiment described in this example demonstrates that compositions and methods provided in the present invention may be use for various applications (e.g., miRNA profiling).

Experimentally, this technique was proven by an investigation into the dynamic range, sensitivity, and specificity of the platform in the context of a 12-plex assay featuring ten clinically relevant miRNA targets. Because of its relative invariance across tissue types and disease states, RNU6B was used as an internal control for normalization purposes. We also used 100 amol of miSpike (a synthetic 21-mer) as an external control to validate the consistency of the labeling and scanning processes. We synthesized twelve batches of single-probe particles for this study. To compensate for discrepancies in target hybridization rates, we implemented a coarse rate-matching by tuning the probe concentration for each target using previously determined scaling laws (Table 1). To fully demonstrate the versatility of the scanner, five separate codes were correlated to particles of each probe type, thereby simulating a 60-plex assay.

Figure 10A:
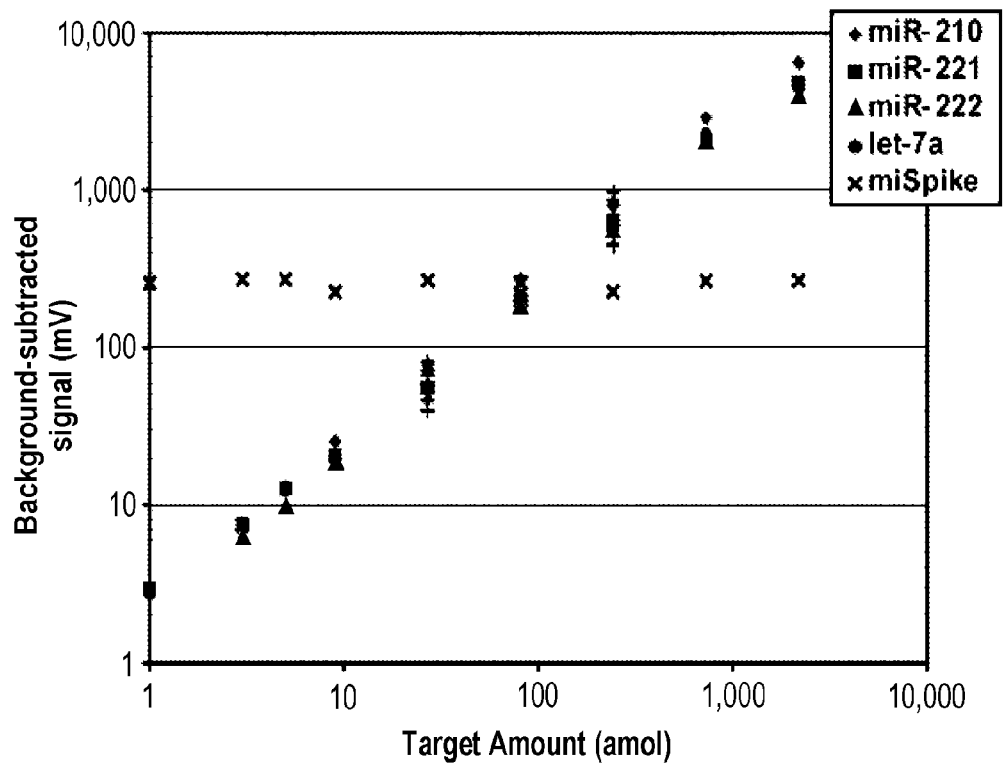
FIG. 10 illustrates an exemplary system performance in 12-plex assay. (a) Calibration curves for particle batches, with background-subtracted signal plotted against spiked target amount. miR-210, -221, -222 and let-7a were spiked into the same incubation mixes at the indicated amounts. the remaining seven naturally-occurring targets ('+' symbols) were spiked into the 27- and 243-amol trials to validate performance. For all trials, 200 ng of $E.\ coli$ total RNA was also spiked in for complexity. Mean COV of target level is 6.35% when considering target levels greater than 5 amol. Each point represents, on average, 19 particles from a single run. (b) Specificity of let-7a probe in the presence of sequences closely related to intended target (see inset box for target set). We observed a maximum cross-reactivity of only 27%. (c) Cancer profiling results for four types of human tissue. Error bars represent standard deviation in triplicate measurements on aliquots of the same single-patient sample. Amount of total RNA used in assays is 250 ng, unless otherwise noted.
Figure 10B:
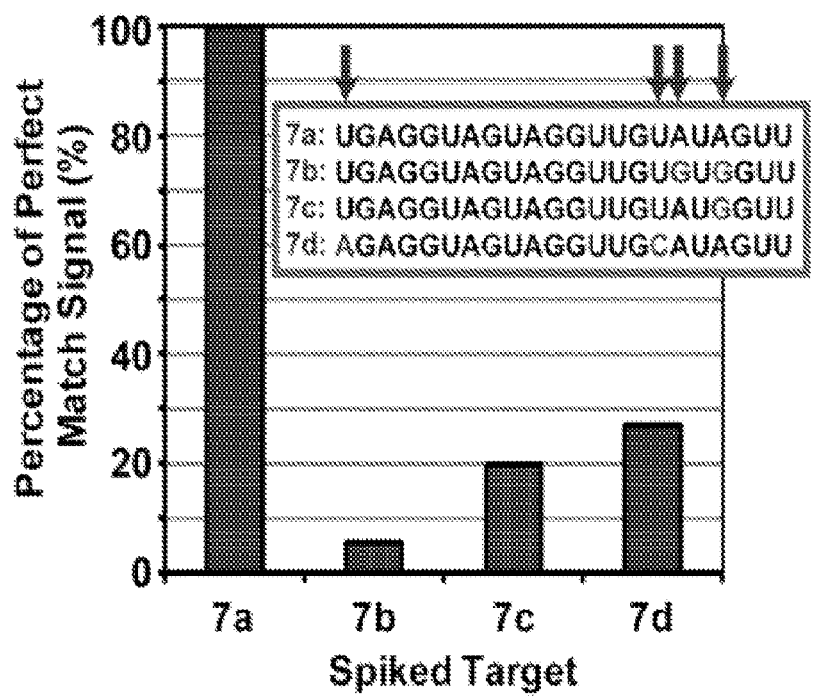
Figure 10C:
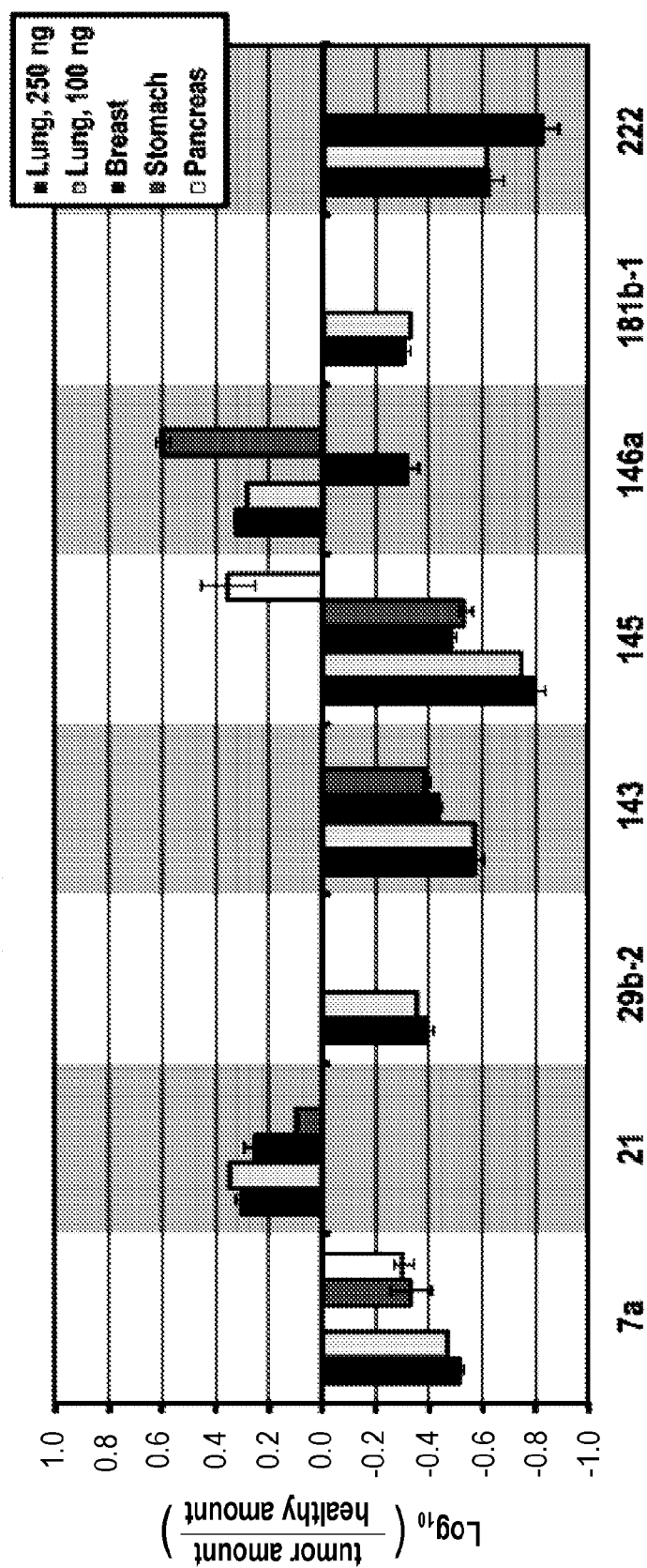
Figure 11A:
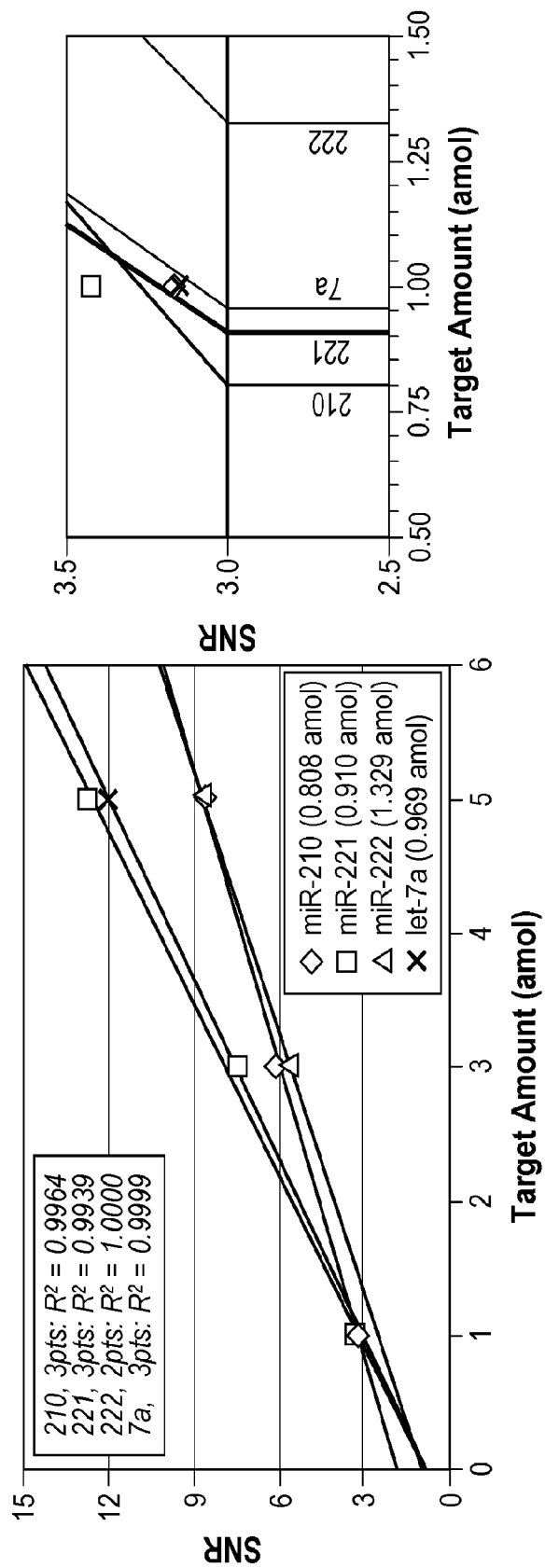
FIG. 11 illustrates exemplary results showing limit of detection calculations and calibration curves for neat samples. (a) Extrapolation of SNR for determination of limit of detection (LOD). The LODs of the four calibration targets (see legend) were calculated by finding the target amount at which the SNR was three. Regression lines with a mean Pearson coefficient of 0.9965 (excluding miR-222) were used to extrapolate LODs. (b) Calibration curves for particle batches incubated without spiked $E.\ coli$ total RNA. Except for the absence of $E.\ coli$ RNA, conditions are identical to those used to construct FIG. 3a. (c) Comparison of background-subtracted signals from neat and $E.\ coli$ calibration measurements. clustering of points around the identity line (red) indicates highly specific detection with no noticeable decrease in binding rates in more complex samples. For all plots, all target levels (except miSpike) have been adjusted for comparison purposes by using the background-subtracted signal from the 100-amol miSpike profiles.
Figure 11B:
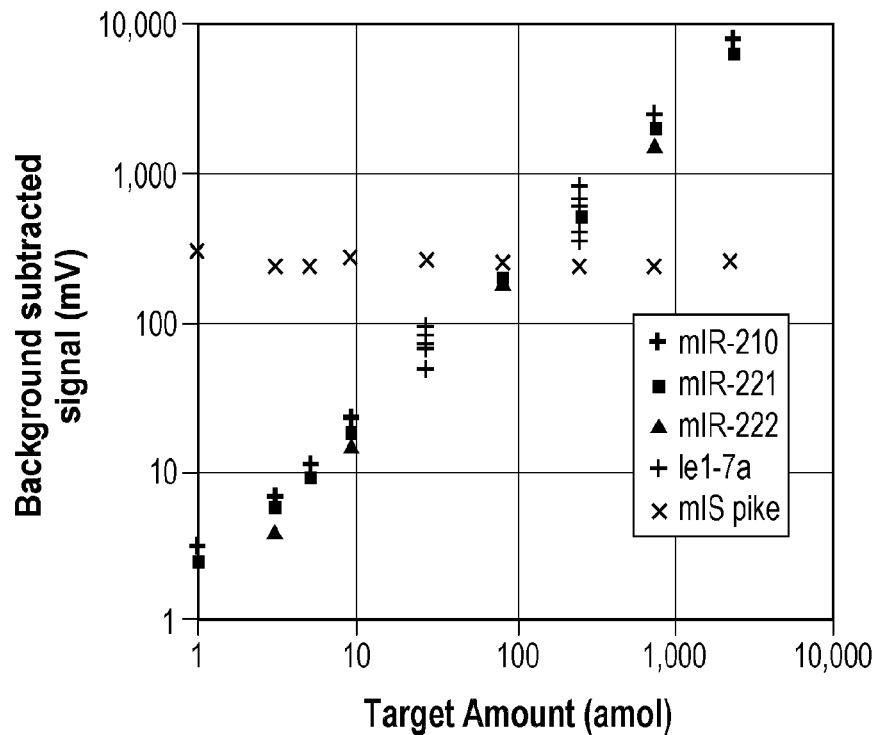
Figure 11C:
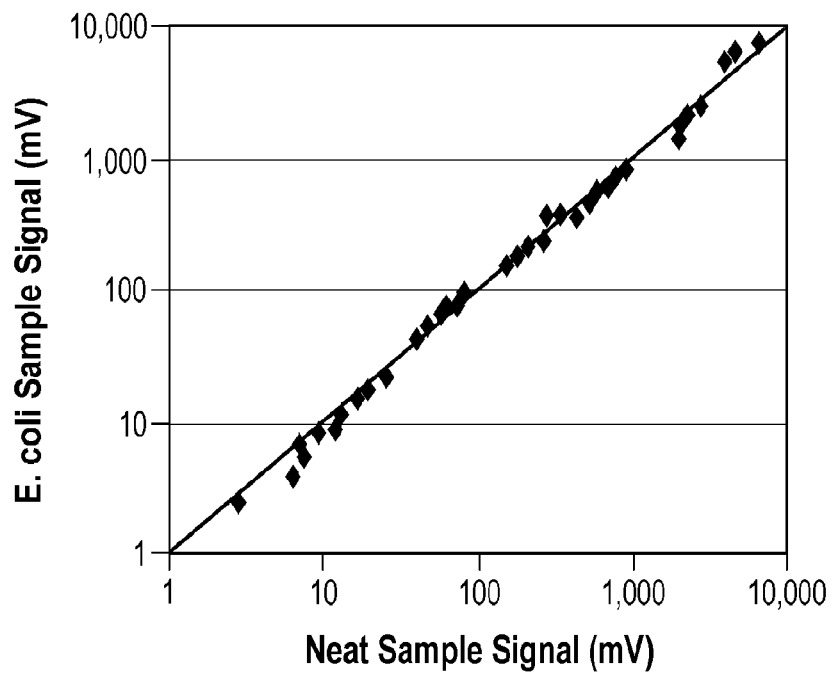
Figure 12:
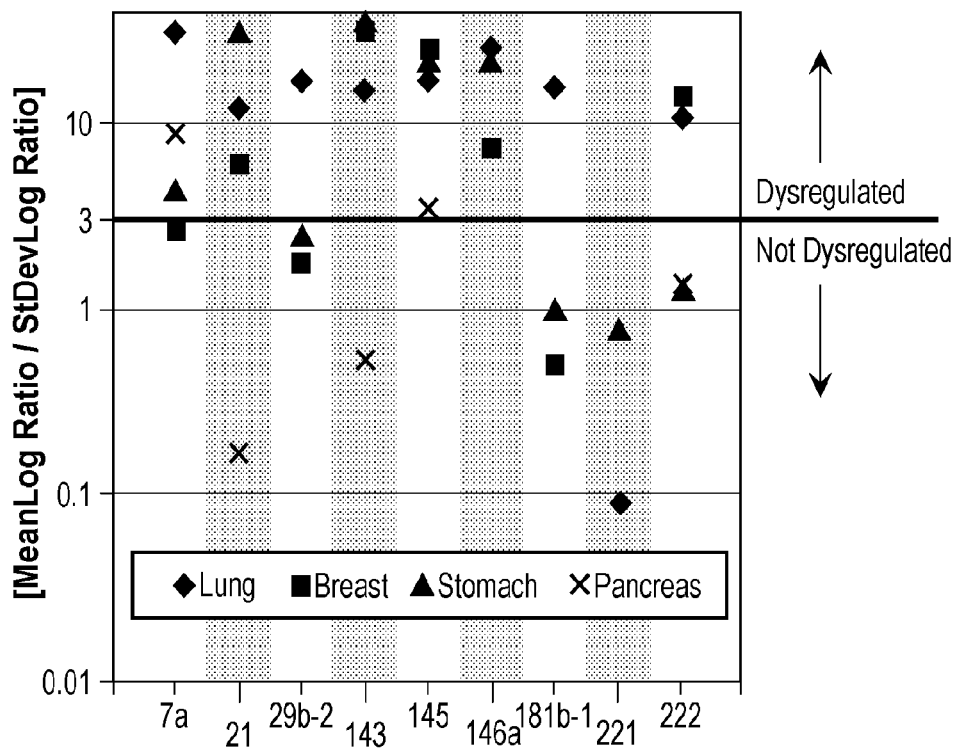
FIG. 12 illustrates an exemplary dysregulation classification. A SNR was used to distinguish dysregulated targets in tissue profiling. The mean and standard deviation of the log-transformed expression ratio were calculated for each target in each tissue for the triplicate assays. A SNR of three was chosen as the threshold for dysregulation. All 20 instances of dysregulation matched observations in the literature
Figure 13:
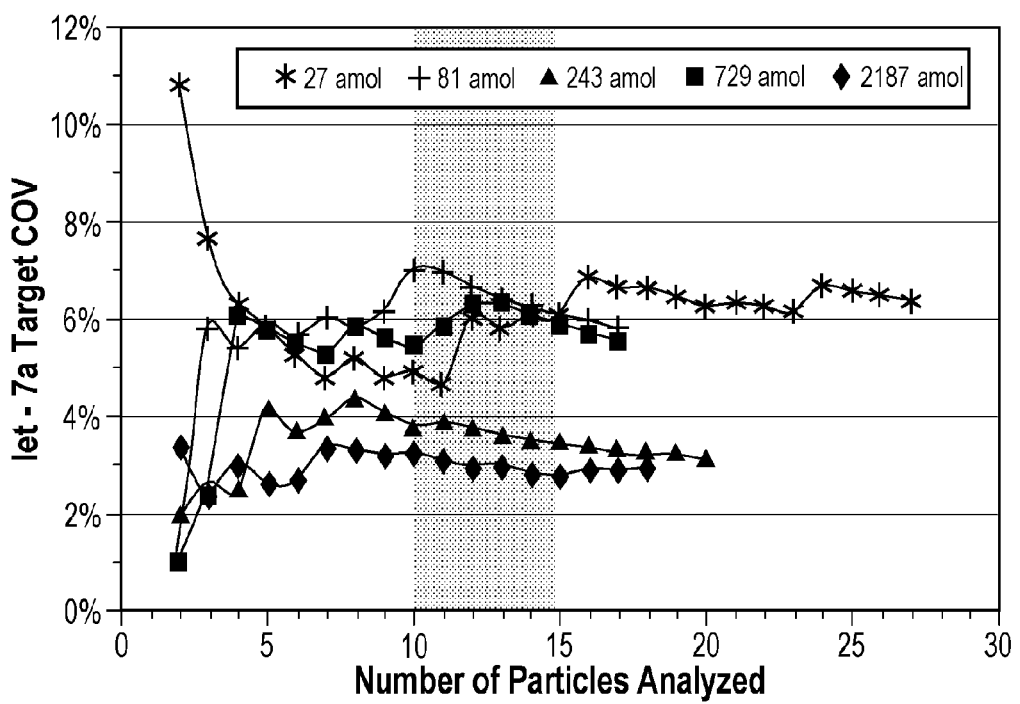
FIG. 13 illustrates exemplary results showing coefficient of variation (COV) of target level as a function of number of particles analyzed. The COV of the target level for let-7a in the $E.\ coli$ calibration scans was seen to stabilize to a nearly constant value in the 10-15 particle window for the five spike-in amounts presented above.

To further assess the sensitivity and dynamic range of our system, we simultaneously spiked four of the twelve targets into 50-μl incubation mixes at amounts ranging from 1 to 2187 amol. We observed a linear detector response over four logs, with sub-attomole sensitivity achieved for three of the four targets and strong agreement between neat samples and those spiked with 200 ng of *E. coli* total RNA to add complexity (FIG. 10 and FIG. 11). By comparison, existing bead-based approaches have a 200-amol limit of detection and only one log of range. To assess specificity, we performed assays with let-7a particles and four members of the let-7 family spiked separately at 200 amol into samples containing 200 ng *E. coli* total RNA. Scans revealed a maximum cross-reactivity of 27% (FIG. 10*b*), which is lower than other systems (microarray ~50%) and can be dramatically improved with lower hybridization salt concentrations ((FIG. 12). These assays were very reproducible, with intra- and inter-run COV's of 2-7% (Table 3). Due to limitations in detection and particle preparation, it is common for users of current bead-based systems to employ 4,500 copies of each type of bead in an assay for high-confidence estimates of target level. By contrast, we found it sufficient to analyze only 10-15 hydrogel particles for each probe type (FIG. 13).

TABLE 3

Intra-run COVs in target level for *E. coli* calibration curve. All entries are percentages with each statistic calculated using 19 particles on average. miR-222 exhibited a limit of detection over 1 amol. Inter-run COV in background-subtracted miSpike signal (100 amol) for the nine represented scan sets was 6.84%.

| Target | 1 amol | 3 amol | 5 amol | 9 amol | 27 amol | 81 amol | 243 amol | 729 amol | 2187 amol |
|---|---|---|---|---|---|---|---|---|---|
| miR-210 | 59.45 | 29.22 | 10.88 | 10.93 | 1.81 | 5.91 | 1.39 | 5.85 | 1.93 |
| miR-221 | 36.71 | 9.95 | 21.80 | 18.41 | 4.11 | 7.20 | 2.79 | 6.81 | 2.01 |
| miR-222 | — | 5.96 | 16.10 | 15.62 | 4.85 | 5.25 | 3.26 | 5.93 | 3.27 |
| let-7a | 87.99 | 19.18 | 26.77 | 18.83 | 5.20 | 5.83 | 3.13 | 5.53 | 2.93 |

As a further validation of the platform, we performed expression profiling across tumor and adjacent normal tissue for several cancer types. As anticipated, we observed the dysregulation of several miRNA targets in all of the diseases investigated (FIG. 10*c*, Table 4, and Table 5). Although we used 250 ng of total RNA for these samples, similar results were obtained for lung samples using only 100 ng, suggesting that less input RNA would be sufficient. With a total assay time of only 3 h, the profiling is more efficient than microarray approaches (~24 h) and exhibits sensitivity and reproducibility far superior to that of existing bead-based methods.

TABLE 4

Mean target amounts and inter-run COVs in target amount for 250-ng tissue profiling replicates. Top number in each entry is mean amount for replicate trials (amol); bottom number in parentheses is the inter-run COV (%). Amounts were determined by comparison to the background-subtracted 100-amol miSpike signal from each run. Replicate assays were conducted on different days to rigorously test reproducibility. Each statistic was calculated using 16 particles on average. Entry spots lacking data indicate that target was not present above the 2 amol cutoff.

|  | let-7a | miR-21 | miR-29b-2 | miR-181b-1 | miR-143 | miR-145 | miR-146a | miR-210 | miR-221 | miR-222 | RNU6B |
|---|---|---|---|---|---|---|---|---|---|---|---|
| Lung Tumor | 594.81 (3.18) | 1498.85 (10.57) | 68.36 (10.52) | 7.02 (21.45) | 85.61 (10.55) | 162.88 (6.05) | 77.02 (8.28) | — | 7.21 (8.09) | 8.13 (8.22) | 57.16 (7.46) |
| Lung Healthy | 368.08 (13.97) | 141.70 (12.10) | 31.80 (8.43) | 2.69 (18.61) | 59.79 (10.54) | 189.07 (8.98) | 6.95 (12.61) | — | — | 6.45 (12.33) | 10.84 (10.65) |
| Breast | 1094.19 | 808.08 | 65.88 | 3.71 | 32.48 | 73.53 | 9.26 | — | — | 2.29 | 116.88 |

TABLE 4-continued

Mean target amounts and inter-run COVs in target amount for 250-ng tissue profiling replicates. Top number in each entry is mean amount for replicate trials (amol); bottom number in parentheses is the inter-run COV (%). Amounts were determined by comparison to the background-subtracted 100-amol miSpike signal from each run. Replicate assays were conducted on different days to rigorously test reproducibility. Each statistic was calculated using 16 particles on average. Entry spots lacking data indicate that target was not present above the 2 amol cutoff.

|  | let-7a | miR-21 | miR-29b-2 | miR-181b-1 | miR-143 | miR-145 | miR-146a | miR-210 | miR-221 | miR-222 | RNU6B |
|---|---|---|---|---|---|---|---|---|---|---|---|
| Tumor | (6.82) | (9.96) | (9.99) | (5.01) | (7.48) | (11.20) | (4.75) | — | — | (16.14) | (0.19) |
| Breast | 912.95 | 302.39 | 32.87 | 2.65 | 59.01 | 149.06 | 12.90 | — | — | 10.20 | 78.55 |
| Healthy | (6.30) | (5.81) | (25.08) | (6.96) | (8.52) | (9.57) | (5.89) | — | — | (2.59) | (3.05) |
| Stomach | 270.64 | 561.87 | 68.78 | 2.28 | 169.45 | 388.39 | 29.66 | — | 2.93 | 14.15 | 175.69 |
| Tumor | (8.96) | (13.76) | (19.21) | (11.03) | (3.99) | (9.16) | (2.89) | — | (22.98) | (8.16) | (8.52) |
| Stomach | 258.28 | 204.24 | 73.44 | — | 186.39 | 597.31 | 3.33 | — | — | 7.83 | 78.45 |
| Healthy | (4.62) | (24.90) | (1.78) | — | (16.68) | (17.91) | (10.20) | — | — | (5.76) | (9.26) |
| Pancreas | 44.96 | 14.96 | 9.95 | — | 5.43 | 22.63 | — | — | — | — | 9.49 |
| Tumor | (2.62) | (12.21) | (17.82) | — | (58.64) | (11.60) | — | — | — | — | (8.23) |
| Pancreas | 98.10 | 18.21 | 14.85 | — | 6.79 | 10.88 | — | — | — | — | 10.33 |
| Healthy | (2.64) | (48.23) | (11.77) | — | (27.57) | (7.42) | — | — | — | — | (7.81) |

TABLE 5

Log-transformed expression ratios for 250-ng assays. Top number in each entry is the mean of the log-transformed ratios of tumor amount-to-healthy amount of the indicated target in the specified tissue over three trials; bottom number in parentheses is the standard deviation. Entry spots in red indicate dysregulation. Entry spots lacking data indicate that the ratio was not calculated.

|  | let-7a | miR-21 | miR-29b-2 | miR-143 | miR-145 | miR-146a | miR-181b-1 | miR-222 |
|---|---|---|---|---|---|---|---|---|
| Lung | −0.5119 | 0.3020 | −0.3911 | −0.5670 | −0.7870 | 0.3232 | −0.3066 | −0.6210 |
|  | (0.0161) | (0.0245) | (0.0225) | (0.0364) | (0.0450) | (0.0127) | (0.0194) | (0.0364) |
| Breast | −0.0942 | 0.2532 | 0.1378 | −0.4318 | −0.4801 | −0.3168 | −0.0266 | −0.8253 |
|  | (0.0349) | (0.0416) | (0.0777) | (0.0137) | (0.0194) | (0.0433) | (0.0529) | (0.0591) |
| Stomach | −0.3310 | 0.0966 | −0.3844 | −0.3877 | −0.5336 | 0.6007 | 0.3294 | −0.0935 |
|  | (0.0747) | (0.0031) | (0.1547) | (0.0107) | (0.0252) | (0.0282) | (0.3374) | (0.0716) |
| Pancreas | −0.3023 | −0.0198 | −0.1402 | −0.1251 | 0.3534 | — | — | 0.1785 |
|  | (0.0345) | (0.1183) | (0.0778) | (0.2381) | (0.1019) | — | — | (0.1382) |

This high-performance nucleic acid profiling system and platform is therefore shown to employ a versatile scanning and labeling methodology that enables the use of graphically-encoded hydrogel microparticles. The system's unprecedented combination of sensitivity, flexibility, and throughput offer exciting possibilities for discovery and clinical applications, particularly in the quantification of low-abundance miRNA and other biomolecules in readily-accessible media like serum.

Example 6

Scanning of Multiple-Event Particles

Figure 14:
FIG. 14 illustrates a conceptual example of how scanning of multifunctional particles could be implemented. Standard cytometry records "events" as instances where the signal from a selected detector breaks a threshold, recording single beads as single events, and saving data for each channel.
Figure 14:
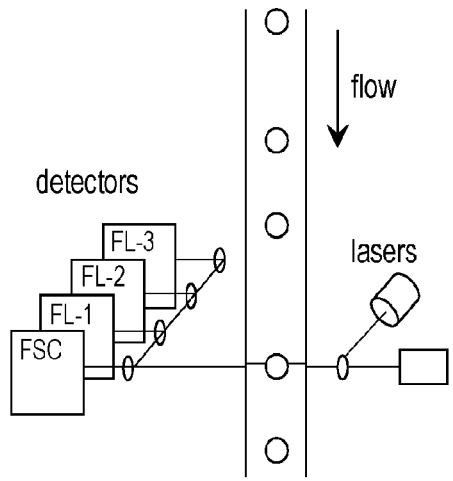
Figure 14:
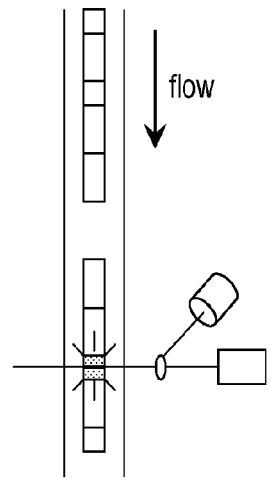
Figure 14:
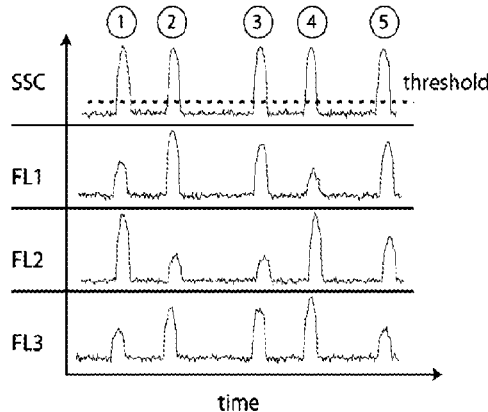
Figure 14:
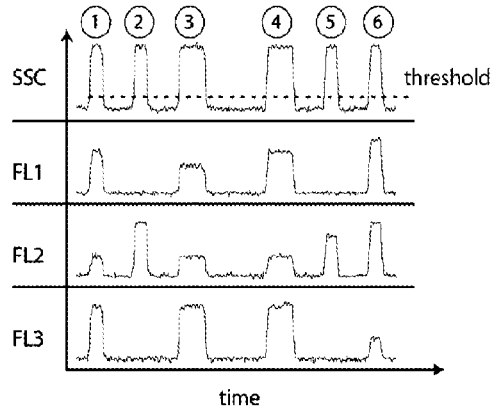

An example of how our approach is distinguished from standard cytometery is shown in FIG. 14 below. In this example, the functional regions of multifunctional particles can be loaded with entities that cause scatter of the illumination, which in turn triggers the cytometer to record an event.

We show a particle architecture that has two encoding regions and a single probe region where target is captured. The two code regions have varying levels of fluorophores embedded to give distinct signatures of fluorescence in the three fluorescence channels. One code regions is intentionally wider than the other in order to indicate particle orientation. The target could be labeled with a fluorophore that preferentially appears in a single fluorescence channel, as shown. In this example, each particle would be reported as 3 events. Of these three, the first and last would give code information while the second event would be used for target quantification. In this manner, the code and captured target are quantified non-contemporaneously.

We performed preliminary experiments to demonstrate the implementation of this methodology. We synthesized multifunctional particles that were ~200×35×30 μm with two fluorescent regions (30 μm and 60 μm, each dyed with Cy5 and Cy3 fluorescent dyes) flanking a broad inert region. The particles were run through an Accuri C6 cytometer with a flow rate of 100 μl/min and a core size of 40 μm. The threshold was set at 100,000 on FL4-H (which detects Cy5).

Each event recorded by the cytometer is given a timestamp with a resolution of 1 ms. As particles typically move at rates of ~1 m/s through the flow cell, the interrogation of a particle that is 200 μm long is expected to last ~0.2 ms. As such, it can be expected that the two events recorded from a single multifunctional particle would appear in the same timestamp. To show that each particle was being read as two separate events, we plotted a histogram showing the count of timestamps that had a given number of events. We would expect the number of events per timestamp to be even for our particles (2 events for a single particle, 4 events for two particles, etc.), and both odd and even for regular particles. As a control, we also ran standard Accuri 8-peak calibration beads, with a typical spherical shape. The results are shown in FIG. 15.

As can be seen, the calibration beads are scanned fairly randomly throughout the course of data acquisition, giving a range from 1-4 beads/timestamp. The multifunctional particles, on the other hand, show clustering of 2 or 4 events per timestamp, which lends very well to the theory that each particle is being read as two events. In addition, it can be clearly seen from the plots of event vs. time that during each timestamp, there is a high- and low-level fluorescence reading. The particles were designed to have one bright and one dim region of fluorescence in the FL-2 channel, which also gives support to the theory that each particle is being read as two discrete events. This approach can be applied to three or more events per particle as well. Each region/event can vary in terms of fluorescence level, forward or side scatter, and width.

In some cases, it is useful to incorporate distinct levels of multiple fluorophores into each code region of the multifunctional particles. As a proof-of-concept, we used rod-shaped particles, 200×35×30 µm, with a single 60 µm code region on one end. The code region was labeled using four distinct levels of Cy3 and Cy5 fluorescent dyes. Particles were analyzed using the Accuri C6 cytometer with a flow rate of 100 µl/min, a core size of 40m, and a threshold of 5000 on FL4. The results are shown in FIG. 16 below.

The plot in FIG. 16 shows that it is possible to create a distinct fluorescent fingerprint in each code region of multifunctional particles. Each cluster of data points represents a distinct code.

For data analysis using this approach, an algorithm will be needed that groups events into particles, orients the particles, normalizes fluorescence against a standard if desired, and quantifies the fluorescence, scatter, or event width in each code and probe region. The corresponding code for each particle can then be given a confidence level, and those that were not called with a pre-defined level of confidence can be excluded from the analysis. The fluorescence in the probe region can then be used to determine the amount of target present in the sample analyzed. This system can be easily automated using software that performed analysis during or after scanning Example 7

Reading of Raw Signal

This Example demonstrates interrogating multifunctional particles in standard flow cytometers. In some embodiments, interrogation is performed to acquire signal from a cytometer detector before it is processed into events by the machine's firmware and use custom software to identify, orient, and analyze particles scans. We performed proof-of-concept scanning of particles in this manner, using three separate cytometers from Partec, Accuri (C6), and Millipore (Guava).

To gather raw data, we used the leads (Partec and Millipore) or QC pin (Accuri) from a single PMT in each cytometer, connected them through a simple circuit (often just a single resistor), and measured the voltage using a standard data acquisition (DAQ) board (National Instruments NIDAQ-USB6250). A custom script written in Python was used to communicate with the DAQ board, allowing the user to input how many samples to acquire and at what frequency. Samples were taken at rates ranging from 60 kHz to 1 MHz. After acquisition, the data were stored in a single file.

For analysis, we applied Fast-Fourier-Transform-based filtering to isolate the desired frequency response for each scan. Then, particles were identified in each sample by setting a threshold. If the signal was found to be above the threshold for a predefined number of samples, the region of interest and its flanking data points were stored as a single particle scan. Design features built in to each particle were used to identify code and probe regions. In addition, each signal could be normalized by a given feature on each particle. Our barcodes in this example consisted of series of stripes along the particle that had varying levels of fluorescence.

We used a standard set of test particles to assess alignment and consistency of particle-to-particle scan in three commercial cytometers. We synthesized rod-shaped fluorescent particles bearing three distinct regions. Static image scans from regular fluorescence microscopy were compared to those acquired from the raw scans obtained from a single PMT of each machine. After applying FFT-based filtering to isolate the desired frequency response for each machine, the signal from each particle identified was scaled (x-axis only) to compensate for variations in speed and plotted along a common x-axis. Results are shown in FIG. 17 and FIG. 18 below with overlain particle scans and distribution of event width (which inversely correlates with particle speed).

As can be seen, all three cytometers were capable of scanning multifunctional particles with varying levels of accuracy compared to the static scans. Notably, the Guava instrument showed very good reproducibility, but had rounded features, most likely due to a large laser spot size (~25 µm) compared to the dimension of each feature. The Accuri showed fairly reproducible scanning but a significant amount of noise. The Partec showed considerable variability in scan intensity, likely due to a laser spot size that did not span the entire flow cell—most likely, particle brightness was dependent on where the particle was positioned in the flow cell cross-section.

Nucleic Acid Detection

We performed nucleic acid detection using particles with a single, wide fluorescent region to represent a "barcode" and a narrow probe region flanked by two inert regions. We detected microRNA let-7a spiked in at a level of 1 fmol into a 50 µl reaction with hybridization for 90 min at 55 C. Bound target was labeled with streptavidin-phycoerythrin and particles were scanned using the Millipore Guava. The level of fluorescence in the probe region of the particle indicated how much target was present in the assay. The results are shown in FIG. 19.

Again, the results were reproducible but showed rounding of signal at the interfaces between various particle regions. For the highest sensitivity, our assay would benefit from green (532 nm) laser excitation.

Example 8

Two-Strip Encoding with Probe Functionalization

This example demonstrated that compositions described herein may be synthesized and functionalized for encoding, in particular, universal encoding.

Using stop-flow lithography as described in U.S. Pat. No. 7,709,554, the contents of which is incorporated herein by reference, we initially synthesized rectangular particles bearing a stem-loop encoding probe (SEQ ID NO:20) (/5Acryd/AATAAACACGGGAATAACCC, IDT, incorporated at 10 uM), negative control region, probe anchor (SEQ ID NO:21) (/5Acryd/GATATATTTT, IDT, incorporated at 50 uM), and a second negative control region. Particles were ~120×60×35 um and each of the 4 strips was ~30 um thick. Particles were incubated with varying ratios of fluorescently-labeled encoding adapter (SEQ ID NO:22) (5'-Phos- GTGTTTATAA-Cy3, IDT) to unlabeled adapter (SEQ ID NO:23) (5'-Phos-GTGTTTATAA-invdT, IDT). Each ligation mix contained NEBuffer #2 with 250 nM ATP, 200 U T4 DNA Ligase (all from New England Biosciences), and a total of 40 nM encoding adapters. Ligation was carried out for 30 min at room temperature, with mixing at 1500 rpm on a thermomixer. Afterward, particles were rinsed 3× with TE buffer containing 50 mM NaCl and 0.05% Tween-20. Particles were imaged on a Nikon Ti-S microscope using a 20× objective, NA=0.5, and a CCD Camera (Imaging Source). Scans of fluorescent intensity were plotted along the particle length and the fluorescent signals were measured and averaged for five particles in each sample. Typical results are shown in FIG. 20.

Data demonstrates that the labeling worked, but the relationship of fluorescence vs. adapter ratio was not linear. This implies a difference in hybridization or ligation rates between the fluorescent and non-fluorescent adapters used. Unfortunately, the images at the 100% level were saturated, so it is difficult to use all 4 data points for comparison. Raw and scaled data are shown in Table 6:

| RAW DATA | Sig | SD | COV | Normalized | Sig |
|---|---|---|---|---|---|
| 100% | 240.00 | 0.25 | 0.00 | 100% | 1.00 |
| 50% | 201.63 | 2.07 | 0.01 | 50% | 0.84 |
| 25% | 140.43 | 3.55 | 0.03 | 25% | 0.59 |
| 12.50% | 92.07 | 2.45 | 0.03 | 12.50% | 0.38 |

Furthermore, we used universal particles, synthesized using the stop-flow lithography process described above, bearing two encoding regions (with hairpin anchors) and a probe region (with linear anchor). Particles were ~180 um long, 35 um wide, and ~25 um thick with 4 regions— UCode1 (synthesized at ~10 uM), UCode2 (at ~10 uM), inert, and UAnchor (at ~50 uM). DNA sequences used in this study are as follows (as ordered from Integrated DNA Technologies, 5-'3'):

```
                                          (SEQ ID NO: 24)
UCode1 Probe = /5Acryd/AAT AAA CAC GGG AAT AAC CC (SEQ ID NO: 25)
UCode2 Probe = /5Acryd/AAT AAT GTG CCC AAT AAG GG (SEQ ID NO: 26)
UCode 1 Adapter Cy3 = /5Phos/GTG TTT ATT A/3Cy3Sp/

(SEQ ID NO: 27)
UCode 1 Adapter invdT = /5Phos/GTG TTT ATT A/
3InvdT/

(SEQ ID NO: 28)
UCode 2 Adapter Cy3 = /5Phos/CAC ATT ATT A/3Cy3Sp/

(SEQ ID NO: 29)
UCode 2 Adapter invdT = /5Phos/CAC ATT ATT A/
3InvdT/
```

After particles were synthesized and rinsed, we prepared Ligation Master Mixes, each with 250 nM ATP (NEB), 200 U T4 DNA Ligase (NEB), 0.05% Tween-20 (Sigma), and DNA Adapter (given below) in a total of 500 ul NEBuffer #2 (NEB):

F1: 80 nM UCode Adapter 1 Cy3
N1: 80 nM UCode Adapter 1 invdT
F2: 80 nM UCode Adapter 2 Cy3
N2: 80 nM UCode Adapter 2 invdT In a 96-well, 1.2 um filter-bottom plate (Millipore), we added mixes of the ligation mixtures as listed in Table 7:

| | F1 (ul) | N1 (ul) | F2 (ul) | N2 (ul) |
|---|---|---|---|---|
| W1: 1, 1 | 100 | 0 | 100 | 0 |
| W2: 1, 0 | 100 | 0 | 0 | 100 |
| W3: 0, 1 | 0 | 100 | 100 | 0 |
| W4: 1, 0.25 | 100 | 0 | 25 | 75 |
| W5: 0.25, 1 | 25 | 75 | 100 | 0 |
| W6: 0.25, 0.25 | 25 | 75 | 25 | 75 |
| W7: 0.25, 0 | 25 | 75 | 0 | 100 |
| W8: 0, 0.25 | 0 | 100 | 25 | 75 |

We then added 10 ul of particles to each well (~200 particles) and put the plate on mixer, and mixed at 1500 rpm for 30 min at room temp. We then used a filter unit to pull off excess buffer and rinse 2× with 200 ul TE buffer with 0.05% Tween-20 (TET). For imaging, we added 60 ul of TET to each well, mixed for 30 sec and then pipetted 35 ul from each well onto a glass slide. Each sample was sandwiched with an 18×18 mm coverslip. We image particles with Nikon Ti-U microscope with Imaging Source CCD camera with brightness=30, gain=600, exposure=0.412 sec, gamma=150. After imaging 5 particles per sample, w used ImageJ to orient and crop images, and plugged data into Excel for analysis. The raw data from the analysis are shown in Table 8, the ratios representing the amount of fluorescent adapter used (where 1=100%):

| ratio 1 | P1 | SD1 | COV | ratio 2 | P2 | SD2 | COV |
|---|---|---|---|---|---|---|---|
| 1.00 | 85.71 | 2.26 | 0.03 | 1.00 | 78.86 | 1.98 | 0.03 |
| 1.00 | 83.45 | 3.85 | 0.05 | 0.00 | 2.55 | 0.64 | 0.25 |
| 0.00 | 1.42 | 0.25 | 0.18 | 1.00 | 77.96 | 4.22 | 0.05 |
| 1.00 | 85.32 | 3.55 | 0.04 | 0.25 | 46.14 | 1.25 | 0.03 |
| 0.25 | 47.38 | 4.11 | 0.09 | 1.00 | 73.94 | 5.52 | 0.07 |
| 0.25 | 48.98 | 2.40 | 0.05 | 0.25 | 47.86 | 0.87 | 0.02 |
| 0.25 | 48.51 | 0.87 | 0.02 | 0.00 | 1.20 | 0.66 | 0.55 |
| 0.00 | 0.31 | 0.56 | 1.80 | 0.25 | 46.86 | 0.77 | 0.02 |

Shown in FIG. 21 (a and b) is a schematic of the particle design, sample fluorescent images from each ligation reaction, and average scans across particles.

A plot of the measured fluorescence versus the adapter amount from each ligation mix are shown in FIG. 22, where "Code 1" and "Code 2" represent the average signal in the first and second code region, respectively. The encoding worked well. More importantly, the encoding was specific; the signal for each code region seemed to be independent of the other. As observed in the above experiments, the fluorescent level of each code region was not linear with respect to the amount of fluorescent adapter. The signals were very reproducible, especially at the 25% fluorescent adapter levels.

Example 9

Universal Encoding Using Template Functionalization

In this example, universal particles were made, bearing several polynucleotide templates for encoding.

As an example, particles were designed such that there were three active regions separated by two inert regions, and they can be scanned by a commercial cytometer. The DNA templates with acrylate modification (denoted 5' acry) used for encoding are listed below in Table 9:

| Template name: | Sequence |
|---|---|
| UC1 | 5'acry-AATAAACACGGGAATAACCC-3' (SEQ ID NO: 30) |
| UC2 | 5'acry-AATAATGTGCCCAATAAGGG-3' (SEQ ID NO: 31) |
| UC3 | 5'acry-AATAACTCTGGGAATAACCC-3' (SEQ ID NO: 32) |

These templates were used with particles of the design illustrated in FIG. 23. Hydrogel particles, consisting of poly(ethylene glycol), with this design were made using flow lithography as discussed above. The particles were made with monomers containing the following concentrations of polynucleotide templates as listed in Table 10.

|  | Barcode 1 | Inert | Probe | Inert | Barcode 2 |
|---|---|---|---|---|---|
| UC1 | 50 uM | NA | NA | NA | NA |
| UC2 | 2.5 uM | NA | 0.5 uM | NA | 2.5 uM |
| UC3 | NA | NA | NA | NA | 50 uM |

For use in a flow cytometer, the UC2 template is functionalized with a Cy5 modified adapter in order to trigger events in the RED2 channel. For barcoding, the UC1 and UC3 templates are functionalized with blends of adapters (Cy3 modified, FAM-6 modified, or non-fluorescent) in order to achieve distinct levels of fluorescence in the YEL channel of the cytometer for barcoding and distinct levels of fluorescence in the GRN channel for orientation. The sequences of the adapters used are given in Table 11 below:

| Adapter Name | Sequence (5'-3') |
|---|---|
| UC1-A-Cy3 | 5'phos-GTGTTTATTA-Cy3 (SEQ ID NO: 33) |
| UC1-A-NF | 5'phos-GTGTTTATTA (SEQ ID NO: 34) |
| UC1-A-FAM6 | 5'phos-GTGTTTATTA-FAM6 (SEQ ID NO: 35) |
| UC2-Cy5 | 5'phos-CACATTATTA-Cy5 (SEQ ID NO: 36) |
| UC3-A-Cy3 | 5'phos-AGAGTTATTA-Cy3 (SEQ ID NO: 37) |
| UC3-A-NF | 5'phos-AGAGTTATTA (SEQ ID NO: 38) |
| UC3-A-FAM6 | 5'phos-AGAGTTATTA-FAM6 (SEQ ID NO: 39) |

The number of distinguishable fluorescence levels in each barcode region depends on the accuracy of encoding, and performance characteristics of the cytometer being used. To determine the proper code dilutions to maximize multiplexing on a given flow cytometer, several blends of fluorescent and non-fluorescent adapters may be tested for a given encoding template. Several ratios of fluorescent to non-fluorescent adapters were explored by logarithmically varying the ratio between fluorescent and non-fluorescent and ligating multiple batches of particles a curve was generated as seen in FIG. 24. Template functionalization via ligation with adapters was carried out simultaneously for all templates for one hour at room temperature using 0.8 U T4 DNA ligase per ul, 40 nM total adapter for each encoding template (fluorescent or non-fluorescent).

Several dilutions of UC1-A-Cy3 in UC1-A-NF were used to functionalize universal particles in order to develop a titration curve for the fluorescence obtained. The curve in FIG. 24 shows the log(fluorescence) obtained using ratios of Cy3:NF adapter ranging from 0:1 to 1:1. This curve was obtained using YEL fluorescence measurements from a Guava easyCyte 6HT.

Using this methodology, titration curves were made for the UC1 and UC3 templates with Cy3 modified and non-fluorescent adapters. Typical results, showing log (fluorescence), are given in Table 12 below.

| Ratio | 1/Ratio | Corrected Intensity | COV |
|---|---|---|---|
| Barcode 1 | | | |
| 0 | 0 | −0.79 | 17.40% |
| 256 | 0.0039063 | −0.78 | 17.00% |
| 128 | 0.0078125 | −0.74 | 20.40% |
| 64 | 0.015625 | −0.63 | 13.30% |
| 32 | 0.03125 | −0.52 | 12.60% |
| 16 | 0.0625 | −0.33 | 10.80% |
| 8 | 0.125 | −0.1 | 10.00% |
| 4 | 0.25 | 0.15 | 10.90% |
| 2 | 0.5 | 0.43 | 10.90% |
| 1 | 1 | 0.69 | 12.90% |
| Barcode 2 | | | |
| 0 | 0 | −0.8 | 10.80% |
| 256 | 0.00390625 | −0.81 | 8.70% |
| 128 | 0.0078125 | −0.78 | 11.60% |
| 64 | 0.015625 | −0.74 | 10.20% |
| 32 | 0.03125 | −0.69 | 11.70% |
| 16 | 0.0625 | −0.6 | 10.00% |
| 8 | 0.125 | −0.44 | 9.00% |
| 4 | 0.25 | −0.25 | 9.20% |
| 2 | 0.5 | 0.01 | 9.20% |
| 1 | 1 | 0.28 | 11.40% |

Dilutions used for encoding were selected such that the expected fluorescence levels had very little chance of overlap with an adjacent dilution, given the expected coefficient of variation (COV) in the signals measured here. In order to obtain 5 levels for each barcode regions, the following dilutions of non-fluorescent to Cy3-modified adapters in Table 13 were used:

| Log(intensity) | Adapter NF:Cy3 |
|---|---|
| Barcode 1 | |
| −0.79 | 0 |
| −0.42 | 21 |
| −0.05 | 6.7 |
| 0.32 | 2.5 |
| 0.69 | 1 |
| Barcode 2 | |
| −0.80 | 0 |
| −0.53 | 17.7 |
| −0.26 | 4.1 |
| 0.01 | 2 |
| 0.28 | 1 |

With the possibility of generating 5 distinct levels of fluorescence in each Barcode 1 and Barcode 2, a total of 25 unique combinations can be obtained. These dilutions were tested with the universal particles synthesized in this Example. To differentiate the two coding regions, a higher level of green (FAM-6) was added to the dilution series for Barcode 2. The fluorescent adapter for UC2 was also included in the functionalization to generate signal in RED2 which was used to trigger events on the cytometer. Particles were functionalized via simultaneous ligation with blends of adapters for UC1, UC2, and UC3 such that the total concentration of adapter for a given adapter was 40 nM. Reactions were carried out at room temperature for 1 hour with 0.8 U/ul of T4 DNA ligase present. Particles were rinsed in TE buffer and scanned using a Guava 6HT.

Example 10

Scanning Multi-Event Particles with Commercial Cytometers

In this example, universal particles made in Example 12 was used for scanning using commercial cytometers. A Millipore Guave easyCyte 6HT-2L as an exemplary cytometer can be used for scanning.

Here, particles were scanned on a cytometer using RED fluorescence to trigger events, yellow fluorescence to encode particles, and green fluorescence to orient particles. As discussed, particles represented in FIG. 23 are comprised of three active regions (denoted Barcode 1, Probe and Barcode 2), separated by two inert regions. All three active regions contain a Cy5-modified nucleic acid to trigger events in the RED2 channel of a Guava easyCyte cytometer. The level of Cy5 in the probe region was intentionally made to be approximately one half that in the barcoding regions. The two barcode regions contain varying levels of Cy3-modified oligonucleotides. The levels of Cy3 in each barcode region, detected in the YEL channel of the Guava cytometer, are used to give the particle a unique encoding signature. In addition, a FAM6-modified oligonucleotide is incorporated in the barcoding regions, with a higher level in Barcode 1, in order to provide a means of orientation. A mixture containing 25 different particle barcodes, with 5 unique levels of Cy3 fluorescence in Barcode 1 and 5 unique levels in Barcode 2, were used to demonstrate proof-of-concept.

A threshold of 500 set on the RED2 channel with the Guava 6HT was sufficient to allow identification of all three regions of the particle. Hundreds of particles, at a concentration of approximately 20 per microliter in TE buffer, were scanned at 0.6 microliters per second. The events associated with the particles, plotted on YEL (barcoding color) versus RED2 (trigger color) are shown in FIG. 25, along with YEL versus GRN (for orientation). The probe region of the particle appears in the lower left hand side of the plot, with lower levels of green (FAM-6™) and yellow (Cy3υ). The two coding regions of the particles show up as bands on the upper right hand corner of the plot. A total of ten bands can be discerned on the plot, comprising of five codes on the Barcode 1 region of the particle and five codes on the Barcode 2 region. The raw values represented on these plots are then exported into a FCS file for further analysis. All events exported in the CSV are store in temporal sequence.

Custom software was used to analyze the events exported from the Guava software and reconstruct them, based on patterns in the RED2 and GRN fluorescence. The software sorts through the sequence of events to assess whether three subsequent events fit the expected patterns for RED2 and GRN fluorescence. If the pattern is fit, the events are grouped as a particle and can be analyzed for barcode in YEL fluorescence and oriented by GRN fluorescence. After reconstruction, a more coherent plot can be composed using the level of yellow intensity (Cy3™) on Barcode 1 vs. that of Barcode 2 (designated code 1 and code2, respectively). This plot is shown in FIG. 26. Ellipses are used to identify clusters of particles that are associated with each of the 25 barcodes present. As can be seen, the five levels of fluorescence in Barcode 1 (code 1) and Barcode 2 (code 2) can be readily distinguished.

In addition to determining the barcode, the custom software also quantifies the fluorescence associated with captured target in the probe region of the particle, the information of which is stored as the second of the three events associated with a particle. When using a reporting fluorophore that can be detected in the YEL channel, the level of YEL fluorescence in this region indicates the quantity of target present.

Example 11

Development of One-spot Isothermal Nucleic Acid Amplification Assays

This example further illustrates using encoded particles in accordance with the present invention in various applications, such as nucleic acid amplification assays. As previously demonstrated, we has developed various compositions and methods, providing (1) sub-attomole sensitivity, (2) single-nucleotide specificity, (3) rapid scanning, (4) a virtually unlimited encoding density, and (5) low cost. For example, the high performance of our assay is shown for microRNA targets in above Examples, and FIG. 27. The simplicity of our particle synthesis, one-pot assay, and single-color detection described herein enables a new class of low-cost diagnostic tools.

In this project, we will use encoded hydrogel particle assay to develop a point-of-care system that (1) can perform accurate panel-based tests on DNA or RNA from >10 pathogens at once, (2) uses a one-pot, isothermal assay that is rapid and easy to use, and (3) utilizes low-cost disposable cartridges in a hand-held device. We are developing one-pot assays in which we amplify specific genomic targets of pathogens, hybridize the amplicons to barcoded gel particles, and quantify the bound amplicons in a single closed tube, with a single user intervention (sample loading). Multiple species-specific targets will be amplified using isothermal, helicase-dependent amplification (HDA). Fluorescently-labeled amplicons will be free to diffuse into the encoded hydrogel particles and hybridize to their complementary nucleic acid probes embedded throughout (FIG. 28). The flexibility of our innovative microfabrication process allows us to precisely tune the pore size or particles to exclude helicase enzymes (~4.5 nm), which would unwind bound targets. Due to this advantage, the whole process can be carried out without user intervention. After <1 hour, particles will be scanned rapidly in a flow-through channel using fluorescence to read the barcode of each particle and quantify the corresponding targets. It is our intention to make the system cartridge-based with disposable units that can be interfaced with a portable analysis unit.

We further developed one-pot assays as described in various embodiments above, using standard PCR and has recently begun to investigate isothermal assays for the purpose of this project. We used λ-phage DNA as a model system for assay development. First, we designed Tm-matched primers against 2 target regions of lambda with a cross-check against human genomic DNA to avoid non-specific amplification. The amplicons were designed to be ~60 bp in length. Probes were designed to target each amplicon, containing the complementary sequence excluding the binding site for the forward primer. We performed one-pot assays using both standard PCR and isothermal amplification (FIG. 29).

For each assay, we prepared PCR mixes containing a single primer set (forward primer labeled with Cy3), ~50 encoded gel particles with two spatially-separated probes regions for the amplicons, and either λ-phage DNA or human genomic DNA. Using both standard PCR and isothermal amplification, we were able to show specific amplification and hybridization for each amplicon generated and no non-specific amplification of human genomic DNA. We performed a serial dilution of λ-phage from 11,000-11 copies per reaction. Using primer set #1, we were able to detect ~11 copies of template in our preliminary studies using a one-pot assay with standard PCR. Although sensitivity has not been assessed for the isothermal reaction, the signals observed on particles after 60-min reaction were stronger than those obtained from standard PCR after 40 cycles.

Design of Amplification Primers and DNA Detection Probes

For any pathogen, it is necessary to identify genomic targets that are both specific to the pathogen, and conserved over strains. We will build on the work of others developing PCR-based assays for the four pathogens of interest. Targets for genomic HIV RNA include: the pol-integrase region and the env and gag genes. Targets used for PCR-based identification of for typhoid bacterium genome include the tyv, flag, viaB, and ratA genes. Conserved regions for the malarial parasite genome include the 18s rRNA gene and the circumsporozoite (CS) gene. For dengue virus, Gurukumar et al. targeted a conserved region in the 3'UTR of the viral genome. Initially, our experiments are designed to target similar regions for these pathogens.

For multiplexed isothermal amplification, it is necessary to design compatible primer sets that (1) have similar melting temperatures, (2) do not form hetero-dimers, and (3) specifically and efficiently amplify the targets identified for each pathogen species. Because we are developing a "one-pot" assay where the particles are present in the amplification reaction, we have additional considerations including (1) avoiding 3'-extension of the DNA probes embedded in the particle probe-regions, and (2) keeping amplicons small (<100 bp) for rapid diffusion into our particles where they will hybridize. In approaching this challenge, we will learn from an extensive body of literature for primer design in multiplexed amplification [29].

As shown in FIG. 30, primers will be designed to have melting temperatures near 55° C., be ~20 bp in length, and provide amplicons ~60 bp in size. The forward primers will contain a single Cy3 label for fluorescence detection. For each of the pathogen species, we will design several sets of primers that meet the aforementioned requirements. Primer design will be accomplished as follows:

First, potential primers sets will be identified for the species of interest (dengue, typhoid, malaria, and HIV as well as λ-phage and MS2 controls) for commonly-targeted, conserved genomic regions using a primer-design program like Primer3.

Second, each potential primer identified will be assessed for species-specificity via BLAST search.

Third, a script will be written in MATLAB to assess dimer-formation with all other primers (using nearest neighbor calculations), and to identify a total of 30 primer sets (5 for each of the four pathogens and two controls) that meet all requirements.

Optimization of Helicase-Dependent Amplification (HDA) for DNA Detection.

To maximize the probability of success in developing a working isothermal amplification technique, we will begin with commercially available kits and standard protocols, using λ-phage as a model system. We will use the IsoAmp® kit (New England Biosciences) to perform isothermal amplification on ~5000 copies of λ-phage spiked into human genomic DNA as a model system. We will optimize several parameters including (1) primer concentrations (from 0.1 µM-10 µM), (2) primer length (from 20-26 bp), (3) amplification temperature (from 50-65 C), and (4) reaction time (from 10-120 min). The efficiency and yield of the isothermal reaction will be assessed and compared to the yield of a standard 30-cycle PCR reaction that utilizes the same primers and target regions. Polyacrylamide Gel Electrophoresis (PAGE) will be used to make this qualitative comparison, with target band intensity as the standardized metric.

After optimizing reaction conditions, the primer sets for the other DNA species (P. falciparum, and S. typhi) will be interrogated for efficiency and specificity. Again, we will assess amplification efficiency for each primer set by quantifying the amount of target produced in 10, 30, and 90 min isothermal amplification (via PAGE). Specificity will be assessed by performing PCR with a primer set for a given species using human genomic DNA spiked with ~5000 copies of genomic species for all other species. Specific robust reactions will show amplification of only the target sequence. Of the 5 primer sets designed for each species, we will use the three most efficient sets that show good specificity.

The three primer sets for each species will be used in a multiplexed amplification assay with one target present at a time. For multiplexed reactions, target amplification will be accomplished using a fluorescent forward primer, as shown in FIG. 30. For each reaction, the amplification product will be quantified using a 30 min incubation with barcoded gel particles bearing probes for each amplicon (FIG. 31). The DNA probes for each particle will be designed to span the reverse primer and internal region, and will be 3' capped to avoid extension as shown in FIG. 31. This design will allow for one-pot amplification/capture in subsequent studies.

Ideally, the fluorescent signals observed on the particles would be consistent over the 3 amplicons generated for each species. If significant differences in amplification/capture efficiency are observed for the multiplexed amplification, several reaction conditions will be varied in order to normalize the amount of amplicon captured on each particle probe region. First, the relative amounts of primers can be adjusted accordingly to alter the reaction kinetics. Second, primer length can be adjusted in order to change binding efficiency—this will likely affect the primer Tm and increase nonspecific amplification, and is therefore not desirable. Third, we have demonstrated that the rate of capture can be adjusted in a very predictable manner by changing the concentration of probe in each region of the particles.

After normalizing quantified signal for each species, we will perform one-pot assays where amplification and hybridization are completed in the same reaction. We will determine the effects that the particles have on the sensitivity and specificity of the primer sets. Iterative optimization of primer and probe sequences may be necessary, along with reaction temperature and duration. In the case of multiplexed, one-pot assays, we will image particles in both static (microscopy) and flow-through modes. We will monitor and compare sensitivity and reproducibility of the two approaches—these will be important considerations when designing the integrated system proposed in Example 13.

Reverse Transcription of Pathogen Genomic Material.

While the genomic DNA of *P. falciparum* and *S. typhi* can be directly amplified, the detection of HIV-1 and dengue virus, both ssRNA viruses, will require reverse transcription of genomic RNA to cDNA for amplification and analysis. This requires the addition of a reverse transcriptase enzyme into the isothermal amplification reaction. Reverse transcription has been successfully coupled with Helicase-Dependent Amplification [16], and isothermal RT-HAD kits are available commercially (IsoAmp®, NE Biolabs). This is the same kit being used in the previous studies.

We will start with a standard recommended protocol for RNA reverse transcription and cDNA amplification, using Phage MS2 as a model system for optimization. Using the 5 primer sets originally identified for Phage MS2, we will perform a similar optimization as done for DNA amplification. Once optimized, we will assess primer sets for the pathogen RNA targets, again quantifying amplification efficiency and specificity. Using the 3 best primer sets for each RNA species, we will perform a multiplex amplification for each. Again, amplicons will be quantified using encoded gel particles in both static and flow-through modes.

Optimization of One-Pot Assay for Multiplexed Pathogen DNA or RNA Detection.

Having independently optimized both multiplexed detection of DNA targets and RNA targets, we will combine these assays, and optimize for performance and speed. Using a human genomic DNA background, we will spike genomic material from each pathogen into samples at concentrations ranging from 1-100,000 copies. We will investigate and optimize primer concentrations, enzyme concentration, assay duration, and assay temperature. We will evaluate the performance of the assay for each pathogen, measuring specificity, limit of detection, and sensitivity at 100 copies/rxn. It is our goal to demonstrate 95% sensitivity for all pathogens at 100 copies/rxn with an assay time of 60 min.

Although the use of isothermal amplification with a one-step amplification/hybridization reaction capable of detecting both DNA and RNA species in a single sample is ideal, there are several alternative approaches which are perhaps less attractive, but more likely for success.

For example, if Helicase-Dependent Amplification (HDA) does not prove effective, several other isothermal methods will be investigated including Loop-Mediated Isothermal Amplification (LAMP), Strand-Displacement Amplification (SDA), and Nucleic Acid Sequence-Based Amplification (NASBA). Importantly, a NASBA-based assay has previously been approved by the FDA for the detection of HIV-1 and so would serve as an obvious next choice for RNA detection. Alternatively, standard PCR may be used. In fact, microfluidic methods for PCR amplification are becoming very common [30] so the use of this technique would not be out of the question. Also, if the detection of RNA pathogens (which required reverse transcription) and DNA pathogens in the same tube gives rise to insurmountable complications, these assays can be separated into two distinct tests.

In some embodiments, as an alternative approach to one-pot assays, two-step amplification/hybridization can be use in accordance with the present invention. If the particles interfere in any way with the amplification process, it may be necessary to perform amplification and hybridization separately. Envisioning a cartridge-based system in which this technology can be implemented, this assay can still be accomplished on-chip but will require slightly more sophisticated liquid handling. Although this is not the ideal situation, it is manageable and can feasibly meet the needs of diagnostics in the developing world.

Example 12

Validation of One Pot Assay for Multiplexed Pathogen Detection

After developing a one-pot assay for the multiplexed detection of pathogens in Example 11, we will validate it using clinically-relevant samples and benchmark it against pathogen-specific assays developed for quantitative PCR, the current gold standard for nucleic-acid based pathogen diagnostics. This objective will be important in demonstrating the clinical utility of this assay.

We will obtain a representative set of clinically-relevant samples from several collaborators. Without being bound to any particular theory, it is believed that the samples we obtain will be well-preserved. This is especially important for RNA detection as RNA is rapidly degraded by RNase activity. If the available sample volume permits, we will perform quality control via DNA/RNA sizing with an Agilent Bioanalyzer. Another assumption is that these samples will be representative of the samples that would be obtained in the field when our technology is deployed. Ideally, the samples would span a broad range of pathogen load, and states of patients' immunologic response.

There are several stages in the validation of our assay. Initially, we will investigate various methods for purifying nucleic acids from whole blood and determine compatibility with our assay for each pathogen. This will be important in determining which purification technologies could be integrated with our platform after this initial research project is completed. We will ideally be able to select one isolation technique that performs well for all pathogens, and use it for all validation tests. We will purify nucleic acids from the clinical samples (blood or plasma) provided by our collaborators and test the samples using our one-pot test and also commercially-available pathogen qPCR kits. This will allow a direct benchmark of our assay against the current state-of-the-art. Details for each part of the validation process are given below.

Assessment of Nucleic Acid Purification Techniques. There are several methods for extracting nucleic acids from whole blood, plasma, or serum. Most of the kits are specific for either RNA or DNA, though a few kits can be used to extract both. We will investigate several commercially-available kits including:

DNA Extraction: QIAamp Blood DNA Mini Extraction Kit (QIAGEN), Genomic DNA Extraction Kit (Bioneer), Extract-N-Amp Blood PCR Kits (Sigma).

RNA Extraction: QIAmp Viral RNA Mini Extraction Kit (QIAGEN), Viral RNA Extraction Kit (Bioneer).

Simultaneous Extraction of DNA and RNA: QIAamp MinElute Virus Spin Kit, QIAamp UltraSens Virus Kit, NucleoSpin Virus Kit (Macherey-Nagel).

clearly, the optimal mode for multiplexed assays is the use of a single extraction method for parallel isolation of pathogen DNA and RNA. We will devote a significant amount of effort into identifying and optimizing a method for dual nucleic acid extraction that functions well with our one-pot assay. To assess compatibility, we will use well-characterized clinical samples containing each pathogen and perform extraction with each of the kits. The samples will subsequently be assessed with our one-pot assay and also validated using qPCR kits specifically designed for each pathogen.

Assay on clinical Samples with Direct Comparison to qPCR. Nucleic acids from clinical samples (at least 30 for each pathogen type) will be purified using the optimal method determined in the previous section. We will perform a one-pot, multiplexed assay for the detection of pathogens in each sample and compare our results to qPCR assays specifically designed for each pathogen. For three of the four pathogens being investigated, there are several qPCR kits available. At the time we reach this objective, we will select the kit that has shown best performance and has received certification for diagnostic testing:

Dengue: Primer Design, Ltd. and Genome Diagnostics
Malaria: Primer Design, Ltd., AccuPower, and Genome Diagnostics
HIV-1: Primer Design, Ltd., and Genome Diagnostics
Typhoid: To our knowledge, there is no commercially-available qPCR assay for S. typhi. There is a multiplex PCR-based approach by Kumar et al. [11] that will be used in place of qPCR if no test has been developed by the time we reach this objective of the project.

For relative comparison of sensitivity, we will also make serial dilutions of a representative sample for each pathogen type and analyze them using both our assay and the qPCR standard. A strong correlation of our assay results with the state-of-the art is important for validation. If our assay performs less desirably than expected, we will troubleshoot the assay by re-evaluating the regions targeted, primer design, and assay conditions. We will work closely with our collaborators for guidance in resolving any issues.

Example 13

Development of a Proof-of-Concept Integrated System

After successfully developing an assay, it is important to begin conceptualizing methods for the assay to be implemented on chip. For this reason, we will explore methods for performing one-pot assay and analyzing particles in a single chamber. This will require the development of an integrated system capable of precise temperature control with capabilities for fluorescence imaging for static particle analysis or rapid signal acquisition for flow-through analysis. This system will allow periodic analysis of the particles to assess the progress of reaction. As a significant improvement over end-point analysis, we believe that this method of analysis can be calibrated to provide precise quantitative analysis of pathogen load. In this Example, we aim to develop an integrated system to perform rapid, one-pot assays with the ability to accurately quantify pathogen nucleic acids.

As the simplest initial approach, we will use a commercially-available temperature-controlled cell perfusion chamber with static imaging on a microscope. We will perform several studies to evaluate the use of a one-pot chamber reaction for pathogen detection and also assess the feasibility of performing quantitative analysis with periodic image analysis. After successful implementation, we will integrate the heated flow chamber into a stand alone device with an LED illumination source and a CCD camera to acquire images. This represents an important step toward developing a cartridge-based system that would ultimately be deployed in developing countries. More details on the specific activities for this objective are given below.

One Pot-Assays in a Heated Flow Cell. We will use a commercially-available heated flow cell, similar to those sold by Bioptechs. These flow cells feature (1) customizable channel design, (2) multiple interfaces for sample introduction, (3) precise temperature control with +/−0.2° C. stability, and (4) a standard design for mounting on any microscope. Initially, we will utilize a simple rectangular flow chamber for assay and analysis. We will premix the reaction mixture to include the sample of interest, isothermal amplification reagents, and ~50 particles for each of the four pathogens and two controls. The device will be pre-heated to the isothermal amplification temperature (~55° C.) and the reaction mixture will be introduced into the reaction chamber. Using a standard inverted microscope with a 5× objective (for large field of view), single excitation color, and single detection color, particles will be imaged throughout the course of amplification, likely every 5 minutes. Each image will be analyzed to estimate the amount each amplicon generated, based on probe-region fluorescence. After 60 min reaction, this dynamic data will be used to estimate the amount of template initially present. For a proof-of-concept, we will use the two controls, λ-phage DNA and Phage MS2, in order to characterize system performance and ability to provide quantitative data.

Design and Construction of an Integrated Assay/Scanning System. After successful implementation of a microscope-based system, we will integrate the flow cell into a custom optical system. We will utilize a homogeneous LED illumination, a low-magnification lens, and a CCD chip. The LED array, CCD, and heated flow cell will be interfaced with a laptop computer for control, image acquisition, and analysis. The unit will be thoroughly tested, and results will be compared to those obtained previously in this project. We will re-evaluate the sensitivity and specificity of detection for each pathogen using this setup. We will also investigate the quantitative dynamic range of the system by spiking in targets from 1-1M copies. We take measures to ensure that performance is not compromised in an integrated system.

All literature and similar material cited in this application, including, patents, patent applications, articles, books, treatises, dissertations and web pages, regardless of the format of such literature and similar materials, are expressly incorporated by reference in their entirety. In the event that one or more of the incorporated literature and similar materials differs from or contradicts this application, including defined terms, term usage, described techniques, or the like, this application controls.

The section headings used herein are for organizational purposes only and are not to be construed as limiting the subject matter described in any way.

Other Embodiments and Equivalents

While the present disclosures have been described in conjunction with various embodiments and examples, it is not intended that they be limited to such embodiments or examples. On the contrary, the disclosures encompass various alternatives, modifications, and equivalents, as will be appreciated by those of skill in the art. Accordingly, the descriptions, methods and diagrams of should not be read as limited to the described order of elements unless stated to that effect.

Although this disclosure has described and illustrated certain embodiments, it is to be understood that the disclosure is not restricted to those particular embodiments. Rather, the disclosure includes all embodiments that are functional and/or equivalents of the specific embodiments and features that have been described and illustrated.

In accordance with 37 CFR 1.52(e)(5), a Sequence Listing in the form of a text file (entitled "sequence_listing_0005.txt", 13 kilobyte) is incorporated herein by reference in its entirety.

We claim:

1. A method for characterizing a multifunctional particle comprising:
   (a) interrogating the multifunctional object particle with a flow cytometer, wherein the multifunctional particle comprises
      (i) comprising at least one coding region and
      (ii) at least one probe region,
      wherein the at least one coding region and the at least one probe region are each doped with a triggering entity that is detectable above a pre-determined triggering threshold,
      the at least one coding region and the at least one probe region being detectable by the flow cytometer as a sequence of discrete events above the pre-determined triggering threshold, and
      wherein at least one non-detectable region separates the at least one coding region and the at least one probe region;
   (b) detecting and recording, by the flow cytometer, the sequence of discrete events above the pre-determined triggering threshold, wherein each discrete event is designated by one or more numerical values indicative of a measured fluorescence and/or scatter signal; and
   (c) characterizing the sequence of discrete events based on the numerical values thereby characterizing the coding and probing regions of the multifunctional particle.

2. The method of claim 1, wherein the sequence of discrete events are recorded non-contemporaneously.

3. The method of claim 1, wherein the sequence of discrete events are recorded contemporaneously.

4. The method of claim 1, wherein the multifunctional particle is illuminated with one or more lasers or light sources.

5. The method of claim 1, wherein the multifunctional particle comprises two coding regions and one probe region separated by inert spacers.

6. The method of claim 1, wherein the probe region contains DNA, RNA, proteins, and/or cells.

7. The method of claim 1, wherein the probe region comprises a generic linking chemistry.

8. The method of claim 1, wherein the probe region contains a single-stranded polynucleotide template containing capturing sequence specific for a target nucleic acid and an adjacent adapter sequence for binding a universal adapter such that a simultaneous binding of the target nucleic acid and the universal adapter is detectable via post-hybridization labeling.

9. The method of claim 1, wherein the multifunctional particle is a hydrogel particle.

10. The method of claim 1, wherein the at least one coding region comprises a first detectable label and the at least one probe region comprises a second detectable label, wherein the first detectable label and the second detectable label are distinct from each other.

11. The method of claim 10, wherein the first detectable label is a first fluorescent moiety and the second detectable label is a second fluorescent moiety.

12. A method for detecting multiple analytes in a sample comprising:
   (a) mixing a plurality of multifunctional particles with a sample containing one or more target analytes, wherein each individual particle comprises
      (i) at least one coding region and
      (ii) at least one probe region,
      wherein the at least one coding region and the at least one probe region are each doped with a triggering entity that is detectable above a pre-determined triggering threshold,
      the at least one coding region and the at least one probe region being detectable by a flow cytometer as a sequence of discrete events above the pre-determined triggering threshold, and
      wherein at least one non-detectable region separates the at least one coding region and the at least one probe region;
   (b) detecting and recording, by the flow cytometer, the sequence of discrete events above the pre-determined triggering threshold, wherein each discrete event is designated by one or more numerical values indicative of a measured fluorescence and/or scatter signal;

(c) grouping the sequence of discrete events for each multifunctional particle;

(d) detecting the presence of the one or more target analytes by detecting altered events based on the grouping result from the step of grouping the events for each multifunctional particle as compared to a control.

13. The method of claim 12, wherein the sample is selected from cells, tissue, whole blood, plasma, serum, urine, stool, saliva, cord blood, chorionic villus samples amniotic fluid, transcervical lavage fluid, diseased cells (including cancer and/or tumor cells), and any combination thereof.

14. The method of claim 12, wherein the one or more target analytes comprise at least one of proteins, peptides, hormones, haptens, antigens, antibodies, receptors, enzymes, nucleic acids, polysaccharides, chemicals, polymers, pathogens, toxins, organic drugs, inorganic drugs, cells, tissues, microorganisms, viruses, bacteria, fungi, algae, parasites, allergens, pollutants, and any combination thereof.

15. The method of claim 14, wherein the one or more target analytes are nucleic acids comprising at least one of DNA, RNA, or any combination of DNA and RNA, a portion of a gene, a regulatory sequence, genomic DNA, cDNA, RNA including mRNA, rRNA, microRNA, or any combination thereof.

16. The method of claim 12, wherein the one or more target analytes are present at a concentration ranging from 0.1 amol-10,000 amol in the sample.

17. The method of claim 12, wherein the one or more target analytes are present at a concentration below 100 amol in the sample.

18. The method of claim 12, wherein the one or more target analytes are present in a concentration of less than 1% of total nucleic acids in the sample.

* * * * *

SEQUENCE LISTING

<160> NUMBER OF SEQ ID NOS: 39

<210> SEQ ID NO 1
<211> LENGTH: 34
<212> TYPE: DNA
<213> ORGANISM: Artificial Sequence
<220> FEATURE:
<223> OTHER INFORMATION: probe sequence for let-7a
<220> FEATURE:
<221> NAME/KEY: misc_feature
<222> LOCATION: (1)..(1)
<223> OTHER INFORMATION: 5' acrydite
<220> FEATURE:
<221> NAME/KEY: misc_feature
<222> LOCATION: (34)..(34)
<223> OTHER INFORMATION: 3' inverted dT

<400> SEQUENCE: 1
gatatatttt aaactataca acctactacc tcat                     34

<210> SEQ ID NO 2
<211> LENGTH: 34
<212> TYPE: DNA
<213> ORGANISM: Artificial Sequence
<220> FEATURE:
<223> OTHER INFORMATION: probe sequence for miR-21
<220> FEATURE:
<221> NAME/KEY: misc_feature
<222> LOCATION: (1)..(1)
<223> OTHER INFORMATION: 5' acrydite
<220> FEATURE:
<221> NAME/KEY: misc_feature
<222> LOCATION: (34)..(34)
<223> OTHER INFORMATION: 3' inverted dT

<400> SEQUENCE: 2
gatatatttt atcaacatca gtctgataag ctat                     34

<210> SEQ ID NO 3
<211> LENGTH: 35
<212> TYPE: DNA
<213> ORGANISM: Artificial Sequence
<220> FEATURE:
<223> OTHER INFORMATION: probe sequence fof miR-29b-2
<220> FEATURE:
<221> NAME/KEY: misc_feature
<222> LOCATION: (1)..(1)
<223> OTHER INFORMATION: 5' acrydite
<220> FEATURE:
<221> NAME/KEY: misc_feature
<222> LOCATION: (35)..(35)
<223> OTHER INFORMATION: 3' inverted dT

<400> SEQUENCE: 3
gatatatttt aaacactgat ttcaaatggt gctat                    35

<210> SEQ ID NO 4
<211> LENGTH: 35
<212> TYPE: DNA
<213> ORGANISM: Artificial Sequence
<220> FEATURE:
<223> OTHER INFORMATION: probe sequence for miR-18ab-1
<220> FEATURE:
<221> NAME/KEY: misc_feature
<222> LOCATION: (1)..(1)
<223> OTHER INFORMATION: 5' acrydite
<220> FEATURE:
<221> NAME/KEY: misc_feature
<222> LOCATION: (35)..(35)
<223> OTHER INFORMATION: 3' inverted dT

<400> SEQUENCE: 4
gatatatttt aacccaccga cagcaatgaa tgttt                                    35

<210> SEQ ID NO 5
<211> LENGTH: 33
<212> TYPE: DNA
<213> ORGANISM: Artificial Sequence
<220> FEATURE:
<223> OTHER INFORMATION: probe sequence for miR-143
<220> FEATURE:
<221> NAME/KEY: misc_feature
<222> LOCATION: (1)..(1)
<223> OTHER INFORMATION: 5' acrydite
<220> FEATURE:
<221> NAME/KEY: misc_feature
<222> LOCATION: (33)..(33)
<223> OTHER INFORMATION: 3' inverted dT

<400> SEQUENCE: 5
gatatatttt agagctacag tgcttcatct cat                                      33

<210> SEQ ID NO 6
<211> LENGTH: 35
<212> TYPE: DNA
<213> ORGANISM: Artificial Sequence
<220> FEATURE:
<223> OTHER INFORMATION: probe sequence for miR-145
<220> FEATURE:
<221> NAME/KEY: misc_feature
<222> LOCATION: (1)..(1)
<223> OTHER INFORMATION: 5' acrydite
<220> FEATURE:
<221> NAME/KEY: misc_feature
<222> LOCATION: (35)..(35)
<223> OTHER INFORMATION: 3' inverted dT

<400> SEQUENCE: 6
gatatatttt aagggattcc tgggaaaact ggact                                    35

<210> SEQ ID NO 7
<211> LENGTH: 34
<212> TYPE: DNA
<213> ORGANISM: Artificial Sequence
<220> FEATURE:
<223> OTHER INFORMATION: probe sequence for miR-146a
<220> FEATURE:
<221> NAME/KEY: misc_feature
<222> LOCATION: (1)..(1)
<223> OTHER INFORMATION: 5' acrydite
<220> FEATURE:
<221> NAME/KEY: misc_feature
<222> LOCATION: (34)..(34)
<223> OTHER INFORMATION: 3' inverted dT

<400> SEQUENCE: 7
gatatatttt aaacccatgg aattcagttc tcat                                     34

<210> SEQ ID NO 8
<211> LENGTH: 34
<212> TYPE: DNA
<213> ORGANISM: Artificial Sequence
<220> FEATURE:
<223> OTHER INFORMATION: probe sequence for miR-210
<220> FEATURE:
<221> NAME/KEY: misc_feature
<222> LOCATION: (1)..(1)
<223> OTHER INFORMATION: 5' acrydite
<220> FEATURE:
<221> NAME/KEY: misc_feature
<222> LOCATION: (34)..(34)
<223> OTHER INFORMATION: 3' inverted dT

<400> SEQUENCE: 8
gatatatttt atcagccgct gtcacacgca cagt                34

<210> SEQ ID NO 9
<211> LENGTH: 35
<212> TYPE: DNA
<213> ORGANISM: Artificial Sequence
<220> FEATURE:
<223> OTHER INFORMATION: probe sequence for miR-221
<220> FEATURE:
<221> NAME/KEY: misc_feature
<222> LOCATION: (1)..(1)
<223> OTHER INFORMATION: 5' acrydite
<220> FEATURE:
<221> NAME/KEY: misc_feature
<222> LOCATION: (35)..(35)
<223> OTHER INFORMATION: 3' inverted dT

<400> SEQUENCE: 9
gatatatttt agaaacccag cagacaatgt agctt                35

<210> SEQ ID NO 10
<211> LENGTH: 33
<212> TYPE: DNA
<213> ORGANISM: Artificial Sequence
<220> FEATURE:
<223> OTHER INFORMATION: probe sequence for miR-222
<220> FEATURE:
<221> NAME/KEY: misc_feature
<222> LOCATION: (1)..(1)
<223> OTHER INFORMATION: 5' acrydite
<220> FEATURE:
<221> NAME/KEY: misc_feature
<222> LOCATION: (33)..(33)
<223> OTHER INFORMATION: 3' inverted dT

<400> SEQUENCE: 10
gatatatttt aacccagtag ccagatgtag ctt                33

<210> SEQ ID NO 11
<211> LENGTH: 33
<212> TYPE: DNA
<213> ORGANISM: Artificial Sequence
<220> FEATURE:
<223> OTHER INFORMATION: probe sequence for miSpike
<220> FEATURE:
<221> NAME/KEY: misc_feature
<222> LOCATION: (1)..(1)
<223> OTHER INFORMATION: 5' acrydite
<220> FEATURE:
<221> NAME/KEY: misc_feature
<222> LOCATION: (33)..(33)
<223> OTHER INFORMATION: 3' inverted dT

<400> SEQUENCE: 11
gatatatttt aagaccgctc cgccatcctg agt                33

<210> SEQ ID NO 12
<211> LENGTH: 54
<212> TYPE: DNA
<213> ORGANISM: Artificial Sequence
<220> FEATURE:
<223> OTHER INFORMATION: probe sequence for RNU6B
<220> FEATURE:
<221> NAME/KEY: misc_feature
<222> LOCATION: (1)..(1)
<223> OTHER INFORMATION: 5' acrydite
<220> FEATURE:
<221> NAME/KEY: misc_feature
<222> LOCATION: (54)..(54)
<223> OTHER INFORMATION: 3' inverted dT

<400> SEQUENCE: 12
gatatatttt aaaaaatatg gaacgcttca cgaatttgcg tgtcatcctt gcgt    54

<210> SEQ ID NO 13
<211> LENGTH: 34
<212> TYPE: DNA
<213> ORGANISM: Artificial Sequence
<220> FEATURE:
<223> OTHER INFORMATION: let-7a probe
<220> FEATURE:
<221> NAME/KEY: misc_feature
<222> LOCATION: (1)..(1)
<223> OTHER INFORMATION: 5' acrydite
<220> FEATURE:
<221> NAME/KEY: misc_feature
<222> LOCATION: (34)..(34)
<223> OTHER INFORMATION: 3' inverted dT

<400> SEQUENCE: 13
gatatatttt aaactataca acctactacc tcat    34

<210> SEQ ID NO 14
<211> LENGTH: 22
<212> TYPE: RNA
<213> ORGANISM: Artificial Sequence
<220> FEATURE:
<223> OTHER INFORMATION: let-7a target

<400> SEQUENCE: 14
ugagguagua gguuguauag uu    22

<210> SEQ ID NO 15
<211> LENGTH: 10
<212> TYPE: DNA
<213> ORGANISM: Artificial Sequence
<220> FEATURE:
<223> OTHER INFORMATION: UA10-Cy3
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (10)..(10)
<223> OTHER INFORMATION: 3' Cy3

<400> SEQUENCE: 15
taaaatatat    10

<210> SEQ ID NO 16
<211> LENGTH: 10
<212> TYPE: DNA
<213> ORGANISM: Artificial Sequence
<220> FEATURE:
<223> OTHER INFORMATION: UA10-bio
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (10)..(10)
<223> OTHER INFORMATION: 3' biotin

<400> SEQUENCE: 16
taaaatatat    10

<210> SEQ ID NO 17

```
<211> LENGTH: 13
<212> TYPE: DNA
<213> ORGANISM: Artificial Sequence
<220> FEATURE:
<223> OTHER INFORMATION: UA10-bio
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (13)..(13)
<223> OTHER INFORMATION: 3' biotin

<400> SEQUENCE: 17
taaaatatat aaa                                                          13

<210> SEQ ID NO 18
<211> LENGTH: 16
<212> TYPE: DNA
<213> ORGANISM: Artificial Sequence
<220> FEATURE:
<223> OTHER INFORMATION: UA10-bio
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (16)..(16)
<223> OTHER INFORMATION: 3' biotin

<400> SEQUENCE: 18
taaaatatat aaaaaa                                                       16

<210> SEQ ID NO 19
<211> LENGTH: 22
<212> TYPE: DNA
<213> ORGANISM: Artificial Sequence
<220> FEATURE:
<223> OTHER INFORMATION: UA10-bio
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (22)..(22)
<223> OTHER INFORMATION: 3' biotin

<400> SEQUENCE: 19
taaaatatat aaaaaaaaaa aa                                                22

<210> SEQ ID NO 20
<211> LENGTH: 20
<212> TYPE: DNA
<213> ORGANISM: Artificial Sequence
<220> FEATURE:
<223> OTHER INFORMATION: stem-loop encoding probe
<220> FEATURE:
<221> NAME/KEY: misc_feature
<222> LOCATION: (1)..(1)
<223> OTHER INFORMATION: 5' acrydite

<400> SEQUENCE: 20
aataaacacg ggaataaccc                                                   20

<210> SEQ ID NO 21
<211> LENGTH: 10
<212> TYPE: DNA
<213> ORGANISM: Artificial Sequence
```

```
<220> FEATURE:
<223> OTHER INFORMATION: probe anchor
<220> FEATURE:
<221> NAME/KEY: misc_feature
<222> LOCATION: (1)..(1)
<223> OTHER INFORMATION: 5' acrydite

<400> SEQUENCE: 21
gatatatttt                                                             10

<210> SEQ ID NO 22
<211> LENGTH: 10
<212> TYPE: DNA
<213> ORGANISM: Artificial Sequence
<220> FEATURE:
<223> OTHER INFORMATION: fluorescently-labeled encoding adapter
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (10)..(10)
<223> OTHER INFORMATION: Cy3

<400> SEQUENCE: 22
gtgtttataa                                                             10

<210> SEQ ID NO 23
<211> LENGTH: 11
<212> TYPE: DNA
<213> ORGANISM: Artificial Sequence
<220> FEATURE:
<223> OTHER INFORMATION: unlabeled adapter
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (11)..(11)
<223> OTHER INFORMATION: inverted dT

<400> SEQUENCE: 23
gtgtttataa t                                                           11

<210> SEQ ID NO 24
<211> LENGTH: 20
<212> TYPE: DNA
<213> ORGANISM: Artificial Sequence
<220> FEATURE:
<223> OTHER INFORMATION: UCode1 probe
<220> FEATURE:
<221> NAME/KEY: misc_feature
<222> LOCATION: (1)..(1)
<223> OTHER INFORMATION: 5' acrydite

<400> SEQUENCE: 24
aataaacacg ggaataaccc                                                  20

<210> SEQ ID NO 25
<211> LENGTH: 20
<212> TYPE: DNA
<213> ORGANISM: Artificial Sequence
<220> FEATURE:
<223> OTHER INFORMATION: UCode2 probe
<220> FEATURE:
<221> NAME/KEY: misc_feature
<222> LOCATION: (1)..(1)
<223> OTHER INFORMATION: 5' acrydite
```

```
<400> SEQUENCE: 25
aataatgtgc ccaataaggg                                                    20

<210> SEQ ID NO 26
<211> LENGTH: 10
<212> TYPE: DNA
<213> ORGANISM: Artificial Sequence
<220> FEATURE:
<223> OTHER INFORMATION: UCode 1 adapter Cy3
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (9)..(9)
<223> OTHER INFORMATION: 3' Cy3Sp

<400> SEQUENCE: 26
gtgtttatta                                                               10

<210> SEQ ID NO 27
<211> LENGTH: 11
<212> TYPE: DNA
<213> ORGANISM: Artificial Sequence
<220> FEATURE:
<223> OTHER INFORMATION: UCode 1 adapter invdT
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (11)..(11)
<223> OTHER INFORMATION: 3' inverted dT

<400> SEQUENCE: 27
gtgtttatta t                                                             11

<210> SEQ ID NO 28
<211> LENGTH: 10
<212> TYPE: DNA
<213> ORGANISM: Artificial Sequence
<220> FEATURE:
<223> OTHER INFORMATION: UCode 2 adapter Cy3
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (10)..(10)
<223> OTHER INFORMATION: 3' Cy3Sp

<400> SEQUENCE: 28
cacattatta                                                               10

<210> SEQ ID NO 29
<211> LENGTH: 11
<212> TYPE: DNA
<213> ORGANISM: Artificial Sequence
<220> FEATURE:
<223> OTHER INFORMATION: UCode 2 adapter invdT
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (11)..(11)
<223> OTHER INFORMATION: 3' inverted dT
```

```
<400> SEQUENCE: 29
cacattatta t                                                          11

<210> SEQ ID NO 30
<211> LENGTH: 20
<212> TYPE: DNA
<213> ORGANISM: Artificial Sequence
<220> FEATURE:
<223> OTHER INFORMATION: UC1
<220> FEATURE:
<221> NAME/KEY: misc_feature
<222> LOCATION: (1)..(1)
<223> OTHER INFORMATION: 5' acrylate

<400> SEQUENCE: 30
aataaacacg ggaataaccc                                                 20

<210> SEQ ID NO 31
<211> LENGTH: 20
<212> TYPE: DNA
<213> ORGANISM: Artificial Sequence
<220> FEATURE:
<223> OTHER INFORMATION: US2
<220> FEATURE:
<221> NAME/KEY: misc_feature
<222> LOCATION: (1)..(1)
<223> OTHER INFORMATION: 5' acrylate

<400> SEQUENCE: 31
aataatgtgc ccaataaggg                                                 20

<210> SEQ ID NO 32
<211> LENGTH: 20
<212> TYPE: DNA
<213> ORGANISM: Artificial Sequence
<220> FEATURE:
<223> OTHER INFORMATION: UC3
<220> FEATURE:
<221> NAME/KEY: misc_feature
<222> LOCATION: (1)..(1)
<223> OTHER INFORMATION: 5' acrylate

<400> SEQUENCE: 32
aataactctg ggaataaccc                                                 20

<210> SEQ ID NO 33
<211> LENGTH: 10
<212> TYPE: DNA
<213> ORGANISM: Artificial Sequence
<220> FEATURE:
<223> OTHER INFORMATION: UC1-A-Cy3
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (10)..(10)
<223> OTHER INFORMATION: 3' Cy3

<400> SEQUENCE: 33
gtgtttatta                                                            10

<210> SEQ ID NO 34
<211> LENGTH: 10
<212> TYPE: DNA
<213> ORGANISM: Artificial Sequence
<220> FEATURE:
```

```
<223> OTHER INFORMATION: UC1-A-NF
<220> FEATURE:
<221> NAME/KEY: misc_feature
<222> LOCATION: (1)..(1)
<223> OTHER INFORMATION: 5' phosphate

<400> SEQUENCE: 34
gtgtttatta                                                              10

<210> SEQ ID NO 35
<211> LENGTH: 10
<212> TYPE: DNA
<213> ORGANISM: Artificial Sequence
<220> FEATURE:
<223> OTHER INFORMATION: UC1-A-FAM6
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (10)..(10)
<223> OTHER INFORMATION: 3' FAM6

<400> SEQUENCE: 35
gtgtttatta                                                              10

<210> SEQ ID NO 36
<211> LENGTH: 10
<212> TYPE: DNA
<213> ORGANISM: Artificial Sequence
<220> FEATURE:
<223> OTHER INFORMATION: UC2-Cy5
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (10)..(10)
<223> OTHER INFORMATION: 3' Cy5

<400> SEQUENCE: 36
cacattatta                                                              10

<210> SEQ ID NO 37
<211> LENGTH: 10
<212> TYPE: DNA
<213> ORGANISM: Artificial Sequence
<220> FEATURE:
<223> OTHER INFORMATION: UC3-A-Cy3
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (10)..(10)
<223> OTHER INFORMATION: 3' Cy3

<400> SEQUENCE: 37
agagttatta                                                              10

<210> SEQ ID NO 38
<211> LENGTH: 10
<212> TYPE: DNA
<213> ORGANISM: Artificial Sequence
<220> FEATURE:
<223> OTHER INFORMATION: UC3-A-NF
<220> FEATURE:
<221> NAME/KEY: misc_feature
```

```
<222> LOCATION: (1)..(1)
<223> OTHER INFORMATION: 5' phosphate

<400> SEQUENCE: 38
agagttatta                                                              10

<210> SEQ ID NO 39
<211> LENGTH: 10
<212> TYPE: DNA
<213> ORGANISM: Artificial Sequence
<220> FEATURE:
<223> OTHER INFORMATION: UC3-A-FAM6
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (10)..(10)
<223> OTHER INFORMATION: 3' FAM6

<400> SEQUENCE: 39
agagttatta                                                              10
```